United States Patent
Tsien et al.

(10) Patent No.: US 9,808,532 B2
(45) Date of Patent: *Nov. 7, 2017

(54) PEPTIDES WHOSE UPTAKE IN CELLS IS CONTROLLABLE

(75) Inventors: Roger Tsien, La Jolla, CA (US); Emilia Olson, Seattle, WA (US); Tao Jiang, San Diego, CA (US); Quyen Nguyen, Del Mar, CA (US); Michael Whitney, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 701 days.

This patent is subject to a terminal disclaimer.

(21) Appl. No.: 13/384,581

(22) PCT Filed: Jul. 15, 2010

(86) PCT No.: PCT/US2010/042188
§ 371 (c)(1),
(2), (4) Date: Feb. 16, 2012

(87) PCT Pub. No.: WO2011/008996
PCT Pub. Date: Jan. 20, 2011

(65) Prior Publication Data
US 2012/0134922 A1    May 31, 2012

Related U.S. Application Data

(60) Provisional application No. 61/225,872, filed on Jul. 15, 2009.

(51) Int. Cl.
| | | |
|---|---|---|
| A61B 10/00 | (2006.01) | |
| A61B 5/00 | (2006.01) | |
| A61B 8/00 | (2006.01) | |
| A61K 47/48 | (2006.01) | |
| A61K 49/00 | (2006.01) | |
| C07K 7/06 | (2006.01) | |

(52) U.S. Cl.
CPC .. *A61K 47/48215* (2013.01); *A61K 47/48207* (2013.01); *A61K 47/48238* (2013.01); *A61K 47/48815* (2013.01); *A61K 49/0032* (2013.01); *A61K 49/0056* (2013.01); *C07K 7/06* (2013.01)

(58) Field of Classification Search
CPC ........ A61K 47/48207; A61K 47/48215; A61K 51/00; A61K 51/08; A61K 51/088; A61K 2121/00; A61K 2123/00; A61K 38/00; A61K 38/16; A61K 47/48815; A61K 47/48238; A61K 49/00; A61K 49/0032; A61K 49/0056; A61K 47/00; C07K 7/06
USPC .......... 424/1.11, 1.65, 1.69, 1.81, 1.85, 1.89, 424/9.1, 9.2, 9.3, 9.4, 9.5, 9.6, 9.7, 9.8; 530/300, 324; 534/7, 10-16
See application file for complete search history.

(56) References Cited

U.S. PATENT DOCUMENTS

| | | | |
|---|---|---|---|
| 4,466,919 A | 8/1984 | Weingarten | |
| 4,507,389 A | 3/1985 | Weingarten | |
| 5,434,073 A * | 7/1995 | Dawson ........... | C12Y 304/2106 424/94.64 |
| 5,674,980 A | 10/1997 | Frankel et al. | |
| 5,747,641 A | 5/1998 | Frankel et al. | |
| 5,910,300 A | 6/1999 | Tournier et al. | |
| 6,306,993 B1 | 10/2001 | Rothbard et al. | |
| 6,348,185 B1 | 2/2002 | Piwnica-Worms | |
| 6,592,847 B1 | 7/2003 | Weissleder et al. | |
| 7,431,915 B2 * | 10/2008 | Jiang et al. .................. | 424/1.69 |
| 7,985,401 B2 * | 7/2011 | Jiang et al. .................. | 424/1.69 |
| 8,110,554 B2 * | 2/2012 | Jiang et al. .................. | 514/21.6 |
| 8,486,373 B2 | 7/2013 | Weissleder et al. | |
| 8,642,561 B2 * | 2/2014 | Jiang et al. .................. | 514/21.6 |
| 9,072,792 B2 | 7/2015 | Jiang et al. | |
| 2001/0021763 A1 | 9/2001 | Harris et al. | |
| 2002/0009786 A1 | 1/2002 | Tang et al. | |
| 2003/0176335 A1 | 9/2003 | Zhang et al. | |
| 2004/0009122 A1 | 1/2004 | Klaveness et al. | |
| 2004/0241096 A1 | 12/2004 | Bogdanov et al. | |
| 2005/0069494 A1 | 3/2005 | Li et al. | |
| 2005/0107583 A1 | 5/2005 | Jiang et al. | |
| 2006/0041105 A1 | 2/2006 | Jiang et al. | |
| 2007/0041904 A1 | 2/2007 | Jiang et al. | |
| 2009/0004118 A1 | 1/2009 | Nie et al. | |
| 2011/0160147 A1 | 6/2011 | Dal Pozzo et al. | |

(Continued)

FOREIGN PATENT DOCUMENTS

| | | |
|---|---|---|
| EP | 2 399 939 A2 | 12/2011 |
| WO | WO 01/75067 A2 | 10/2001 |

(Continued)

OTHER PUBLICATIONS

Jiang et al, PNAS 2004, vol. 101, No. 51, pp. 17867-17872.*
Olsen et al (Integr. Biol. (Camb), Jun. 2012, vol. 4, No. 6, pp. 595-605).*
Olson (Activatable Cell Penetrating Peptides for Imaging Protease Activity In Vivo, 2008, Dissertation, 170 pages).*
Whitney et al, Journal of Biological Chemistry, May 11, 2010, vol. 285, No. 29, pp. 22532-22541.*
Gallwitz et al, Plos One, 2012, vol. 7, Issue 2, pp. e31756-e31756.*
Sperling et al, Society for Biomaterials, 2013, Abstract #208.*
Maitz et al, Nature Communications, 2013, pp. 1-7.*
Proimmune, "think peptides® the source for all peptides for your research," 2012, pp. 1-15.

(Continued)

*Primary Examiner* — D L Jones
(74) *Attorney, Agent, or Firm* — Morgan, Lewis & Bockius LLP

(57) ABSTRACT

Disclosed herein, in certain embodiments, is a selective transport molecule with increased in vivo circulation. In some embodiments, a selective transport molecule disclosed herein has the formula (A-X-B-C)n-M, wherein C is a cargo moiety; A is a peptide with a sequence comprising 5 to 9 consecutive acidic amino acids, wherein the amino acids are selected from: aspartates and glutatmates; B is a peptide with a sequence comprising 5 to 20 consecutive basic amino acids; X is a linker; and M is a macromolecular carrier.

11 Claims, 26 Drawing Sheets

(56) References Cited

U.S. PATENT DOCUMENTS

| | | |
|---|---|---|
| 2012/0014873 A1 | 1/2012 | Jiang et al. |
| 2012/0148610 A1 | 6/2012 | Doronina et al. |
| 2013/0176335 A1 | 7/2013 | Sugiyama et al. |

FOREIGN PATENT DOCUMENTS

| | | |
|---|---|---|
| WO | 2004/042034 A1 | 5/2005 |
| WO | WO 2005/042034 A1 | 5/2005 |
| WO | WO 2006/125134 A1 | 11/2006 |
| WO | WO 2013/019681 A2 | 2/2013 |
| WO | WO 2014/120837 A2 | 8/2014 |

OTHER PUBLICATIONS

International Search Report for International Application No. PCT/US2010/042188, filed on Jul. 15, 2010, 5 pages.

Bartles, J.R. et al., "Identification and charactzerization of espin, an actin-binding protein localized to the F-actin0rich junctionla plagues of Sertoli cell ectoplasmic specializations," Journal of Cell Science, 1996, vol. 109, No. 6, pp. 1229-1239.

Bhorade, R. et al., "Macrocyclic Chelators with Paramagnetic Cations Are Internalized into Mammalian Cells via a HIV-Tat Derived Membrane Translocation Peptide," Bioconjugate Chemistry, May 1, 2000, vol. 11, No. 3, pp. 301-305.

Golub et al., Science, Oct. 15, 1999, pp. 531-537.

Jiang, T et al., "Tumor imaging by means of proteolytic activation of cell-penetrating peptides," PNAS, Dec. 21, 2004, pp. 17867-17872, vol. 101, No. 51.

Rothbard, J. B. et al., "Conjugation of arginine oligomers to cyclosporin A facilitates topical delivery and inhibition of inflammation," Nature Medicine, Nov. 2000, vol. 6, No. 11, pp. 1253-1257.

Rothbard, J.B. et at., "Arginine-Rich Molecular Transporters for Drug Delivery: Role of Backbone Spacing in Cellular Uptake," J. Med. Chem., 2002, vol. 45, pp. 3612-3613.

Tung, C-H. et al., "Arginine containing peptides as delivery vectors," Advanced Drug Delivery Reviews, 2003, vol. 55, pp. 281-294.

Ullrich, K.J. et al., "Controluminal para-arninohippurate (PAH) transport in the proximal tubule of the rat kidney," Pflügers Arch., 1989, vol. 415, pp. 342-350.

Wang, V. et al., "Visualizing the mechanical activation of Src," Nature, Apr. 21, 2005, pp. 1040-1045, vol. 434.

Wender, P.A. et al., "The design, synthesis, and evaluation of molecules that enable or enhance cellular uptake: Peptoid molcular transporters," PNAS, Nov. 21, 2000, vol. 97, No. 24, pp. 13003-13008.

Olson, E.S. et al., "Activatable cell penetrating peptides linked to nanoparticles as dual probes for in vivo fluorescence and MR imaging of proteases," PNAS, Mar. 2, 2010, vol. 107, No. 9, pp. 4311-4316.

Aguilera, T.A. et al., "Systemic in vivo distribution of activatable cell penetrating peptides is superior to that of cell penetrating peptides," Integr. Biol., 2009 vol. 1, pp. 371-381.

Nguyen, Q.T. et al., "Surgery with molecular fluorescence imaging using activatable cell-penetrating peptides decreases residual cancer and improves survival," PNAS, Mar. 2, 2010, vol. 107, No. 9, pp. 4317-4322.

Olson, E.S., "Activatable cell penetrating peptides for imaging protease activity in vivo," Electronic Theses and Dissertations UC San Diego, 2008, 152 pages.

Olson, E.S. et al., "In vivo characterization of activatable cell penetrating peptides for targeting protease activity in cancer," Integr. Biol., 2009, vol. 1, pp. 382-393.

Olson, E.S. et al., "In vivo fluorescence imaging of atherosclerotic plaques with activatable cell-penetrating peptides targeting thrombin activity," Integr Biol (Camb), Jun. 2012, vol. 4, No. 6, pp. 595-605.

Arnold, D. et al., "Substrate specificity of cathepsins D and E determined by N-terminal C-terminal sequencing of peptide pools," Eur. J. Biochem., 1997, vol. 249, pp. 171-179. and.

Bremer, C. et al., "Optical Imaging of Matrix Metalloproteinase-2 Activity in Tumors: Feasability Study in a Mouse Model," Radiology, 2001, vol. 221, pp. 523-529.

Chen, E.I. et al., "A Unique Substrate Recognition Profile for Matrix Metalloprotinase-2," The Journal of Biological Chemistry, Feb. 8, 2002, vol. 277, No. 6, pp. 4485-4491.

Chen, J. et al., "'Zipper' Molecular Beacons: A Generalized Strategy to Optimize the Performance of Activatable Protease Probes," Bioconjugate Chem., 2009, vol. 20, pp. 1836-1842.

Jaffer, F.A. et al., "In Vivo Imaging of Thrombin Activity in Experimental Thrombi With Thrombin-Sensitive Near-Infrared Molecular Probe," Arterioscler Thromb Vasc Biol., 2002, vol. 22, pp. 1929-1935.

Ryppa, C. et al., "In Vitro and In Vivo Evaluation of Doxorubicin Conjugates with the Divalent Peptide E-[c(RGDfK)2] that Targets Integrin $\alpha v \beta 3$," Bioconjugate Chem., 2008, vol. 19, pp. 1414-1422.

Scherer, R.L. et al., "Optical imaging of matrix metrixmetalloproteinase-7 activity in vivo using a proteolytic nanobeacon," Mol Imaging, 2008, vol. 7, No. 3, pp. 118-131.

Stary, H. et al., "A Definition of Advanced Type of Atherosclerotic Lesions and A Histologicial Classification of Atherosclerosis: A Report From the Committee on Vascular Lesions of the Council on Arteriosclerosis, American Heart Association," Circulation, Sep. 1995, vol. 92, No. 5, pp. 355-374.

Tsien, R.Y. et al., "Practical design criteria for a dynamic ratio imaging system," Cell Calcium, 1990, vol. 11, pp. 93-109.

Tsien, R.Y., "Indicators Based on Fluorescence Resonance Energy Transfer (FRET)," Imaging in Neuroscience and Development, Jul. 2009, vol. 4, No. 7, pp. 1-7.

Tung, C-H. et al., "A Novel Near-Infrared Fluorescence Sensor for Detection of Thrombin Activation in Blood," ChemBioChem, 2002, vol. 3, pp. 207-211.

Van Vlerken, L.E. et al., "Poly(ethylene glycol)-modified Nanocarriers for Tumor-targeted and Intracellular Delivery," Pharmaceutical Research, Aug. 2007, vol. 24, No. 8, pp. 1404-1414.

Vartak, D.G. et al., "In vitro evaluation of functional interaction of integrin $\alpha v \beta 3$ and matrix metalloprotease-2," Mol Pharm., 2009, vol. 6, No. 6, pp. 1856-1867.

\* cited by examiner

SEQUENCE LISTING

```
<160> NUMBER OF SEQ ID NOS: 22

<210> SEQ ID NO 1
<211> LENGTH: 6
<212> TYPE: PRT
<213> ORGANISM: Artificial Sequence
<220> FEATURE:
<223> OTHER INFORMATION: cleavable linker

<400> SEQUENCE: 1

Asp Pro Arg Ser Phe Leu
1               5

<210> SEQ ID NO 2
<211> LENGTH: 6
<212> TYPE: PRT
<213> ORGANISM: Artificial Sequence
<220> FEATURE:
<223> OTHER INFORMATION: cleavable linker

<400> SEQUENCE: 2

Pro Pro Arg Ser Phe Leu
1               5

<210> SEQ ID NO 3
<211> LENGTH: 18
<212> TYPE: PRT
<213> ORGANISM: Artificial Sequence
<220> FEATURE:
<223> OTHER INFORMATION: cleavable linker
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)
<223> OTHER INFORMATION: AMIDATION

<400> SEQUENCE: 3

Asp Trp Phe Lys Ala Phe Tyr Asp Lys Val Ala Glu Lys Phe Lys Glu
1               5                   10                  15

Ala Phe

<210> SEQ ID NO 4
<211> LENGTH: 6
<212> TYPE: PRT
<213> ORGANISM: Artificial Sequence
<220> FEATURE:
<223> OTHER INFORMATION: cleavable linker

<400> SEQUENCE: 4

Pro Leu Gly Leu Ala Gly
1               5
```

<210> SEQ ID NO 5
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (6)..(6)
<223> OTHER INFORMATION: Leu modified by attachment to Cy5

<400> SEQUENCE: 5

Pro Pro Arg Ser Phe Leu
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (6)..(6)
<223> OTHER INFORMATION: Leu modified by attachment to Rhodamine

<400> SEQUENCE: 6

Asp Pro Arg Ser Phe Leu
1               5

<210> SEQ ID NO 7
<211> LENGTH: 11
<212> TYPE: PRT
<213> ORGANISM: Artificial Sequence
<220> FEATURE:
<223> OTHER INFORMATION: JNK Inhibitor VI
<220> FEATURE:
<221> NAME/KEY: MOD_RES
<222> LOCATION: (11)..(11)
<223> OTHER INFORMATION: AMIDATION

<400> SEQUENCE: 7

Arg Pro Lys Arg Pro Thr Thr Leu Asn Leu Phe
1               5                   10

<210> SEQ ID NO 8
<211> LENGTH: 16
<212> TYPE: PRT
<213> ORGANISM: Artificial Sequence
<220> FEATURE:
<223> OTHER INFORMATION: SC 3036

<400> SEQUENCE: 8

Lys Lys His Thr Asp Asp Gly Tyr Met Pro Met Ser Pro Gly Val Ala
1               5                   10                  15

<210> SEQ ID NO 9
<211> LENGTH: 28
<212> TYPE: PRT
<213> ORGANISM: Artificial Sequence
<220> FEATURE:
<223> OTHER INFORMATION: NEMO-Binding Domain Binding Peptide

<400> SEQUENCE: 9

Asp Arg Gln Ile Lys Ile Trp Phe Gln Asn Arg Arg Met Lys Trp Lys
1               5                   10                  15

Lys Thr Ala Leu Asp Trp Ser Trp Leu Gln Thr Glu

```
                20                  25

<210> SEQ ID NO 10
<211> LENGTH: 26
<212> TYPE: PRT
<213> ORGANISM: Artificial Sequence
<220> FEATURE:
<223> OTHER INFORMATION: NF-kB SN50

<400> SEQUENCE: 10

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 11
<211> LENGTH: 29
<212> TYPE: PRT
<213> ORGANISM: Artificial Sequence
<220> FEATURE:
<223> OTHER INFORMATION: TIRAP Inhibitor Peptide

<400> SEQUENCE: 11

Arg Gln Ile Lys Ile Trp Phe Asn Arg Arg Met Lys Trp Lys Lys Leu
1               5                   10                  15

Gln Leu Arg Asp Ala Ala Pro Gly Gly Ala Ile Val Ser
            20                  25

<210> SEQ ID NO 12
<211> LENGTH: 4
<212> TYPE: PRT
<213> ORGANISM: Artificial Sequence
<220> FEATURE:
<223> OTHER INFORMATION: caspase-9 inhibitor Z-LEHD-FMK
<220> FEATURE:
<221> NAME/KEY: MOD_RES
<222> LOCATION: (1)..(1)
<223> OTHER INFORMATION: Leu modified by attachment to benzyloxycarbonyl
      group
<220> FEATURE:
<221> NAME/KEY: MOD_RES
<222> LOCATION: (2)..(2)
<223> OTHER INFORMATION: Glu modified by O-methylation
<220> FEATURE:
<221> NAME/KEY: MOD_RES
<222> LOCATION: (4)..(4)
<223> OTHER INFORMATION: Asp modified by O-methylation and by attachment
      to fluoromethyl ketone (FMK)

<400> SEQUENCE: 12

Leu Glu His Asp
1

<210> SEQ ID NO 13
<211> LENGTH: 4
<212> TYPE: PRT
<213> ORGANISM: Artificial Sequence
<220> FEATURE:
<223> OTHER INFORMATION: caspase-9 inhibitor Ac-LEHD-CHO
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: modified by oxidation of the terminal backbone
      carboxyl group to an aldehyde

<400> SEQUENCE: 13
```

```
Leu Glu His Asp
1

<210> SEQ ID NO 14
<211> LENGTH: 4
<212> TYPE: PRT
<213> ORGANISM: Artificial Sequence
<220> FEATURE:
<223> OTHER INFORMATION: caspase-8 inhibitor Ac-IETD-CHO
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: modified by oxidation of the terminal backbone
      carboxyl group to an aldehyde

<400> SEQUENCE: 14

Ile Glu Thr Asp
1

<210> SEQ ID NO 15
<211> LENGTH: 4
<212> TYPE: PRT
<213> ORGANISM: Artificial Sequence
<220> FEATURE:
<223> OTHER INFORMATION: caspase-8 inhibitor Z-IETD-CHO
<220> FEATURE:
<221> NAME/KEY: MOD_RES
<222> LOCATION: (1)..(1)
<223> OTHER INFORMATION: Ile modified by attachment to benzyl carbonyl
      group
<220> FEATURE:
<221> NAME/KEY: MOD_RES
<222> LOCATION: (2)..(2)
<223> OTHER INFORMATION: Glu modified by O-methylation
<220> FEATURE:
<221> NAME/KEY: MOD_RES
<222> LOCATION: (4)..(4)
<223> OTHER INFORMATION: Asp modified by O-methylation and by attachment
      to fluoromethyl ketone (FMK)

<400> SEQUENCE: 15

Ile Glu Thr Asp
1

<210> SEQ ID NO 16
<211> LENGTH: 4
<212> TYPE: PRT
<213> ORGANISM: Artificial Sequence
<220> FEATURE:
<223> OTHER INFORMATION: caspase-9 fluorescent inhibitor FAM-LEHD-FMK
<220> FEATURE:
<221> NAME/KEY: MOD_RES
<222> LOCATION: (1)..(1)
<223> OTHER INFORMATION: Leu modified by attachment to fluorescein
      amidite (FAM)
<220> FEATURE:
<221> NAME/KEY: MOD_RES
<222> LOCATION: (4)..(4)
<223> OTHER INFORMATION: Asp modified by attachment to fluoromethyl
      ketone (FMK)

<400> SEQUENCE: 16

Leu Glu His Asp
1

<210> SEQ ID NO 17
<211> LENGTH: 4
```

```
<212> TYPE: PRT
<213> ORGANISM: Artificial Sequence
<220> FEATURE:
<223> OTHER INFORMATION: caspase-8 fluorescent inhibitor FAM-LETD-FMK
<220> FEATURE:
<221> NAME/KEY: MOD_RES
<222> LOCATION: (1)..(1)
<223> OTHER INFORMATION: Leu modified by attachment to fluorescein
      amidite (FAM)
<220> FEATURE:
<221> NAME/KEY: MOD_RES
<222> LOCATION: (4)..(4)
<223> OTHER INFORMATION: Asp modified by attachment to fluoromethyl
      ketone (FMK)

<400> SEQUENCE: 17

Leu Glu Thr Asp
1

<210> SEQ ID NO 18
<211> LENGTH: 6
<212> TYPE: PRT
<213> ORGANISM: Artificial Sequence
<220> FEATURE:
<223> OTHER INFORMATION: cleavable peptide
<220> FEATURE:
<221> NAME/KEY: MOD_RES
<222> LOCATION: (1)..(1)
<223> OTHER INFORMATION: Pro modified by attachment to aminohexanoic
      acid (aminocaproic acid)

<400> SEQUENCE: 18

Pro Leu Gly Leu Ala Gly
1               5

<210> SEQ ID NO 19
<211> LENGTH: 6
<212> TYPE: PRT
<213> ORGANISM: Artificial Sequence
<220> FEATURE:
<223> OTHER INFORMATION: clevable peptide
<220> FEATURE:
<221> NAME/KEY: MOD_RES
<222> LOCATION: (1)..(1)
<223> OTHER INFORMATION: Asp modified by attachment to aminohexanoic
      acid (aminocaproic acid) or Peg-2

<400> SEQUENCE: 19

Asp Pro Arg Ser Phe Leu
1               5

<210> SEQ ID NO 20
<211> LENGTH: 6
<212> TYPE: PRT
<213> ORGANISM: Artificial Sequence
<220> FEATURE:
<223> OTHER INFORMATION: cleavable peptide
<220> FEATURE:
<221> NAME/KEY: MOD_RES
<222> LOCATION: (1)..(1)
<223> OTHER INFORMATION: Asp modified by attachment to aminohexanoic
      acid (aminocaproic acid)

<400> SEQUENCE: 20

Asp Pro Arg Ser Phe Leu
1               5

<210> SEQ ID NO 21
<211> LENGTH: 7
<212> TYPE: PRT
<213> ORGANISM: Artificial Sequence
```

```
<220> FEATURE:
<223> OTHER INFORMATION: cleavable peptide
<220> FEATURE:
<221> NAME/KEY: MISC_FEATURE
<222> LOCATION: (1)..(1)
<223> OTHER INFORMATION: Asp modified by attachment to PEG-2

<400> SEQUENCE: 21

Xaa Asp Pro Arg Ser Phe Leu
1               5

<210> SEQ ID NO 22
<211> LENGTH: 5
<212> TYPE: PRT
<213> ORGANISM: Artificial Sequence
<220> FEATURE:
<223> OTHER INFORMATION: cleavable linker

<400> SEQUENCE: 22

Pro Arg Ser Phe Leu
1               5
```

PEPTIDES WHOSE UPTAKE IN CELLS IS CONTROLLABLE

CROSS-REFERENCE

This application is the National Stage of International Application No. PCT/US2010/042188, filed Jul. 15, 2010, which claims the benefit of U.S. Provisional Application No. 61/225,872, filed Jul. 15, 2009, which applications are incorporated herein by reference in its entirety.

STATEMENT AS TO FEDERALLY SPONSORED RESEARCH

This invention was made with governmental support under grant no. W81XWH-05-1-0183 awarded by the US Army Department of Defense, and grant no. NIBIB-K08 EB008122 awarded by the NIH. The government has certain rights in the invention.

BACKGROUND OF THE INVENTION

Cell membranes delimit the outer boundaries of cells, and regulate transport into and out of the cell interior. Made primarily of lipids and proteins, they provide a hydrophilic surface enclosing a hydrophobic interior across which materials must pass before entering a cell. Although many small, lipophilic compounds are able to cross cell membranes passively, most compounds, particles and materials must rely on active mechanisms in order to gain entry into a living cell.

SUMMARY OF THE INVENTION

Disclosed herein, in certain embodiments, is a molecule for imaging thrombin activity in a subject, wherein the molecule has the formula: $(A-X-B-C)_n-M$, wherein
C is at least one imaging agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a thrombin cleavable linker;
M is a macromolecular carrier; and
n is an integer between 1 and 20; and
wherein M is bound to A or B.
In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, the X is selected from: DPRSFL (SEQ ID NO: 1), or PPRSFL (SEQ ID NO: 2). In some embodiments, M is a macromolecular carrier selected from: a dendrimer, dextran, a PEG polymer, albumin, or lipid-coated perfluorocarbon droplet. In some embodiments, M is a PEG polymer. In some embodiments, the imaging agent is selected from: a fluorescent moiety, a luminescent moiety, a phosphorescent moiety, a fluorescence-quenching moiety, a radioactive moiety, a radiopaque moiety, a paramagnetic moiety, a contrast agent, ultrasound scatterer, or a combination thereof. In some embodiments, the imaging agent is selected from an indocarbocyanine dye. In some embodiments, the imaging agent is selected from Cy5, Cy5.5, Cy7, Alexa 647, IRDYE 800CW, or a combination thereof. In some embodiments, the imaging agent is an MRI contrast agent. In some embodiments, the imaging agent is Gd complex of [4,7,10-tris(carboxymethyl)-1,4,7,10-tetraazacyclododec-1-yl]acetyl.

Disclosed herein, in certain embodiments, is a method of imaging thrombin activity in a subject, comprising imaging thrombin activity after the subject has been administered a molecule of the structure $(A-X-B-C)_n-M$, wherein
C is at least one imaging agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a thrombin cleavable linker;
M is a macromolecular carrier;
n is an integer between 1 and 20; and
wherein M is bound to A or B.
In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, the X is selected from: DPRSFL (SEQ ID NO: 1), or PPRSFL (SEQ ID NO: 2). In some embodiments, M is a macromolecular carrier selected from: a dendrimer, dextran, a PEG polymer, albumin, or lipid-coated perfluorocarbon droplet. In some embodiments, M is a PEG polymer. In some embodiments, the imaging agent is selected from: a fluorescent moiety, a luminescent moiety, a phosphorescent moiety, a fluorescence-quenching moiety, a radioactive moiety, a radiopaque moiety, a paramagnetic moiety, a contrast agent, ultrasound scatterer, or a combination thereof. In some embodiments, the imaging agent is selected from an indocarbocyanine dye. In some embodiments, the imaging agent is selected from Cy5, Cy5.5, Cy7, Alexa 647, IRDYE 800CW, or a combination thereof. In some embodiments, the imaging agent is an MRI contrast agent. In some embodiments, the imaging agent is Gd complex of [4,7,10-tris(carboxymethyl)-1,4,7,10-tetraazacyclododec-1-yl]acetyl.

Disclosed herein, in certain embodiments, is a use of a molecule to of structure $(A-X-B-C)_n-M$ for visualizing thrombin activity in a subject in need thereof, wherein
C is at least one imaging agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a thrombin cleavable linker;
M is a macromolecular carrier; and
n is an integer between 1 and 20; and
wherein M is bound to A or B.

In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, the X is selected from: DPRSFL (SEQ ID NO: 1), or PPRSFL (SEQ ID NO: 2). In some embodiments, M is a macromolecular carrier selected from: a dendrimer, dextran, a PEG polymer, albumin, or lipid-coated perfluorocarbon droplet. In some embodiments, M is a PEG polymer. In some embodiments, the imaging agent is selected from: a fluorescent moiety, a luminescent moiety, a phosphorescent moiety, a fluorescence-quenching moiety, a radioactive moiety, a radiopaque moiety, a paramagnetic moiety, a contrast agent, ultrasound scatterer, or a combination thereof. In some embodiments, the imaging agent is selected from an indocarbocyanine dye. In some embodiments, the imaging agent is selected from Cy5, Cy5.5, Cy7, Alexa 647, IRDYE 800CW, or a combination thereof. In some embodiments, the imaging agent is an MRI contrast agent. In some embodiments, the imaging agent is Gd complex of [4,7,10-tris(carboxymethyl)-1,4,7,10-tetraazacyclododec-1-yl]acetyl.

Disclosed herein, in certain embodiments, is a method of characterizing the risk associated with an atherosclerotic plaque in a subject, comprising imaging thrombin activity in the atherosclerotic plaque after the subject has been administered a molecule of the structure $(A-X-B-C)_n-M$, C is at least one imaging agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a thrombin cleavable linker;
M is a macromolecular carrier;
n is an integer between 1 and 20; and
wherein M is bound to A or B; and
wherein the risk is proportional to the imaging agent signal intensity.

In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, the X is selected from: DPRSFL (SEQ ID NO: 1), or PPRSFL (SEQ ID NO: 2). In some embodiments, M is a macromolecular carrier selected from: a dendrimer, dextran, a PEG polymer, albumin, or lipid-coated perfluorocarbon droplet. In some embodiments, M is a PEG polymer. In some embodiments, the imaging agent is selected from: a fluorescent moiety, a luminescent moiety, a phosphorescent moiety, a fluorescence-quenching moiety, a radioactive moiety, a radiopaque moiety, a paramagnetic moiety, a contrast agent, ultrasound scatterer, or a combination thereof. In some embodiments, the imaging agent is selected from an indocarbocyanine dye. In some embodiments, the imaging agent is selected from Cy5, Cy5.5, Cy7, Alexa 647, IRDYE 800CW, or a combination thereof. In some embodiments, the imaging agent is an MRI contrast agent. In some embodiments, the imaging agent is Gd complex of [4,7,10-tris(carboxymethyl)-1,4,7,10-tetraazacyclododec-1-yl]acetyl.

Disclosed herein, in certain embodiments, is a use of a molecule of the structure $(A-X-B-C)_n-M$ to characterize the risk associated with an atherosclerotic plaque in a subject, wherein C is at least one imaging agent;
B is a peptide with a sequence comprising 5 to 20 consecutive basic amino acids;
X is a thrombin cleavable linker;
M is a macromolecular carrier;
n is an integer between 1 and 20; and
wherein M is bound to A or B; and
wherein the risk is proportional to the imaging agent signal intensity.

In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, the X is selected from: DPRSFL (SEQ ID NO: 1), or PPRSFL (SEQ ID NO: 2). In some embodiments, M is a macromolecular carrier selected from: a dendrimer, dextran, a PEG polymer, albumin, or lipid-coated perfluorocarbon droplet. In some embodiments, M is a PEG polymer. In some embodiments, the imaging agent is selected from: a fluorescent moiety, a luminescent moiety, a phosphorescent moiety, a fluorescence-quenching moiety, a radioactive moiety, a radiopaque moiety, a paramagnetic moiety, a contrast agent, ultrasound scatterer, or a combination thereof. In some embodiments, the imaging agent is selected from an indocarbocyanine dye. In some embodiments, the imaging agent is selected from Cy5, Cy5.5, Cy7, Alexa 647, IRDYE 800CW, or a combination thereof. In some embodiments, the imaging agent is an MRI contrast agent. In some embodiments, the imaging agent is Gd complex of [4,7,10-tris(carboxymethyl)-1,4,7,10-tetraazacyclododec-1-yl]acetyl.

Disclosed herein, in certain embodiments, is a method of treating a cardiovascular disorder characterized by an increase in thrombin activity as compared to a subject without the cardiovascular disorder, comprising administering to the subject a molecule of the structure $(A-X-B-C)_n-M$, C is at least one therapeutic agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;

X is a thrombin cleavable linker;
M is a macromolecular carrier;
n is an integer between 1 and 20; and
wherein M is bound to A or B.

In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, the X is selected from: DPRSFL (SEQ ID NO: 1), or PPRSFL (SEQ ID NO: 2). In some embodiments, M is a macromolecular carrier selected from: a dendrimer, dextran, a PEG polymer, albumin, or lipid-coated perfluorocarbon droplet. In some embodiments, M is a PEG polymer. In some embodiments, the therapeutic agent is an HDL-raising therapy, a Glycoprotein (GP) IIb/IIIa receptor antagonist, a P2Y12 receptor antagonist, a Lp-PLA2-inhibitor, a leukotriene inhibitor, a MIF antagonist, or a combination thereof. In some embodiments, the therapeutic agent is: a niacin, a fibrate, a statin, an Apo-A1 mimetic peptide, an apoA-I transcriptional up-regulator, an ACAT inhibitor, a CETP modulator, or a combination thereof. In some embodiments, the therapeutic agent is: atorvastatin; cerivastatin; fluvastatin; lovastatin; mevastatin; pitavastatin; pravastatin; rosuvastatin; simvastatin; simvastatin and ezetimibe; lovastatin and niacin, extended-release; atorvastatin and amlodipine besylate; simvastatin and niacin, extended-release; bezafibrate; ciprofibrate; clofibrate; gemfibrozil; fenofibrate; DF4 (Ac-D-W-F-K-A-F-Y-D-K-V-A-E-K-F-K-E-A-F-NH2 (SEQ ID NO: 3)); DFS; RVX-208 (Resverlogix); avasimibe; pactimibe sulfate (CS-505); CI-1011 (2,6-diisopropylphenyl [(2, 4,6-triisopropylphenylacetyl]sulfamate); CI-976 (2,2-dimethyl-N-(2,4,6-trimethoxyphenyl)dodecanamide); VULM1457 (1-(2,6-diisopropyl-phenyl)-3-[4-(4'-nitrophenylthio)phenyl] urea); CI-976 (2,2-dimethyl-N-(2,4,6-trimethoxyphenyl)dodecanamide); E-5324 (n-butyl-N'-(2-(3-(5-ethyl-4-phenyl-1H-imidazol-1-yl)propoxy)-6-methylphenyl)urea); HL-004 (N-(2,6-diisopropylphenyl)tetradecylthioacetamide); KY-455 (N-(4,6-dimethyl-1-pentylindolin-7-yl)-2,2-dimethylpropanamide); FY-087 (N-[2-[N'-pentyl-(6,6-dimethyl-2,4-heptadiynyl)amino]ethyl]-(2-methyl-1-naphthyl-thio)acetamide); MCC-147 (Mitsubishi Pharma); F 12511 ((S)-2',3',5'-trimethyl-4'-hydroxy-alpha-dodecylthioacetanilide); SMP-500 (Sumitomo Pharmaceuticals); CL 277082 (2,4-difluoro-phenyl-N[[4-(2,2-dimethylpropylphenyl]methyl]-N-(hepthyl]urea); F-1394 ((1s,2s)-2-[3-(2,2-dimethylpropyl)-3-nonylureido]aminocyclohexane-1-yl 3-[N-(2,2,5,5-tetramethyl-1,3-dioxane-4-carbonyl)amino]propionate); CP-113818 (N-(2, 4-bis(methylthio)-6-methylpyridin-3-yl)-2-(hexylthio) decanoic acid amide); YM-750; torcetrapib; anacetrapid; JTT-705 (Japan Tobacco/Roche); abciximab; eptifibatide; tirofiban; roxifiban; variabilin; XV 459 (N(3)-(2-(3-(4-formamidinophenyl)isoxazolin-5-yl)acetyl)-N(2)-(1-butyloxycarbonyl)-2,3-diaminopropionate); SR 121566A (3-[N-{4-[4-(aminoiminomethyl)phenyl]-1,3-thiazol-2-yl}-N-(1-carboxymethylpiperid-4-yl) aminol propionic acid, trihydrochloride); FK419 ((S)-2-acetylamino-3-[(R)-[1-[3-(piperidin-4-yl) propionyl] piperidin-3-ylcarbonyl] amino] propionic acid trihydrate); clopidogrel; prasugrel; cangrelor; AZD6140 (AstraZeneca); MRS 2395 (2,2-Dimethyl-propionic acid 3-(2-chloro-6-methylaminopurin-9-yl)-2-(2,2-dimethyl-propionyloxymethyl)-propyl ester); BX 667 (Berlex Biosciences); BX 048 (Berlex Biosciences); darapladib (SB 480848); SB-435495 (GlaxoSmithKline); SB-222657 (GlaxoSmithKline); SB-253514 (GlaxoSmithKline); A-81834 (3-(3-(1,1-dimethylethylthio-5-(quinoline-2-yl-methoxy)-1-(4-chloromethylphenyl)indole-2-yl)-2,2-dimethylpropionaldehyde oxime-O-2-acetic acid; AME103 (Amira); AME803 (Amira); atreleuton; BAY-x-1005 ((R)-(+)-alpha-cyclopentyl-4-(2-quinolinylmethoxy)-Benzeneacetic acid); CJ-13610 (4-(3-(4-(2-Methyl-imidazol-1-yl]-phenylsulfanyl)-phenyl)-tetrahydro-pyran-4-carboxylic acid amide); DG-031 (DeCode); DG-051 (DeCode); MK886 (1-[(4-chlorophenylmethyl]3-[(1,1-dimethylethyl)thio]-α,α-dimethyl-5-(1-methylethyl)-1H-indole-2-propanoic acid, sodium salt); MK591 (3-(1-4[(4-chlorophenyl)methyl]-3-[(t-butylthio)-5-((2-quinoly)methoxy)-1H-indole-2]-, dimehtylpropanoic acid); RP64966 ([4-[5-(3-Phenyl-propyl)thiophen-2-yl]butoxy] acetic acid); SA6541 ((R)-S-[[4-(dimethylamino)phenyl]methyl]-N-(3-mercapto-2methyl-1-oxopropyl-L-cycteine); SC-56938 (ethyl-1-[2-[4-(phenylmethyl)phenoxy] ethyl]-4-piperidine-carboxylate); VIA-2291 (Via Pharmaceuticals); WY-47,288 (2-[(1-naphthalenyloxy)methyl]quinoline); zileuton; ZD-2138 (6-((3-fluoro-5-(tetrahydro-4-methoxy-2H-pyran-4yl) phenoxy)methyl)-1-methyl-2(1H)-quinlolinone); or combinations thereof. In some embodiments, C further comprises at least one imaging agent. In some embodiments, C further comprises: a fluorescent moiety, a luminescent moiety, a phosphorescent moiety, a fluorescence-quenching moiety, a radioactive moiety, a radiopaque moiety, a paramagnetic moiety, a contrast agent, ultrasound scatterer, or a combination thereof. In some embodiments, C further comprises an indocarbocyanine dye. In some embodiments, C further comprises: Cy5, Cy5.5, Cy7, Alexa 647, IRDYE 800CW, or a combination thereof. In some embodiments, C further comprises an MRI contrast agent. In some embodiments, C further comprises Gd complex of [4,7,10-tris (carboxymethyl)-1,4,7,10-tetraazacyclododec-1-yl]acetyl.

Disclosed herein, in certain embodiments, is a use of a molecule of the structure $(A-X-B-C)_n-M$ to treat a cardiovascular disorder characterized by an increase in thrombin activity as compared to a subject without the cardiovascular disorder, wherein
C is at least one therapeutic agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a thrombin cleavable linker;
M is a macromolecular carrier;
n is an integer between 1 and 20; and
wherein M is bound to A or B.

In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, the X is selected from: DPRSFL (SEQ ID NO: 1), or PPRSFL (SEQ ID NO: 2). In some embodiments, M is a macromolecular carrier selected from: a dendrimer, dextran, a PEG polymer, albumin, or lipid-coated perfluorocarbon droplet. In some embodiments, M is a PEG polymer. In some embodiments, the therapeutic agent is an HDL-raising therapy, a Glycoprotein (GP) Hb/IIIa receptor antagonist, a P2Y12 receptor antagonist, a Lp-PLA2-inhibitor, a leukotriene inhibitor, a MIF antagonist, or a combination thereof. In some embodiments, the therapeutic agent is: a niacin, a fibrate, a statin, an Apo-A1 mimetic peptide, an apoA-I transcriptional up-regulator, an ACAT inhibitor, a CETP modulator, or a combination thereof. In some embodiments, the therapeutic agent is: atorvastatin; cerivastatin; fluvastatin; lovastatin; mevastatin; pitavastatin; pravastatin; rosuvastatin; simvastatin; simvastatin and ezetimibe; lovastatin and niacin, extended-release; atorvastatin and amlodipine besylate; simvastatin and niacin, extended-release; bezafibrate; ciprofibrate; clofibrate; gemfibrozil; fenofibrate; DF4 (Ac-D-W-F-K-A-F-Y-D-K-V-A-E-K-F-K-E-A-F-NH2 (SEQ ID NO: 3)); DFS; RVX-208 (Resverlogix); avasimibe; pactimibe sulfate (CS-505); CI-1011 (2,6-diisopropylphenyl [(2, 4,6-triisopropylphenyl)acetyl]sulfamate); CI-976 (2,2-dimethyl-N-(2,4,6-trimethoxyphenyl)dodecanamide); VULM1457 (1-(2,6-diisopropyl-phenyl)-3-[4-(4'-nitrophenylthio)phenyl] urea); CI-976 (2,2-dimethyl-N-(2,4,6-trimethoxyphenyl)dodecanamide); E-5324 (n-butyl-N'-(2-(3-(5-ethyl-4-phenyl-1H-imidazol-1-yl)propoxy)-6-methylphenyl)urea); HL-004 (N-(2,6-diisopropylphenyl) tetradecylthioacetamide); KY-455 (N-(4,6-dimethyl-1-pentylindolin-7-yl)-2,2-dimethylpropanamide); FY-087 (N-[2-[N'-pentyl-(6,6-dimethyl-2,4-heptadiynylamino]ethyl]-(2-methyl-1-naphthyl-thio)acetamide); MCC-147 (Mitsubishi Pharma); F 12511 ((S)-2',3',5'-trimethyl-4'-hydroxy-alpha-dodecylthioacetanilide); SMP-500 (Sumitomo Pharmaceuticals); CL 277082 (2,4-difluoro-phenyl-N[[4-(2,2-dimethylpropyl)phenyl]methyl]-N-(hepthyl)urea); F-1394 ((1 s,2s)-2-[3-(2,2-dimethylpropyl)-3-nonylureido]aminocyclohexane-1-yl 3-[N-(2,2,5,5-tetramethyl-1,3-dioxane-4-carbonyl)amino]propionate); CP-113818 (N-(2,4-bis(methylthio)-6-methylpyridin-3-yl)-2-(hexylthio)decanoic acid amide); YM-750; torcetrapib; anacetrapid; JTT-705 (Japan Tobacco/Roche); abciximab; eptifibatide; tirofiban; roxifiban; variabilin; XV 459 (N(3)-(2-(3-(4-formamidinophenyl)isoxazolin-5-yl)acetyl)-N(2)-(1-butyloxycarbonyl)-2,3-diaminopropionate); SR 121566A (3-[N-{-4-[4-(aminoiminomethyl)phenyl]-1,3-thiazol-2-yl}-N-(1-carboxymethylpiperid-4-yl) aminol propionic acid, trihydrochloride); FK419 ((S)-2-acetylamino-3-[(R)-[1-[3-(piperidin-4-yl) propionyl] piperidin-3-ylcarbonyl] amino] propionic acid trihydrate); clopidogrel; prasugrel; cangrelor; AZD6140 (AstraZeneca); MRS 2395 (2,2-Dimethyl-propionic acid 3-(2-chloro-6-methylaminopurin-9-yl)-2-(2,2-dimethyl-propionyloxymethyl)-propyl ester); BX 667 (Berlex Biosciences); BX 048 (Berlex Biosciences); darapladib (SB 480848); SB-435495 (GlaxoSmithKline); SB-222657 (GlaxoSmithKline); SB-253514 (GlaxoSmithKline); A-81834 (3-(3-(1,1-dimethylethylthio-5-(quinoline-2-yl-methoxy)-1-(4-chloromethylphenyl)indole-2-yl)-2,2-dimethylpropionaldehyde oxime-O-2-acetic acid; AME103 (Amira); AME803 (Amira); atreleuton; BAY-x-1005 ((R)-(+)-alpha-cyclopentyl-4-(2-quinolinylmethoxy)-Benzeneacetic acid); CJ-13610 (4-(3-(4-(2-Methyl-imidazol-1-yl)-phenylsulfanyl)-phenyl)-tetrahydro-pyran-4-carboxylic acid amide); DG-031 (DeCode); DG-051 (DeCode); MK886 (1-[(4-chlorophenyl]methyl]3-[(1,1-dimethylethyl) thio]-α,α-dimethyl-5-(1-methylethyl)-1H-indole-2-propanoic acid, sodium salt); MK591 (3-(1-4[(4-chlorophenyl) methyl]-3-[(t-butylthio)-5-((2-quinoly)methoxy)-1H-indole-2]-, dimehtylpropanoic acid); RP64966 ([4-[5-(3-Phenyl-propyl)thiophen-2-yl]butoxy] acetic acid); SA6541 ((R)-S-[[4-(dimethylamino)phenyl]methyl]-N-(3-mercapto-2methyl-1-oxopropyl-L-cycteine); SC-56938 (ethyl-l-[2-[4-(phenylmethyl)phenoxy] ethyl]-4-piperidine-carboxylate); VIA-2291 (Via Pharmaceuticals); WY-47,288 (2-[(1-naphthalenyloxy)methyl]quinoline); zileuton; ZD-2138 (6-((3-fluoro-5-(tetrahydro-4-methoxy-2H-pyran-4yl)phenoxy) methyl)-1-methyl-2(1H)-quinlolinone); or combinations thereof. In some embodiments, C further comprises at least one imaging agent. In some embodiments, C further comprises: a fluorescent moiety, a luminescent moiety, a phosphorescent moiety, a fluorescence-quenching moiety, a radioactive moiety, a radiopaque moiety, a paramagnetic moiety, a contrast agent, ultrasound scatterer, or a combination thereof. In some embodiments, C further comprises an idocarbocyanine dye. In some embodiments, C further comprises: Cy5, Cy5.5, Cy7, Alexa 647, IRDYE 800CW, or a combination thereof. In some embodiments, C further comprises an MRI contrast agent. In some embodiments, C further comprises Gd complex of [4,7,10-tris(carboxymethyl)-1,4,7,10-tetraazacyclododec-1-yl] acetyl.

Disclosed herein, in certain embodiments, is an image of thrombin activity, wherein the image is generated by imaging thrombin activity after the subject has been administered a molecule of the structure $(A-X-B-C)_n-M$, wherein C is at least one imaging agent;
A is a peptide with a sequence comprising 5 to 9 consecutive acidic amino acids, wherein the amino acids are selected from: aspartates and glutamates;
B is a peptide with a sequence comprising 5 to 20 consecutive basic amino acids;
X is a thrombin cleavable linker;
M is a macromolecular carrier;
n is an integer between 1 and 20; and
wherein M is bound to A or B.

In some embodiments, the image is stored in analogue form or digital form. In some embodiments, the image is stored as a photograph. In some embodiments, the image is stored on a computer readable medium. In some embodiments, A has a sequence comprising 5 to 9 consecutive glutamates. In some embodiments, B has a sequence comprising 5 to 12 consecutive arginines. In some embodiments, B has a sequence comprising 9 consecutive arginines. In some embodiments, (a) A has a sequence comprising 8 to 9 consecutive glutamates and (b) B has a sequence comprising 9 consecutive arginines. In some embodiments, A and B comprise D-amino acids. In some embodiments, X comprises a peptide linkage. In some embodiments, X comprises 6-aminohexanoyl, 5-amino-3-oxapentanoyl, or a combination thereof. In some embodiments, X comprises a disulfide linkage. In some embodiments, X is about 6 to about 30 atoms in length. In some embodiments, the X is selected from: DPRSFL (SEQ ID NO: 1), or PPRSFL (SEQ ID NO: 2). In some embodiments, M is a macromolecular carrier selected from: a dendrimer, dextran, a PEG polymer, albumin, or lipid-coated perfluorocarbon droplet. In some embodiments, M is a PEG polymer. In some embodiments, the imaging agent is selected from: a fluorescent moiety, a luminescent moiety, a phosphorescent moiety, a fluorescence-quenching moiety, a radioactive moiety, a radiopaque moiety, a paramagnetic moiety, a contrast agent, ultrasound scatterer, or a combination thereof. In some embodiments, the imaging agent is selected from an indocarbocyanine dye. In some embodiments, the imaging agent is selected from Cy5, Cy5.5, Cy7, Alexa 647, IRDYE 800CW, or a combination thereof. In some embodiments, the imaging agent is an MRI contrast agent. In some embodiments, the imaging agent is Gd complex of [4,7,10-tris(carboxymethyl)-1,4,7, 10-tetraazacyclododec-1-yl]acetyl.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3. PPRSFL-Cy5 (SEQ ID NO: 5) labels the adult mouse brain after experimental stroke. Injured vasculature on the base of an adult mouse brain after transient unilateral occlusion of the internal carotid artery with a nylon filament is labeled with PPRSFL-Cy5 (SEQ ID NO: 5). (Similar focal accumulations of DPRSFL (SEQ ID NO: 1) fluorescence have been observed with this filament-artery occlusion model of stroke in the adult rat.) Left panel illustrates the base of a mouse brain after a 2 hour stroke from transient blockage of the internal carotid artery with a withdrawable nylon filament. PPRSFL-Cy5 (SEQ ID NO: 5) was injected at the start of the 6 hour reperfusion period. Cy5 fluorescence concentrates with the injured artery and also at a second site situated in the brain parenchyma near the base of the ostium of the middle cerebral artery. Middle panel shows a view of the base of the brain where the fluorescence is inverted (and appears as a dark signal). Right panel is illustrates vascular injury from this filament occlusion to verify an ischemic stroke. In this case the filament occlusion appears to have caused a hemorrhage and blood efflux onto the surface of the brain.

DETAILED DESCRIPTION OF THE INVENTION

Figure 1:
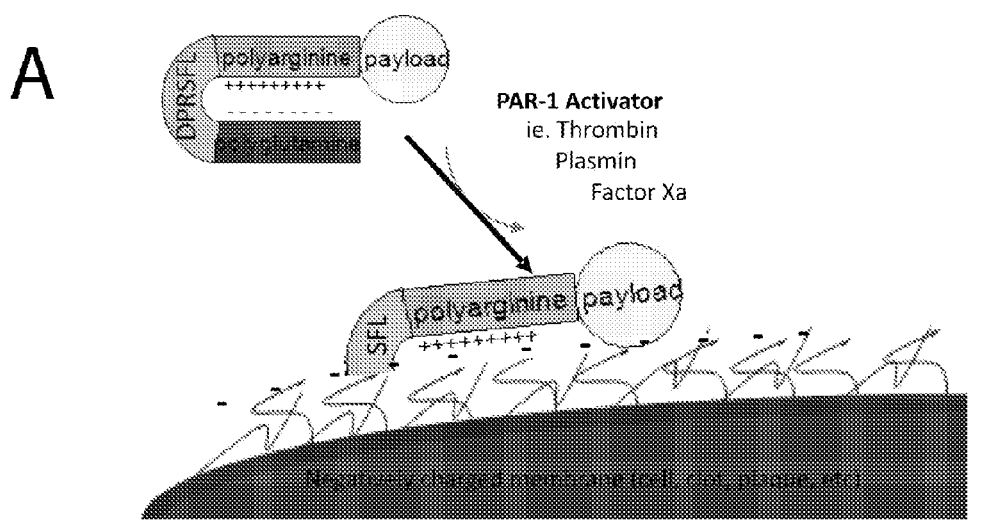
FIG. 1. DPRSFL (SEQ ID NO: 1)-based transport molecule is cleaved by purified thrombin and by clot-generated thrombin. A: Schematic of a selective transport molecule showing a positively charged polyarginine separated from a negatively charged polyglutamine by a protease cleavable linker. Once the linker is cleaved, the polyarginine is free to associate with negatively charged membranes on cells, clots or plaques. B: Representative polyacrylamide gel showing cleavage of the DPRSFL (SEQ ID NO: 1)-based transport molecule by 50 nM thrombin (dark grey) or 50% serum (light grey) after 20 minutes incubation. Direct thrombin inhibitors were able to completely inhibit cleavage of selective transport molecule. Experiments were done in triplicate. C: Representative polyacrylamide gel showing cleavage of DPRSFL (SEQ ID NO: 1)-based transport molecule by several enzymes known to cleave the PAR-1 receptor including trypsin, chymotrypsin, thrombin, plasmin and factor Xa after one hour incubation in 50 nmol enzyme. Experiments were done in triplicate.
Figure 1:
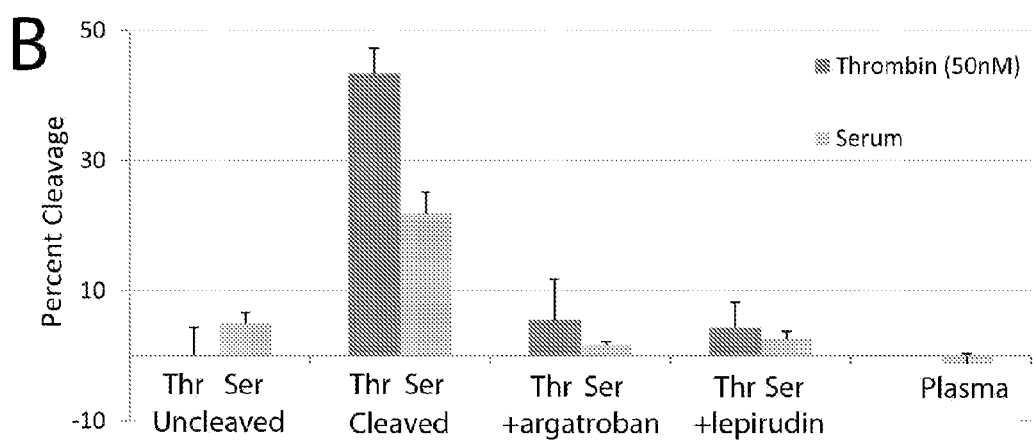
Figure 1:
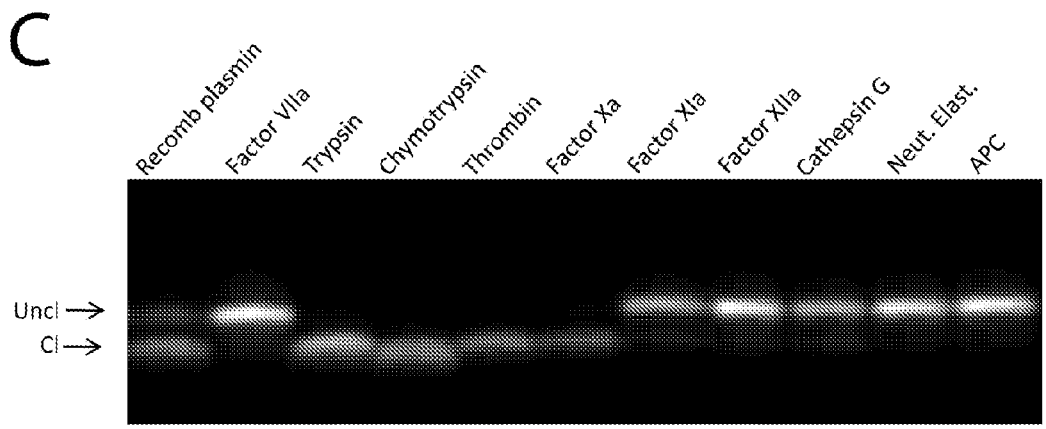

Disclosed herein, in certain embodiments, is a selective transport molecule.

In some embodiments, a selective transport molecule disclosed herein has the formula A-X-B-C, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker that is cleavable by thrombin.

In some embodiments, a selective transport molecule disclosed herein has the formula (A-X-B-C)$_n$-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; and M is a macromolecular carrier.

Certain Definitions

The following terms have the meanings ascribed to them unless specified otherwise.

The terms cell penetrating peptide (CPP), membrane translocating sequence (MTS) and protein transduction domain are used interchangeably. As used herein, the terms mean a peptide (polypeptide or protein) sequence that is able to translocate across the plasma membrane of a cell. In some embodiments, a CPP facilitates the translocation of an extracellular molecule across the plasma membrane of a cell. In some embodiments, the CPP translocates across the plasma membrane by direct penetration of the plasma membrane, endocytosis-mediated entry, or the formation of a transitory structure.

As used herein, the term "aptamer" refers to a DNA or RNA molecule that has been selected from random pools based on their ability to bind other molecules with high affinity specificity based on non-Watson and Crick interactions with the target molecule (see, e.g., Cox and Ellington, Bioorg. Med. Chem. 9:2525-2531 (2001); Lee et al., Nuc. Acids Res. 32:D95-D100 (2004)). In some embodiments, the aptamer binds nucleic acids, proteins, small organic compounds, vitamins, inorganic compounds, cells, and even entire organisms.

The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the terms "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an a-ester, a 13-ester, a thioamide, phosphonamide, carbamate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be either D amino acids or L amino acids. In peptide sequences throughout the specification, lower case letters indicate the D isomer of the amino acid (conversely, upper case letters indicate the L isomer of the amino acid).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

As used herein, a "linker" is any molecule capable of binding (e.g., covalently) portion A and portion B of a selective transport molecule disclosed herein. Linkers include, but are not limited to, straight or branched chain carbon linkers, heterocyclic carbon linkers, peptide linkers, and polyether linkers. For example, poly(ethylene glycol) linkers are available from Quanta Biodesign, Powell, Ohio. These linkers optionally have amide linkages, sulfhydryl linkages, or heterofunctional linkages.

As used herein, the term "label" refers to any molecule that facilitates the visualization and/or detection of a selective transport molecule disclosed herein. In some embodiments, the label is a fluorescent moiety.

The term "carrier" means an inert molecule that increases (a) plasma half-life and (b) solubility. In some embodiments, a carrier increases plasma half-life and solubility by reducing glomerular filtration. In some embodiments, a carrier increases tumor uptake due to enhanced permeability and retention (EPR) of tumor vasculature.

The term "thrombin" means an enzyme (EC 3.4.21.5) that cleaves fibrinogen molecules into fibrin monomers. Thrombin, acting through its G-protein coupled receptor PAR-1, is a key player in a wide range of vascular and extravascular disease processes throughout the body, including cancer, cardiovascular diseases, acute kidney injury, and stroke. In certain instances, thrombin activity increases over the course of atherosclerotic plaque development. In some embodiments, thrombin activity is a biomarker for atherosclerotic plaque development.

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

As used herein, the term "medical professional" means any health care worker. By way of non-limiting example, the health care worker may be a doctor, a registered nurse, a nurse practitioner, a physician's assistant, an orderly, or a hospice worker.

The terms "administer," "administering", "administration," and the like, as used herein, refer to the methods that may be used to enable delivery of agents or compositions to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "surgery" as used herein, refers to any methods for that may be used to manipulate, change, or cause an effect by a physical intervention. These methods include, but are not limited to open surgery, endoscopic surgery, laparoscopic surgery, minimally invasive surgery, and robotic surgery The following symbols, where used, are used with the indicated meanings: Fl=fluorescein; aca=ahx=X=aminohexanoyl linker (—HN—((CH$_2$)$_5$—CO-)aminohexanoyl; C=L-cysteine; E=L-glutamate; R=L-arginine; D=L-aspartate; K=L-lysine; A=L-alanine; r=D-arginine; c=D-cysteine; e=D-glutamate; P=L-proline; L=L-leucine; G=glycine; V=valine; I=isoleucine; M=methionine; F=phenylalanine; Y=tyrosine; W=tryptophan; H=histidine; Q=glutamine; N=asparagine; S=serine; T=threonine, o is 5-amino-3-oxapentanoyl linker, and C(me) is S-methylcysteine.

Selective Transport Molecules

Regulation of transport into and out of a cell is important for its continued viability. For example, cell membranes contain ion channels, pumps, and exchangers capable of facilitating the transmembrane passage of many important substances. However, transmembrane transport is selective: in addition to facilitating the entry of desired substances into a cell, and facilitating the exit of others, a major role of a cell membrane is to prevent uncontrolled entry of substances into the cell interior. This barrier function of the cell membrane makes difficult the delivery of markers, drugs, nucleic acids, and other exogenous material into cells.

Multiple membrane translocation signals (MTS) have been identified. For example, the Tat protein of the human immunodeficiency virus 1 (HIV-1) is able to enter cells from the extracellular environment. A domain from Antennapedia homeobox protein is also able to enter cells.

Molecules comprising a MTS may also be used to carry other molecules into cells along with them. The most important MTS are rich in amino acids such as arginine with positively charged side chains. Molecules transported into cell by such cationic peptides may be termed "cargo" and may be reversibly or irreversibly linked to the cationic peptides.

The uptake facilitated by molecules comprising a MTS is currently without specificity, enhancing uptake into most or all cells. It is desirable to have the ability to target the delivery of cargo to a type of cell, or to a tissue, or to a location or region within the body of an animal. Accordingly, we have identified a need for a selective transport molecule with increased in vivo circulation.

In some embodiments, a selective transport molecule disclosed herein has the formula A-X-B-C, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker that is cleavable by thrombin.

In some embodiments, a selective transport molecule disclosed herein has the formula $(A-X-B-C)_n$-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; M is a macromolecular carrier; and n is an integer between 1 and 20.

In some embodiments, a selective transport molecule disclosed herein has the formula $(A-X-B)_n$-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; D is a dendrimer; and n is an integer between 1 and 20. In some embodiments, D comprises a cargo moiety.

In embodiments, a selective transport molecule disclosed herein is a linear molecule. In embodiments, a selective transport molecule disclosed herein is a cyclic molecule, as schematically illustrated in FIG. 1B. In embodiments, a selective transport molecule disclosed herein comprises a cyclic portion and a linear portion.

A selective transport molecule disclosed herein may be of any length. In some embodiments, a selective transport molecule disclosed herein is about 7 to about 40 amino acids in length, not including the length of a linker X and a cargo moiety C. In other embodiments, particularly where multiple non-acidic (in portion A) or non-basic (in portion B) amino acids are included in one or both of portions A and B, portions A and B of a selective transport molecule disclosed herein may together be about 50, or about 60, or about 70 amino acids in length. A cyclic portion of a selective transport molecule disclosed herein may include about 12 to about 60 amino acids, not including the length of a linker X and a cargo moiety C. For example, a linear selective transport molecule disclosed herein may have a basic portion B having between about 5 to about 20 basic amino acids (preferably between about 9 to about 16 basic amino acids) and an acidic portion A having between about 2 to about 20 acidic amino acids (e.g., between about 5 to about 20, preferably between about 5 to about 9 acidic amino acids). In some preferred embodiments, a selective transport molecule disclosed herein may have a basic portion B having between about 9 to about 16 basic amino acids and between about 5 to about 9 acidic amino acids. In some embodiments, A is 8 consecutive glutamates (i.e., EEEEEEEE, $E_9$, eeeeeeee, or e9), B is nine consecutive arginines (i.e., RRRRRRRRR, $R_9$, rrrrrrrrr, or r9), and X is PLGLAG.

In some embodiments, the selective transport molecule is selected from: Suc-$e_9$-XDPRSFL-$r_9$-c(Cy5)-$CONH_2$; Suc-$e_9$-ODPRSFL-$r_9$-c(Cy5)-$CONH_2$; and Suc-$e_9$-Xdprsfl-$r_9$-c(Cy5)-$CONH_9$.

Peptide Synthesis

A selective transport molecule disclosed herein is synthesized by any suitable method, such as, for example, solid phase synthesis including solid phase peptide synthesis. An example of peptide synthesis using Fmoc is given as Example 1 below. For example, conventional solid phase methods for synthesizing peptides may start with N-alpha-protected amino acid anhydrides that are prepared in crystallized form or prepared freshly in solution, and are used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1 to 2 reaction cycles are used for the first twelve residue additions, and 2 to 3 reaction cycles for the remaining residues.

After completing the growing peptide chains, the protected peptide resin is treated with a strong acid such as liquid hydrofluoric acid or trifluoroacetic acid to deblock and release the peptides from the support. For preparing an amidated peptide, the resin support used in the synthesis is selected to supply a C-terminal amide, after peptide cleavage from the resin. After removal of the strong acid, the peptide may be extracted into 1M acetic acid solution and lyophilized. The peptide may be isolated by an initial separation by gel filtration, to remove peptide dimers and higher molecular weight polymers, and also to remove undesired salts The partially purified peptide may be further purified by preparative HPLC chromatography, and the purity and identity of the peptide confirmed by amino acid composition analysis, mass spectrometry and by analytical HPLC (e.g., in two different solvent systems).

Polynucleotide Synthesis

Disclosed herein, in certain embodiments is a polynucleotide encoding a selective transport molecule described herein. The term "polynucleotide" refers to a polymeric form of nucleotides of at least 10 bases in length. Nucleotides include ribonucleotides, deoxynucleotides, or modified forms of either type of nucleotide. The term includes single and double stranded forms of DNA. The term therefore includes, for example, a recombinant DNA which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

These polynucleotides include DNA, cDNA, and RNA sequences which encode a selective transport molecule described herein, or portions thereof. In some embodiments, polynucleotides include promoter and other sequences, and may be incorporated into a vector for transfection (which may be stable or transient) in a host cell.

The construction of expression vectors and the expression of genes in transfected cells involves the use of molecular cloning techniques that are well known in the art. See, for example, Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., most recent Supplement). Nucleic acids used to transfect cells with sequences coding for expression of the polypeptide of interest generally will be in the form of an expression vector including expression control sequences operatively linked to a nucleotide sequence coding for expression of the polypeptide. As used herein, "operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components that are able to influence expression, and also include additional components whose presence is advantageous, for example, leader sequences and fusion partner sequences. As used herein, the term "nucleotide sequence coding for expression or a polypeptide refers to a sequence that, upon transcription and translation of mRNA, produces the polypeptide. This includes sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Any suitable method is used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989). Transformation of a host cell with recombinant DNA may be carried out by conventional techniques as are well known to those skilled in the art.

Where the host is prokaryotic, such as E. coli, competent cells (i.e., cell which are capable of DNA uptake) are prepared from cells harvested after exponential growth phase and subsequently treated with $CaCl_2$, $MgCl_2$ or RbCl. In certain instances, transformation is performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in Liposomes, or virus vectors may be used. In certain instances, eukaryotic cells are co-transfected with DNA sequences encoding a molecule disclosed herein, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Techniques for the isolation and purification of polypeptides of the invention expressed in prokaryotes or eukaryotes may be by any conventional means such as, for example, preparative chromatographic separations and immunological separations such as those involving the use of monoclonal or polyclonal antibodies or antigen.

Portion A

Disclosed herein, in certain embodiments, is a selective transport molecule.

In some embodiments, a selective transport molecule disclosed herein has the formula A-X-B-C, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker that is cleavable by thrombin.

In some embodiments, a selective transport molecule disclosed herein has the formula $(A-X-B-C)_n$-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; M is a macromolecular carrier; and n is an integer between 1 and 20.

In some embodiments, a selective transport molecule disclosed herein has the formula $(A-X-B)_n$-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; D is a dendrimer; and n is an integer between 1 and 20. In some embodiments, D comprises a cargo moiety. See Example 1 for methods of attaching a label to a selective transport molecule.

In some embodiments of molecules having features of the invention, peptide portion A includes between about 2 to about 20, or between about 5 to about 20 acidic amino acids, and may be series of acidic amino acids (e.g., glutamates and aspartates or other acidic amino acids). In some embodiments, A has a sequence comprising 5 to 9 consecutive glutamates.

In some embodiments, portion A comprises 8 consecutive glutamates (i.e., EEEEEEEE or eeeeeeee).

An acidic portion A may include amino acids that are not acidic. Acidic portion A may comprise other moieties, such as negatively charged moieties. In embodiments of a selective transport molecule disclosed herein, an acidic portion A may be a negatively charged portion, preferably having about 2 to about 20 negative charges at physiological pH that does not include an amino acid. In preferred embodiments, the amount of negative charge in portion A is approximately the same as the amount of positive charge in portion B.

Portion A is either L-amino acids or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that portion A may include non-standard amino acids, such as, for example, hydroxylysine, desmosine, isodesmosine, or other non-standard amino acids. Portion A may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion A may also include peptide mimetic moieties, including portions linked by non-peptide bonds and amino acids linked by or to non-amino acid portions.

The generic structures A-X-B and -A-X-B-C is effective where A is at the amino terminus or where A is at the carboxy terminus, i.e., either orientation of the peptide bonds is permissible.

Portion B (Membrane-Translocatinz Sequence)

Disclosed herein, in certain embodiments, is a selective transport molecule.

In some embodiments, a selective transport molecule disclosed herein has the formula A-X-B-C, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker that is cleavable by thrombin.

In some embodiments, a selective transport molecule disclosed herein has the formula $(A-X-B-C)_n$-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; M is a macromolecular carrier; and n is an integer between 1 and 20.

In some embodiments, a selective transport molecule disclosed herein has the formula $(A-X-B)_n$-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; D is a dendrimer; and n is an integer between 1 and 20. In some embodiments, D comprises a cargo moiety. See Example 1 for methods of attaching a label to a selective transport molecule.

In some embodiments of molecules having features of the invention, peptide portion B includes between about 5 to about 20, or between about 9 to about 16 basic amino acids, and may be a series of basic amino acids (e.g., arginines, histidines, lysines, or other basic amino acids).

In some embodiments, portion B comprises 9 consecutive arginines (i.e., RRRRRRRRR or rrrrrrrrr).

A basic portion B may include amino acids that are not basic. Basic portion B may comprise other moieties, such as positively charged moieties. In embodiments, a basic portion B may be a positively charged portion, preferably having between about 5 and about 20 positive charges at physiological pH, that does not include an amino acid. In preferred embodiments, the amount of negative charge in portion A is approximately the same as the amount of positive charge in portion B.

Portion B is either L-amino acids or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that portion B may include non-standard amino acids, such as, for example, hydroxylysine, desmosine, isodesmosine, or other non-standard amino acids. Portion B may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion B may also include peptide mimetic moieties, including portions linked by non-peptide bonds and amino acids linked by or to non-amino acid portions.

In embodiments where X is a peptide cleavable by a protease, it may be preferable to join the C-terminus of X to the N-terminus of B, so that the new amino terminus created by cleavage of X contributes an additional positive charge that adds to the positive charges already present in B.

Portion X (Linkers)

Disclosed herein, in certain embodiments, is a selective transport molecule.

In some embodiments, a selective transport molecule disclosed herein has the formula A-X-B-C, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker that is cleavable by thrombin.

In some embodiments, a selective transport molecule disclosed herein has the formula $(A-X-B-C)_n$-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; M is a macromolecular carrier; and n is an integer between 1 and 20.

In some embodiments, a selective transport molecule disclosed herein has the formula $(A-X-B)_n$-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; D is a dendrimer; and n is an integer between 1 and 20. In some embodiments, D comprises a cargo moiety. See Example 1 for methods of attaching a label to a selective transport molecule.

Cleavage Conditions

In some embodiments, X is a cleavable linker. In some embodiments, a linker X is designed for cleavage in the presence of particular conditions or in a particular environment. In preferred embodiments, a linker X is cleavable under physiological conditions. Cleavage of such a linker X may, for example, be enhanced or may be affected by particular pathological signals or a particular environment related to cells in which cargo delivery is desired. The design of a linker X for cleavage by specific conditions, such as by a specific enzyme (e.g., thrombin), allows the targeting of cellular uptake to a specific location where such conditions obtain. Thus, one important way that selective transport molecules provide specific targeting of cellular uptake to desired cells, tissues, or regions is by the design of the linker portion X to be cleaved by conditions near such targeted cells, tissues, or regions. After cleavage of a linker X, the portions B-C of the molecule are then a simple conjugate of B and C, in some instances retaining a relatively small, inert stub remaining from a residual portion of linker X.

In some embodiments, X is cleaved by thrombin. In some embodiments, X is substantially specific for thrombin.

Linkers

In some embodiments, a linker consisting of one or more amino acids is used to join peptide sequence A (i.e., the sequence designed to prevent uptake into cells) and peptide sequence B (i.e., the MTS). Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity.

In some embodiments, X is a cleavable linker.

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

In some embodiments, X is about 5 to about 30 atoms in length. In some embodiments, X is about 6 atoms in length. In some embodiments, X is about 8 atoms in length. In some embodiments, X is about 10 atoms in length. In some embodiments, X is about 12 atoms in length. In some embodiments, X is about 14 atoms in length. In some embodiments, X is about 16 atoms in length. In some embodiments, X is about 18 atoms in length. In some embodiments, X is about 20 atoms in length. In some embodiments, X is about 25 atoms in length. In some embodiments, X is about 30 atoms in length.

In some embodiments, X is cleaved by thrombin. In some embodiments, the linker is substantially specific for thrombin.

In some embodiments, the linker has a formula selected from: DPRSFL (SEQ ID NO: 1), or PPRSFL (SEQ ID NO: 2).

In some embodiments, the linker binds peptide portion A (i.e., the peptide sequence which prevents cellular uptake) to peptide portion B (i.e., the MTS sequence) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, X comprises a peptide linkage. The peptide linkage comprises L-amino acids and/or D-amino acids. In embodiments of the invention, D-amino acids are preferred in order to minimize immunogenicity and nonspecific cleavage by background peptidases or proteases. Cellular uptake of oligo-D-arginine sequences is known to be as good as or better than that of oligo-L-arginines.

It will be understood that a linker disclosed herein may include non-standard amino acids, such as, for example, hydroxylysine, desmosine, isodesmosine, or other non-standard amino acids. A linker disclosed herein may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A linker disclosed herein may also include peptide mimetic moieties, including portions linked by non-peptide bonds and amino acids linked by or to non-amino acid portions.

In some embodiments, a selective transport molecule disclosed herein comprises a single of linker. Use of a single mechanism to mediate uptake of both imaging and therapeutic cargoes is particularly valuable, because imaging with noninjurious tracer quantities can be used to test whether a subsequent therapeutic dose is likely to concentrate correctly in the target tissue.

In some embodiments, a selective transport molecule disclosed herein comprises a plurality of linkers. Where a selective transport molecule disclosed herein includes multiple linkages X, separation of portion A from the other portions of the molecule requires cleavage of all linkages X. Cleavage of multiple linkers X may be simultaneous or sequential. Multiple linkages X may include linkages X having different specificities, so that separation of portion A from the other portions of the molecule requires that more than one condition or environment ("extracellular signals") be encountered by the molecule. Cleavage of multiple linkers X thus serves as a detector of combinations of such extracellular signals. For example, a selective transport molecule may include two linker portions Xa and Xb connecting basic portion B with acidic portion A. Both linkers Xa and Xb must be cleaved before acidic portion A is separated from basic portion B allowing entry of portion B and cargo moiety C (if any) to enter a cell. It will be understood that a linker region may link to either a basic portion B or a cargo moiety C independently of another linker that may be present, and that, where desired, more than two linker regions X may be included.

Combinations of two or more linkers X may be used to further modulate the targeting and delivery of molecules to desired cells, tissue or regions. Combinations of extracellular signals are used to widen or narrow the specificity of the cleavage of linkers X if desired. Where multiple linkers X are linked in parallel, the specificity of cleavage is narrowed, since each linker X must be cleaved before portion A may separate from the remainder of the molecule. Where multiple linkers X are linked in series, the specificity of cleavage is broadened, since cleavage on any one linker X allows separation of portion A from the remainder of the molecule. For example, in order to detect either a protease OR hypoxia (i.e., to cleave X in the presence of either protease or hypoxia), a linker X is designed to place the protease-sensitive and reduction-sensitive sites in tandem, so that cleavage of either would suffice to allow separation of the acidic portion A. Alternatively, in order to detect the presence of both a protease AND hypoxia (i.e., to cleave X in the presence of both protease and hypoxia but not in the presence of only one alone), a linker X is designed to place the protease sensitive site between at least one pair of cysteines that are disulfide-bonded to each other. In that case, both protease cleavage and disulfide reduction are required in order to allow separation of portion A.

Macromolecular Carrier

Disclosed herein, in certain embodiments, is a selective transport molecule with increased in vivo circulation. In some embodiments, a selective transport molecule disclosed herein has the formula $(A-X-B-C)_n$-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; M is a macromolecular carrier; and n is an integer between 1 and 20.

The term "carrier" means an inert molecule that increases (a) plasma half-life and (b) solubility.

In some embodiments, a carrier decreases uptake of a selective transport molecule into cartilage. In some embodiments, a carrier decreases uptake of a selective transport molecule into joints. In some embodiments, a carrier decreases uptake of a selective transport molecule into the liver. In some embodiments, a carrier decreases uptake of a selective transport molecule into kidneys.

In some embodiments, a carrier increases plasma half-life and solubility by reducing glomerular filtration. In some embodiments, a carrier increases tumor uptake due to enhanced permeability and retention (EPR) of tumor vasculature.

In some embodiments, M is bound to A. In some embodiments, M is bound to A at the n-terminal poly glutamate. In some embodiments, M is bound to A (or, the n-terminal poly glutamate) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, M is bound to B. In some embodiments, M is bound to B at the c-terminal polyarginine. In some embodiments, M is bound to B (or, the c-terminal polyarginine) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, M is selected from a protein, a synthetic or natural polymer, or a dendrimer. In some embodiments, M is selected from dextran, a PEG polymer (e.g., PEG 5 kDa and PEG 121cDa), albumin, or a combination thereof. In some embodiments, M is a PEG polymer.

In some embodiments, the size of the carrier is between 50 and 70kD. In some embodiments, small amounts of negative charge keep peptides out of the liver while not causing synovial uptake.

In some embodiments, the selective transport molecule is conjugated to albumin. In certain instances, albumin is excluded from the glomerular filtrate under normal physiological conditions. In some embodiments, the selective transport molecule comprises a reactive group such as maleimide that can form a covalent conjugate with albumin. A selective transport molecule comprising albumin results in enhanced accumulation of cleaved selective transport molecules in tumors in a cleavage dependent manner. See, Example 2. In some embodiments, albumin conjugates have good pharmacokinetic properties but are difficult to work with synthetically.

In some embodiments, the selective transport molecule is conjugated to a PEG polymer. In some embodiments, the selective transport molecule is conjugated to a PEG 5 kDa polymer. In some embodiments, the selective transport molecule is conjugated to a PEG 121(Da polymer. In some embodiments, 5kD PEG conjugates behaved similarly to free peptides. In some embodiments, 121cD PEG conjugates had a longer halflife as compared to free peptides. See Example 5 for a detailed analysis of the effects of using a PEG polymer.

In some embodiments, the selective transport molecule is conjugated to a dextran. In some embodiments, the selective transport molecule is conjugated to a 70 kDa dextran. In some embodiments, dextran conjugates, being a mixture of molecular weights, are difficult to synthesize and purify reproducibly. See Example 5 for a detailed analysis of the effects of using a dextran.

In some embodiments, the selective transport molecule is conjugated to streptavidin. See Example 5 for a detailed analysis of the effects of using streptavadin.

In some embodiments, the selective transport molecule is conjugated to a fifth generation PAMAM dendrimer.

In some embodiments, a carrier is capped. See Example 1 for methods of capping. In some embodiments, capping a carrier improves the pharmacokinetics and reduces cytotoxicity of a carrier by adding hydrophilicity. In some embodiments, the cap is selected from: Acetyl, succinyl, 3-hydroxypropionyl, 2-sulfobenzoyl, glycidyl, PEG-2, PEG-4, PEG-8 and PEG-12. For a detailed analysis of the effects of capping, see Example 6.

Dendrimers

Disclosed herein, in certain embodiments, is a selective transport molecule. In some embodiments, a selective transport molecule disclosed herein has the formula $(A-X-B)_n$-D, wherein D is a dendrimer; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and n is an integer between 1 and 20; and wherein D is bound to an (A-X-B) moiety by a bond with a B. In some embodiments, D is bound to an (A-X-B) moiety by a bond with a polyarginine terminus. In some embodiments, D comprises at least one cargo moiety. See Example 1 for method of conjugating a peptide to a dendrimer.

As used herein, "dendrimer" means a poly-functional (or, poly-branched) molecule. In some embodiments, a denrimer is a structure in which a central molecule branches repetitively and repetitiously. In some embodiments, the dendrimer is a nanoparticle.

In some embodiments, D is bound to B (or, the c-terminal polyarginine) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, a plurality of (A-X-B) moieties are attached to D. See, Example 3. In some embodiments, a plurality of cargo moieties are attached to D. In some embodiments, (a) a plurality of (A-X-B) moieties are attached to D; and (b) a plurality of cargo moieties are attached to D.

In some embodiments, the dendrimer comprises a reactive group such as maleimide that can form a covalent conjugate with albumin. In some embodiments, a dendrimer is conjugated to a selective transport molecule via a maleimide linker at the C-terminal end of the selective transport molecule.

In some embodiments, conjugating a selective transport molecule to a dendrimer increases plasma half-life as compared to an unconjugated (or, free) selective transport molecule. In some embodiments, a selective transport molecule conjugated to a dendrimer results in a decrease in acute toxicity as compared to unconjugated selective transport molecules. In some embodiments, a selective transport molecule conjugated to a dendrimer reduces uptake by synovium, cartilage and kidney as compared to unconjugated selective transport molecules.

In some embodiments, a selective transport molecule conjugated to a dendrimeric nanoparticle is used to target tumor associated macrophages. In some embodiments, a selective transport molecule conjugated to a dendrimeric nanoparticle, wherein the nanoparticle further comprises Ricin A, is used to poison subcutaneous macrophages. See Example 7 for a detailed analysis of the effects of using a dendrimeric nanoparticle.

Cargo

Disclosed herein, in certain embodiments, is a selective transport molecule.

In some embodiments, a selective transport molecule disclosed herein has the formula A-X-B-C, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker that is cleavable by thrombin.

In some embodiments, a selective transport molecule disclosed herein has the formula $(A-X-B-C)_n$-M, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; M is a macromolecular carrier; and n is an integer between 1 and 20.

In some embodiments, a selective transport molecule disclosed herein has the formula $(A-X-B)_n$-D, wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; D is a dendrimer; and n is an integer between 1 and 20. In some embodiments, D comprises a cargo moiety. See Example 1 for methods of attaching a label to a selective transport molecule.

Selective transport molecules disclosed herein are suitable for carrying different cargoes, including different types of cargoes and different species of the same types of cargo, for uptake into cells. For example, different types of cargo may include marker cargoes (e.g., fluorescent or radioactive label moieties) and therapeutic cargoes (e.g., chemotherapeutic molecules such as methotrexate or doxorubicin), or other cargoes. Where destruction of aberrant or diseased cells is therapeutically required, a therapeutic cargo may include a “cytotoxic agent,” i.e., a substance that inhibits or prevents the function of cells and/or causes destruction of cells.

Delivery of cargo such as a fluorescent molecule may be used to visualize cells having a certain condition or cells in a region exhibiting a particular condition. For example, thrombosis (clot formation) may be visualized by designing a linker X to be cleaved by thrombin. Thus, fluorescent molecules are one example of a marker that may be delivered to target cells and regions upon release of a portion A upon cleavage of a linker X.

In some embodiments, the cargo moiety is selected from an imaging agent, a therapeutic agent, a lipid, or a combination thereof.

In some embodiments, the cargo portion comprises at least two cargo moieties. In some embodiments, C comprises a marker cargo and a therapeutic cargo. Multiple cargo moieties may allow, for example, delivery of both a radioactive marker and an ultrasound or contrast agent, allowing imaging by different modalities. Alternatively, for example, delivery of radioactive cargo along with an anticancer agent, providing enhanced anticancer activity, or delivery of a radioactive cargo with a fluorescent cargo, allowing multiple means of localizing and identifying cells which have taken up cargo.

Attachment of a Cargo Moiety

The cargo moiety is attached to B in any location or orientation. The cargo moiety need not be located at an opposite end of portion B than a linker X. Any location of attachment of the cargo moiety to B is acceptable as long as that attachment remains after X is cleaved. For example, the cargo moiety may be attached to or near to an end of portion B with linker X attached to an opposite end of portion B as illustrated in FIGS. 2A and 2B. The cargo moiety may also be attached to or near to an end of portion B with linker X attached to or near to the same end of portion B.

Wherein the molecule comprises a dendrimer, the cargo is attached directly to D. By way of non-limiting example, the cargo is attached as follows:

$(A-X-B)_n$-D-cargo.

Imaging Agents as Cargo

In some embodiments, a cargo moiety is a fluorescent molecule such as fluorescein. Fluorescent cargo moieties enable easy measurement by fluorescence microscopy or flow cytometry in unfixed cultured cells.

In some embodiments, a cargo moiety is labeled with a positron-emitting isotope (e.g., $^{18}$F) for positron emission tomography (PET), gamma-ray isotope (e.g., $^{99m}$Tc) for single photon emission computed tomography (SPECT), a paramagnetic molecule or nanoparticle (e.g., $G^{3+}$ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, a cargo moiety is a radioactive moiety, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, radioactive isotopes of Lu, and others.

In some embodiments, a cargo moiety is a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. No. 4,452,720, U.S. Pat. No. 5,227,487, and U.S. Pat. No. 5,543,295.

In some embodiments, a cargo moiety is a fluorescein dye. Typical fluorescein dyes include, but are not limited to, 5-carboxyfluorescein, fluorescein-5-isothiocyanate and 6-carboxyfluorescein; examples of other fluorescein dyes can be found, for example, in U.S. Pat. No. 6,008,379, U.S. Pat. No. 5,750,409, U.S. Pat. No. 5,066,580, and U.S. Pat. No. 4,439,356. A cargo moiety C may include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS REDO), and other rhodamine dyes. Other rhodamine dyes can be found, for example, in U.S. Pat. No. 6,080,852, U.S. Pat. No. 6,025,505, U.S. Pat. No. 5,936,087, U.S. Pat. No. 5,750,409. A cargo moiety C may include a cyanine dye, such as, for example, Cy3, Cy3B, Cy3.5, Cy5, Cy5.5, Cy 7.

Some of the above compounds or their derivatives will produce phosphorescence in addition to fluorescence, or will only phosphoresce. Some phosphorescent compounds include porphyrins, phthalocyanines, polyaromatic compounds such as pyrenes, anthracenes and acenaphthenes, and so forth, and may be, or may be included in, a cargo moiety. A cargo moiety may also be or include a fluorescence quencher, such as, for example, a (4-dimethylamino-phenylazo)benzoic acid (DABCYL) group.

In some embodiments, a cargo moiety is a fluorescent label. In some embodiments, a cargo moiety is indocarbocyanine dye, Cy5, Cy5.5, Cy7, IR800CW, or a combination thereof. In some embodiments, a cargo moiety is a MRI contrast agent. In some embodiments, a cargo moiety is Gd complex of [4,7,10-tris(carboxymethyl)-1,4,7,10-tetraazacyclododec-1-yl]acetyl.

In some embodiments, a cargo moiety is all or part of a molecular beacon. As used herein, "molecular beacon" means a pair of connected compounds having complementary regions with a fluorophore and a fluorescent quencher so that the fluorescence of the fluorophore is quenched by the quencher. One or both of the complementary regions may be part of the cargo moiety. Where only one of the complementary regions (e.g., the fluorescent moiety) is part of the cargo moiety, and where the quencher moiety is part of the linker X or the acidic portion A, then cleavage of the linker X will allow fluorescence of the fluorescent portion and detection of the cleavage. Upon cellular uptake, the fluorescent portion of a molecular beacon will allow detection of the cell. For example, a quencher Q may be attached to an acidic portion A to form a selective transport molecule having features of the invention Q-A-X-B-C where cargo is fluorescent and is quenched by Q. The quenching of the cargo moiety by Q is relieved upon cleavage of X, allowing fluorescent marking of a cell taking up portion B-C. The combination of fluorescence dequenching and selective uptake should increase contrast between tissues able to cleave X compared to those that cannot cleave X.

Therapeutic Agents as Cargo

In some embodiments, a cargo moiety is a therapeutic agent, such as a chemical compound useful in the treatment of cancer, ischemic tissue, or necrotic tissue.

For therapeutic purposes, for example, suitable classes of cargo include but are not limited to: a) chemotherapeutic agents; b) radiation sensitizing agents; or c) peptides or proteins that modulate apoptosis, the cell cycle, or other crucial signaling cascades.

In some embodiments, a cargo moiety is an agent that treats a cardiovascular disorder. In some embodiments, the cargo moiety is a niacin, a fibrate, a statin, an Apo-A1 mimetic peptide, an apoA-I transcriptional up-regulator, an ACAT inhibitor, a CETP modulator, or a combination thereof, a Glycoprotein (GP) IIb/IIIa receptor antagonist, a P2Y12 receptor antagonist, a Lp-PLA2-inhibitor, a leukotriene inhibitor, a MIF antagonist, or a combination thereof. In some embodiments the cargo moiety is atorvastatin; cerivastatin; fluvastatin; lovastatin; mevastatin; pitavastatin; pravastatin; rosuvastatin; simvastatin; simvastatin and ezetimibe; lovastatin and niacin, extended-release; atorvastatin and amlodipine besylate; simvastatin and niacin, extended-release; bezafibrate; ciprofibrate; clofibrate; gemfibrozil; fenofibrate; DF4 (Ac-D-W-F-K-A-F-Y-D-K-V-A-E-K-F-K-E-A-F-NH2 (SEQ ID NO: 3)); DFS; RVX-208 (Resverlogix); avasimibe; pactimibe sulfate (CS-505); CI-1011 (2,6-diisopropylphenyl [(2,4,6-triisopropylphenyl) acetyl]sulfamate); CI-976 (2,2-dimethyl-N-(2,4,6-trimethoxyphenyl)dodecanamide); VULM1457 (1-(2,6-diisopropyl-phenyl)-3-[4-(4'-nitrophenylthio)phenyl] urea); CI-976 (2,2-dimethyl-N-(2,4,6-trimethoxyphenyl)dodecanamide); E-5324 (n-butyl-N'-(2-(3-(5-ethyl-4-phenyl-1H-imidazol-1-yl)propoxy)-6-methylphenyl)urea); HL-004 (N-(2,6-diisopropylphenyl) tetradecylthioacetamide); KY-455 (N-(4,6-dimethyl-1-pentylindolin-7-yl)-2,2-dimethylpropanamide); FY-087 (N42-[N'-pentyl-(6,6-dimethyl-2,4-heptadiynyl)amino]ethyl]-(2-methyl-1-naphthyl-thio)acetamide); MCC-147 (Mitsubishi Pharma); F 12511 ((S)-2',3',5'-trimethyl-4'-hydroxy-alpha-dodecylthioacetanilide); SMP-500 (Sumitomo Pharmaceuticals); CL 277082 (2,4-difluoro-phenyl-NR4-(2,2-dimethylpropyl)phenyl]methyl]-N-(hepthyl)urea); F-1394 ((1s,2s)-2-[3-(2,2-dimethylpropyl)-3-nonylureido]aminocyclohexane-1-yl 3-[N-(2,2,5,5-tetramethyl-1,3-dioxane-4-carbonyl)amino]propionate); CP-113818 (N-(2,4-bis(methylthio)-6-methylpyridin-3-yl)-2-(hexylthio)decanoic acid amide); YM-750; torcetrapib; anacetrapid; JTT-705 (Japan Tobacco/Roche); abciximab; eptifibatide; tirofiban; roxifiban; variabilin; XV 459 (N(3)-(2-(3-(4-formamidinophenyl)isoxazolin-5-yl)acetyl)-N(2)-(1-butyloxycarbonyl)-2,3-diaminopropionate); SR 121566A (3-[N-{4-[4-(aminoiminomethyl)phenyl]-1,3-thiazol-2-yl1-N-(1-carboxymethylpiperid-4-yl) amino] propionic acid, trihydrochloride); FK419 ((S)-2-acetylamino-3-[(R)-[1-[3-(piperidin-4-yl) propionyl] piperidin-3-ylcarbonyl] amino] propionic acid trihydrate); clopidogrel; prasugrel; cangrelor; AZD6140 (AstraZeneca); MRS 2395 (2,2-Dimethyl-propionic acid 3-(2-chloro-6-methylaminopurin-9-yl)-2-(2,2-dimethyl-propionyloxymethyl)-propyl ester); BX 667 (Berlex Biosciences); BX 048 (Berlex Biosciences); darapladib (SB 480848); SB-435495 (GlaxoSmithKline); SB-222657 (GlaxoSmithKline); SB-253514 (GlaxoSmithKline); A-81834 (3-(3-(1,1-dimethylethylthio-5-(quinoline-2-yl-methoxy)-1-(4-chloromethylphenyl)indole-2-yl)-2,2-dimethylpropionaldehyde oxime-O-2-acetic acid; AME103 (Amira); AME803 (Amira); atreleuton; BAY-x-1005 ((R)-(+)-alpha-cyclopentyl-4-(2-quinolinylmethoxy)-Benzeneacetic acid); CJ-13610 (4-(3-(4-(2-Methyl-imidazol-1-yl)-phenylsulfanyl)-phenyl)-tetrahydro-pyran-4-carboxylic acid amide); DG-031 (DeCode); DG-051 (DeCode); MK886 (1-[(4-chlorophenyl)methyl]3-[(1,1-dimethylethypthio]-α,α-dimethyl-5-(1-methylethyl)-1H-indole-2-propanoic acid, sodium salt); MK591 (3-(1-4[(4-chlorophenyl) methyl]-3-Rt-butylthio)-5-((2-quinoly)methoxy)-1H-indole-2]-, dimehtylpropanoic acid); RP64966 ([4-[5-(3-Phenyl-propyl)thiophen-2-yl]butoxy] acetic acid); SA6541 ((R)-S-[[4-(dimethylamino)phenyl]methyl]-N-(3-mercapto-2methyl-1-oxopropyl-L-cycteine); SC-56938 (ethyl-1-[2-[4-(phenylmethyl)phenoxy] ethyl]-4-piperidine-carboxylate); VIA-2291 (Via Pharmaceuticals); WY-47,288 (2-[(1-naphthalenyloxy)methyl]quinoline); zileuton; ZD-2138 (6-

((3-fluoro-5-(tetrahydro-4-methoxy-2H-pyran-4yl) phenoxy)methyl)-1-methyl-2(1H)-quinolinone); or combinations thereof In some embodiments, the drug is an agent that modulates death (e.g., via apoptosis or necrosis) of a cell. In some embodiments, the drug is a cytotoxic agent. In some embodiments, the drug is maytansine, methotrexate (RHEUMATREX®, Amethopterin); cyclophosphamide (CYTOXAN®); thalidomide (THALIDOMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinbiastine; vincristine; vinorelbine; vorinostat; zosuquidar; or a combination thereof. In some embodiments, the drug is a pro-apoptotic agent. In some embodiments, the drug is an anti-apoptotic agent. In some embodiments, the drug is selected from: minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (542-Amino-4-pyrimidinyl)-4-(4-fluorophenyl)-1-(4-piperidinlypimidazole); D-JNKI-1 ((D)-hJIP175-157-DPro-DPro-(D)-HIV-TAT57-48); AM-111 (Auris); SP600125 (anthra[1,9-cd]pyrazol-6(2H)-one); JNK Inhibitor I ((L)-HIV-TAT48-57-PP-JBD20); JNK Inhibitor III ((L)-HIV-TAT47-57-gaba-c-Jun533-57); AS601245 (1,3-benzothiazol-2-yl (2-[[2-(3-pyridinyl) ethyl] amino]-4 pyrimidinyl) acetonitrile); JNK Inhibitor VI (H2N-RP-KRPTTLNLF-NH2 (SEQ ID NO: 7)); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (4-[5-(4-chlorophenyl)-3-(trifluoromethyl)-1H-pyrazol-1-yl]benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3,6-Dibromocarbazol-9-yl)-3-piperazin-1-yl-propan-2-01); Bax inhibiting peptide P5 (also known as Bax inhibitor peptide P5); Kp7-6; FAIM(S) (Fas apoptosis inhibitory molecule-short); FAIM(L) (Fas apoptosis inhibitory molecule-long); Fas:Fc; FAP-1; NOK2; F2051; F1926; F2928; ZB4; Fas M3 mAb; EGF; 740 Y-P; SC 3036 (KKHTDDGYMPMSPGVA (SEQ ID NO: 8)); PI 3-kinase Activator (Santa Cruz Biotechnology, Inc.); Pam3Cys ((S)-(2,3-bis(palmitoyloxy)-(2R5)-propyl)-N-palmitoyl-(R)-Cys-(S)-Ser(S)-Lys4-0H, trihydrochloride); Act1 (NF-kB activator 1); an anti-IkB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKK-TALDWSWLQTE (SEQ ID NO: 9)); NF-kB Activation Inhibitor (6-Amino-4-(4-phenoxyphenylethylamino)quinazoline); NF-kB Activation Inhibitor H (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVLLALLAPVQRKRQKLMP (SEQ ID NO: 10)); Oridonin; Parthenolide; PPM-18 (2-Benzoylamino-1,4-naphthoquinone); Ro106-9920; Sulfasalazine; TIRAP Inhibitor Peptide (RQIKIWFNRRMKWK-KLQLRDAAPGGAIVS (SEQ ID NO: 11)); Withaferin A; Wogonin; BAY 11-7082 ((E)34(4-Methylphenyl)sulfonyl]-2-propenenitrile); BAY 11-7085 ((E)3-[(4-t-Butylphenyl) sulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinly)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401-[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2, 1-b]thiazole dihydrochloride); SB-200646 (N-(1-Methyl-1H-indol-5-yl)-N-3-pyridinylurea); CMPD-1 (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl) phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)-); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-VAD-FMK (Benzyloxycarbonyl-Val-Ala-Asp(OMe)-fluoromethylketone); z-LEHD-FMK (benzyloxycarbonyl-Leu-Glu(OMe)-His-Asp(OMe)-fluoromethylketone) (SEQ ID NO: 12); B-D-FMK (boc-aspartyl(Ome)-fluoromethylketone); Ac-LEHD-CHO (N-acetyl-Leu-Glu-His-Asp-CHO) (SEQ ID NO: 13); Ac-IETD-CHO (N-acetyl-Ile-Glu-Thr-Asp-CHO) (SEQ ID NO: 14); z-IETD-FMK (benzyloxycarbonyl-Ile-Glu(OMe)-Thr-Asp (OMe)-fluoromethy lketone) (SEQ ID NO: 15); FAM-LEHD-FMK (benzyloxycarbonyl Leu-Glu-His-Asp-fluoromethyl ketone) (SEQ ID NO: 16); FAM-LETD-FMK (benzyloxycarbonyl Leu-Glu-Thr-Asp-fluoromethyl ketone) (SEQ ID NO: 17); Q-VD-OPH (Quinoline-Val-Asp-CH2-O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-a (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon;

isoliquirtigen; butein; 4,2',4'-trihydroxychalcone; 3,4,2',4', 6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O; Ambroxol (trans-4-(2-Amino-3,5-dibromobenzylamino)cyclohexane-HCl and U83836E ((-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol.2HCl; β-1'-5-methyl-nicotinamide-2'-deoxyribose; β-D-1'-5-methyl-nicotinamide-2'-deoxyribofuranoside; (β-1'-4,5 dimethyl nicotinamide-2'-de-oxyribose; β-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3,4-d]pyrimidin-4-amine); Lavendustin A (5-[[(2,5-Dihydroxyphenyl)methyl][(2-hydroxyphenyl)methyl]amino]-2-hydroxybenzoic acid); MNS (3,4-Methylenedioxy-h-nitrostyrene); PP1 (1-(1,1-Dimethylethyl)-1-(4-methylphenyl)-1H-pyrazolo [3, 4-d]pyrimidin-4-amine); PP2 (3-(4-chlorophenyl) 1-(1,1-dimethylethyl)-1H-pyrazolo [3,4-d]pyrimidin-4-amine); KX-004 (Kinex); KX-005 (Kinex); KX-136 (Kinex); KX-174 (Kinex); KX-141 (Kinex); KX2-328 (Kinex); KX-306 (Kinex); KX-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl)ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphneyl)-2-(6-(4-(2-hydroxyethyl)-piperazin-1-yl)-2-methylpyrimidin-4-ylamino) thiazole-5-carboxamide); GN963 (trans-4-(6,7-dimethoxyquinoxalin-2ylamino)cyclohexanol sulfate); Bosutinib (4-((2,4-dichloro-5-methoxyphenyl) amino)-6-methoxy-7-(3-(4-methyl-1-piperazinyl)propoxy)-3-quinolinecarbonitrile); or combinations thereof.

Lipids as Cargo

Disclosed herein, in certain embodiments, is a selective transport molecule. In some embodiments, a selective transport molecule disclosed herein has the formula $(A-X-B)_n$-L, wherein L is a lipid; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker; and n is an integer between 1 and 20; and wherein L is bound to an (A-X-B) moiety by a bond with a B.

In some embodiments, the lipid entraps a hydrophobic molecule. In some embodiments, the lipid entraps at least one agent selected from the group consisting of a therapeutic moiety or an imaging moiety.

In some embodiments, the lipid is PEGylated. In some embodiments, the lipid is PEG(2K)-phosphatidylethanolamine.

Methods of Use

Visualizing Thrombin

Disclosed herein, in certain embodiments, is a method of imaging thrombin activity in a subject. In some embodiments, the method comprises imaging thrombin activity after the subject has been administered a selective transport molecule disclosed herein.

In some embodiments, an increase in thrombin activity over normal ranges indicates the presence of a cancer, ischemia, or an atherosclerotic plaque.

In some embodiments, the signal intensity of an imaging agent corresponds to the total atherosclerotic plaque burden, histologic stage of the atherosclerotic plaque, and provides evidence of recent plaque rupture. In some embodiments, administering a selective transport molecule disclosed herein allows a medical professional to image the surgical margins of an atherosclerotic plaque for removal.

In some embodiments, the signal intensity of an imaging agent corresponds to the size of the tumor. In some embodiments, administering a selective transport molecule disclosed herein allows a medical professional to evaluate the progression or regression of a tumor. In some embodiments, administering a selective transport molecule disclosed herein allows a medical professional to image the surgical margins for a tumor or tissue resection in a subject in need thereof In some embodiments, the signal intensity of an imaging agent corresponds to amount of ischemia and the damage to the surrounding cells. As used herein, "ischemia" means a shortage of the blood supply to an organ, (i.e. a shortage of oxygen, glucose and other blood-borne fuels). In some embodiments, ischemia is caused by occlusion of a vessel or artery (e.g., due to an embolism or thrombosis). In some embodiments, ischemia is caused by hemorrhage. In some embodiments, ischemia results in a stroke. In some embodiments, administering a selective transport molecule disclosed herein allows a medical professional to evaluate a subject's risk of developing a stroke.

In some embodiments, the image of thrombin activity is memorialized (i.e., a record is created) in print (e.g., as a photograph).

In some embodiments, image of thrombin activity is stored in a computer module. In some embodiments, the image of thrombin activity is stored in computer memory. In some embodiments, the image of thrombin activity is stored as a visual file (e.g., JPEG, MPEG, MPEG-2, H.264/MPEG-4 AVC, and SMPTE VC-1). In some embodiments, the image of thrombin activity is stored in volatile computer memory. As used herein, "volatile memory" means computer memory that requires electricity to maintain the stored information. In some embodiments, the volatile memory is random access memory (RAM), dynamic random access memory (DRAM), or static random access memory (SRAM). In some embodiments, the image of thrombin activity is stored in non-volatile computer memory. As used herein, "non-volatile memory" means computer memory that retains the stored information in the absence of electricity (e.g., hard disks, floppy disks, and magnetic tape, or optical discs). In some embodiments, the image of thrombin activity is stored on an optical disc (e.g., a Blu-Ray disc, DVD, or a CD). In some embodiments, the image of thrombin activity is stored on a magnetic storage device.

Visualizing Tumors

In some embodiments, a selective transport molecule disclosed herein is administered to a subject in need thereof to visualize a tumor. In some embodiments, a selective transport molecule disclosed herein is administered to a subject in need thereof prior to surgery. In some embodiments, a selective transport molecule disclosed herein is administered to a subject in need thereof prior to surgery and used to define the surgical margins of a tumor. In some embodiments, a dual modality (MR and fluorescence) selective transport molecule allows pre-operative staging by oncologists and radiologists, particularly for cancers such as prostate where invasion of a capsule is important, preventing surgery on patients who are non-operative candidates. In some embodiments, the anatomical and biochemical information given by the dual label selective transport molecule are useful for surgeons in planning complex surgical procedures. In some embodiments, tight binding of selective transport molecules to the site of cleavage provides localized information regarding tumor biology that not only allows the surgeon to focus on the most invasive areas of tumor growth with intraoperative fluorescence imaging but also allows the pathologist to do the same with intraoperative histology. Following surgery, in some embodiments, the dual probe allows further evaluation for completeness of tumor removal with a second MRI.

In some embodiments, the image of a tumor is memorialized (i.e., a record is created) in print (e.g., as a photograph).

In some embodiments, image of a tumor is stored in a computer module. In some embodiments, the image of a tumor is stored in computer memory. In some embodiments, the image of a tumor is stored as a visual file (e.g., JPEG, MPEG, MPEG-2, H.264/MPEG-4 AVC, and SMPTE VC-1). In some embodiments, the image of a tumor is stored in volatile computer memory. As used herein, "volatile memory" means computer memory that requires electricity to maintain the stored information. In some embodiments, the volatile memory is random access memory (RAM), dynamic random access memory (DRAM), or static random access memory (SRAM). In some embodiments, the image of a tumor is stored in non-volatile computer memory. As used herein, "non-volatile memory" means computer memory that retains the stored information in the absence of electricity (e.g., hard disks, floppy disks, and magnetic tape, or optical discs). In some embodiments, the image of a tumor is stored on an optical disc (e.g., a Blu-Ray disc, DVD, or a CD). In some embodiments, the image of a tumor is stored on a magnetic storage device.

Visualizing Ischemia

In some embodiments, a selective transport molecule disclosed herein is administered to a subject in need thereof to visualize an area of ischemia. In some embodiments, a selective transport molecule disclosed herein is administered to a subject in need thereof prior to surgery. In some embodiments, a selective transport molecule disclosed herein is administered to a subject in need thereof prior to surgery and used to define an area of ischemia.

In some embodiments, the image of an area of ischemia is memorialized (i.e., a record is created) in print (e.g., as a photograph).

In some embodiments, image of an area of ischemia is stored in a computer module. In some embodiments, the image of an area of ischemia is stored in computer memory. In some embodiments, the image of an area of ischemia is stored as a visual file (e.g., JPEG, MPEG, MPEG-2, H.264/MPEG-4 AVC, and SMPTE VC-1). In some embodiments, the image of an area of ischemia is stored in volatile computer memory. As used herein, "volatile memory" means computer memory that requires electricity to maintain the stored information. In some embodiments, the volatile memory is random access memory (RAM), dynamic random access memory (DRAM), or static random access memory (SRAM). In some embodiments, the image of an area of ischemia is stored in non-volatile computer memory. As used herein, "non-volatile memory" means computer memory that retains the stored information in the absence of electricity (e.g., hard disks, floppy disks, and magnetic tape, or optical discs). In some embodiments, the image of an area of ischemia is stored on an optical disc (e.g., a Blu-Ray disc, DVD, or a CD). In some embodiments, the image of an area of ischemia is stored on a magnetic storage device.

Visualizing Atherosclerotic Plaques

In some embodiments, a selective transport molecule disclosed herein is administered to a subject in need thereof prior to surgery. In some embodiments, a selective transport molecule disclosed herein is administered to a subject in need thereof prior to surgery and used to highlight high risk plaques intraoperatively. In some embodiments, administering a selective transport molecule disclosed herein prior to surgery lowers patient morbidity in surgical procedures (e.g., carotid endarterectomy). In some embodiments, administering a selective transport molecule disclosed herein prior to surgery lowers patient morbidity in iatrogenic surgical procedures, coronary artery surgical procedures, and mesenteric artery surgical procedures. In some embodiments, administering a selective transport molecule disclosed herein prior to surgery reduces the incidence of embolic events, myocardial infarction and bowel necrosis.

In some embodiments, the image of an atherosclerotic plaque is memorialized (i.e., a record is created) in print (e.g., as a photograph).

In some embodiments, image of an atherosclerotic plaque is stored in a computer module. In some embodiments, the image of an atherosclerotic plaque is stored in computer memory. In some embodiments, the image of an atherosclerotic plaque is stored as a visual file (e.g., JPEG, MPEG, MPEG-2, H.264/MPEG-4 AVC, and SMPTE VC-1). In some embodiments, the image of an atherosclerotic plaque is stored in volatile computer memory. As used herein, "volatile memory" means computer memory that requires electricity to maintain the stored information. In some embodiments, the volatile memory is random access memory (RAM), dynamic random access memory (DRAM), or static random access memory (SRAM). In some embodiments, the image of an atherosclerotic plaque is stored in non-volatile computer memory. As used herein, "non-volatile memory" means computer memory that retains the stored information in the absence of electricity (e.g., hard disks, floppy disks, and magnetic tape, or optical discs). In some embodiments, the image of an atherosclerotic plaque is stored on an optical disc (e.g., a Blu-Ray disc, DVD, or a CD). In some embodiments, the image of an atherosclerotic plaque is stored on a magnetic storage device.

Management of Atherosclerotic Disease

In some embodiments, a selective transport molecule disclosed herein is administered to a subject to aid in management of atherosclerotic disease. In some embodiments, a selective transport molecule disclosed herein is administered to a subject to aid a medical professional in distinguishing pathologic features of a plaque with the potential to rupture and cause embolic disease. In some embodiments, a selective transport molecule disclosed herein is administered to a subject to aid a medical professional in distinguishing patients with plaques at high risk for rupture, or the "high risk patient". In some embodiments, a selective transport molecule disclosed herein is administered to a subject to aid a medical professional in characterizing the risk associated with an atherosclerotic plaque in a subject, wherein the risk is proportional to the imaging agent signal intensity. Currently tissue examination of excised carotid endarterectomy fragments includes looking for distinctive pathological features such as fissures, micro-ulcerations, microthrombi or calcified nodules. This task is much more difficult in specimens that do not contain vessel wall, leading to significant intraobserver variability in identifying the rupture potential of surgically excised plaques (e.g., those removed during carotid endarterectomy).

Drug Delivery

Disclosed herein, in certain embodiments, are methods of targeted drug delivery. In some embodiments, a selective transport molecule described herein delivers a drug to a specific target (e.g., a cell or a plurality of cells). In some embodiments, a selective transport molecule described herein delivers a drug to a cell or tissue characterized by elevated thrombin levels when compared to normal cell or tissue conditions.

In some embodiments, the drug is an agent that treats a cardiovascular disorder. In some embodiments, the drug is a niacin, a fibrate, a statin, an Apo-A1 mimetic peptide, an apoA-I transcriptional up-regulator, an ACAT inhibitor, a CETP modulator, or a combination thereof, a Glycoprotein (GP) IIb/IIIa receptor antagonist, a P2Y12 receptor antagonist, a Lp-PLA2-inhibitor, a leukotriene inhibitor, a MIF antagonist, or a combination thereof. In some embodiments the drug is atorvastatin; cerivastatin; fluvastatin; lovastatin; mevastatin; pitavastatin; pravastatin; rosuvastatin; simvastatin; simvastatin and ezetimibe; lovastatin and niacin, extended-release; atorvastatin and amlodipine besylate; simvastatin and niacin, extended-release; bezafibrate; ciprofibrate; clofibrate; gemfibrozil; fenofibrate; DF4 (Ac-D-W-F-K-A-F-Y-D-K-V-A-E-K-F-K-E-A-F-NH2 (SEQ ID NO: 3)); DFS; RVX-208 (Resverlogix); avasimibe; pactimibe sulfate (CS-505); CI-1011 (2,6-diisopropylphenyl [(2, 4,6-triisopropylphenyl)acetyl]sulfamate); CI-976 (2,2-dimethyl-N-(2,4,6-trimethoxyphenyl)dodecanamide); VULM1457 (1-(2,6-diisopropyl-phenyl)-3[4-(4'-nitrophenylthio)phenyl] urea); CI-976 (2,2-dimethyl-N-(2,4,6-trimethoxyphenyl)dodecanamide); E-5324 (n-butyl-N'-(2-(3-(5-ethyl-4-phenyl-1H-imidazol-1-yl)propoxy)-6-methylphenyl)urea); HL-004 (N-(2,6-diisopropylphenyl) tetradecylthioacetamide); KY-455 (N-(4,6-dimethyl-1-pentylindolin-7-yl)-2,2-dimethylpropanamide); FY-087 (N[2-[N'-pentyl-(6,6-dimethyl-2,4-heptadiynyl(amino]ethyl]-(2-methyl-1-naphthyl-thio) acetamide); MCC-147 (Mitsubishi Pharma); F 12511 ((S)-2',3',5'-trimethyl-4'-hydroxy-alpha-dodecylthioacetanilide); SMP-500 (Sumitomo Pharmaceuticals); CL 277082 (2,4-difluoro-phenyl-N[[4-(2,2-dimethylpropyl)phenylimethyl]-N-(hepthyl(urea); F-1394 ((1s,2s)-2[3-(2,2-dimethylpropyl)-3-nonylureido]aminocyclohexane-1-yl3[N-(2,2,5,5-tetramethyl-1,3-dioxane-4-carbonylamino]propionate); CP-113818 (N-(2,4-bis(methylthio)-6-methylpyridin-3-yl)-2-(hexylthio)decanoic acid amide); YM-750; torcetrapib; anacetrapid; JTT-705 (Japan Tobacco/Roche); abciximab; eptifibatide; tirofiban; roxifiban; variabilin; XV 459 (N(3)-(2-(3-(4-formamidinophenyl)isoxazolin-5-yl)acetyl)-N(2)-(1-butyloxycarbonyl)-2,3-diaminopropionate); SR 121566A (3[N-{4-[4-(aminoiminomethyl)phenyl]-1,3-thiazol-2-yl}-N-(1-carboxymethylpiperid-4-yl) aminol propionic acid, trihydrochioride); FK419 ((S)-2-acetylamino-3-[(R)-[1-[3-(piperidin-4-yl) propionyl] piperidin-3-ylcarbonyl] amino] propionic acid trihydrate); clopidogrel; prasugrel; cangrelor; AZD6140 (AstraZeneca); MRS 2395 (2,2-Dimethyl-propionic acid 3-(2-chloro-6-methylaminopurin-9-yl)-2-(2,2-dimethyl-propionyloxymethyl)-propyl ester); BX 667 (Berlex Biosciences); BX 048 (Berlex Biosciences); darapladib (SB 480848); SB-435495 (GlaxoSmithKline); SB-222657 (GlaxoSmithKline); SB-253514 (GlaxoSmithKline); A-81834 (3-(3-(1,1-dimethylethylthio-5-(quinoline-2-ylmethoxy)-1-(4-chloromethylphenyl)indole-2-yl)-2,2-dimethylpropionaldehyde oxime-O-2-acetic acid; AME103 (Amira); AME803 (Amira); atreleuton; BAY-x-1005 ((R)-(+)-alpha-cyclopentyl-4-(2-quinolinylmethoxy)-Benzeneacetic acid); CJ-13610 (4-(3-(4-(2-Methyl-imidazol-1-yl)-phenylsulfanyl)-phenyl)-tetrahydro-pyran-4-carboxylic acid amide); DG-031 (DeCode); DG-051 (DeCode); MK886 (1 [(4-chlorophenyl)methyl]3-[(1,1-dimethylethyl)thio]-α,α-dimethyl-5-(1-methylethyl)-1H-indole-2-propanoic acid, sodium salt); MK591 (3-(1-4[(4-chlorophenyl)methyl]-3-[(t-butylthio)-5-((2-quinoly)methoxy)-1H-indole-2]-, dimehtylpropanoic acid); RP64966 ([4-[5-(3-Phenyl-propyl)thiophen-2-yl]butoxy] acetic acid); SA6541 ((R)-S-[[4-(dimethylamino)phenyl]methyl]-N-(3-mercapto-2methyl-1-oxopropyl-L-cycteine); SC-56938 (ethyl-1-[2-[4-(phenylmethyl)phenoxy] ethyl]-4-piperidine-carboxylate); VIA-2291 (Via Pharmaceuticals); WY-47,288 (2-[(1-naphthalenyloxy)methyl]quinoline); zileuton; ZD-2138 (6-((3-fluoro-5-(tetrahydro-4-methoxy-2H-pyran-4yl) phenoxy)methyl)-1-methyl-2(1H)-quinlolinone); or combinations thereof In some embodiments, the drug is an agent that modulates death (e.g., via apoptosis or necrosis) of a cell. In some embodiments, the drug is a cytotoxic agent. In some embodiments, the drug is maytansine, methotrexate (RHEUMATREX®, Amethopterin); cyclophosphamide (CYTOXAN®);thalidomide (THALIDOMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; or a combination thereof. In some embodiments, the drug is a pro-apoptotic agent. In some embodiments, the drug is an anti-apoptotic agent. In some embodiments, the drug is selected from: minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (542-Amino-4-pyrimidinyl)-4-(4-fluorophenyl)-1-(4-piperidinlyl)imidazole); D-JNKI-1 ((D)-hJIP175-157-DPro-DPro-(D)-HIV-TAT57-48); AM-111 (Auris); SP600125 (anthra[1,9-cd]pyrazol-6(2H)-one); JNK Inhibitor I ((L)-HIV-TAT48-57-PP-JBD20); JNK Inhibitor III ((L)-HIV-TAT47-57-gaba-c-Junδ33-57); AS601245 (1,3-benzothiazol-2-yl (2-[[2-(3-pyridinyl) ethyl] amino]-4 pyrimidinyl) acetonitrile); JNK Inhibitor VI (H2N-RP-KRPTTLNLF-NH2 (SEQ ID NO: 7)); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4, 5,6,7-tetrahydro-1-benzothien-2-yl)-1-naphthamide); dicumarol (3,3'-Methylenebis(4-hydroxycoumarin));

SC-236 (4-[5-[4-chlorophenyl)-3-(trifluoromethyl)-1H-pyrazol-1-yl]benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel Blocker ((±)-1-(3,6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM(L) (Fas apoptosis inhibitory molecule-long); Fas:Fc; FAP-1; NOK2; F2051; F1926; F2928; ZB4; Fas M3 mAb; EGF; 740 Y-P; SC 3036 (KKHTDDGYMPMSPGVA (SEQ ID NO: 8)); PI 3-kinase Activator (Santa Cruz Biotechnology, Inc.); Pam3Cys ((S)-(2,3-bis(palmitoyloxy)-(2RS)-propyl)-N-palmitoyl-(R)-Cys-(S)-Ser(S)-Lys4-OH, trihydrochloride); Act1 (NF-kB activator 1); an anti-IkB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKK-TALDWSWLQTE (SEQ ID NO: 9)); NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVLLALLAPVQRKRQKLMP (SEQ ID NO: 10)); Oridonin; Parthenolide; PPM-18 (2-Benzoylamino-1,4-naphthoquinone); Ro106-9920; Sulfasalazine; TIRAP Inhibitor Peptide (RQIKIWFNRRMKWK-KLQLRDAAPGGAIVS (SEQ ID NO: 11)); Withaferin A; Wogonin; BAY 11-7082 ((E)3-[(4-Methylphenyl)sulfonyl]-2-propenenitrile); BAY 11-7085 ((E)3-[(4-t-Butylphenyl) sulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (-[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo [2,1-b]thiazole dihydrochloride); SB-200646 (N-(1-Methyl-1H-indol-5-yl)-N'-3-pyridinylurea); CMPD-1 (2'-Fluoro-N-(4-hydroxyphenyl)-[1,1'-biphenyl]-4-butanamide); EO-1428 ((2-Methylphenyl)-[4-[(2-amino-4-bromophl)nyeamino]-2-chlorophenyl]methanone); SB-253080 (4-[5-(4-Fluorophenyl)-244-(methylsulfonyl) phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)-); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-VAD-FMK (Benzyloxycarbonyl-Val-Ala-Asp(OMe)-fluoromethylketone); z-LEHD-FMK (benzyloxycarbonyl-Leu-Glu(OMe)-His-Asp(OMe)-fluoromethylketone) (SEQ ID NO: 12); B-D-FMK (boc-aspartyl(Ome)-fluoromethylketone); Ac-LEHD-CHO (N-acetyl-Leu-Glu-His-Asp-CHO) (SEQ ID NO: 13); Ac-IETD-CHO (N-acetyl-Ile-Glu-Thr-Asp-CHO) (SEQ ID NO: 14); z-IETD-FMK (benzyloxycarbonyl-Ile-Glu(OMe)-Thr-Asp (OMe)-fluoromethylketone) (SEQ ID NO: 15); FAM-LEHD-FMK (benzyloxycarbonyl Leu-Glu-His-Asp-fluoromethyl ketone) (SEQ ID NO: 16); FAM-LETD-FMK (benzyloxycarbonyl Leu-Glu-Thr-Asp-fluoromethyl ketone) (SEQ ID NO: 17); Q-VD-OPH (Quinoline-Val-Asp-CH2-O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-α (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4', 6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperzainyl)methyl)-3, 4-dihydro-2,5,7,8-tetramethyl-2H-1-benzopyran-6-ol.2HCl); β-1'-5-methyl-nicotinamide-2'-deoxyribose; β-D-1'-5-methyl-nicotinamide-2'-deoxyribofuranoside; β-1'-4,5-dimethyl-nicotinamide-2'-de-oxyribose; β-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3, 4-d]pyrimidin-4-amine); Lavendustin A (5-[[(2,5-Dihydroxyphenyl)methyl][(2-hydroxyphenyl)methyl] amino]-2-hydroxybenzoic acid); MNS (3,4-Methylenedioxy-b-nitrostyrene); PP1 (1-(1,1-Dimethylethyl)-1-(4-methylphenyl)-1H-pyrazolo[3, 4-d] pyrimidin-4-amine); PP2 (3-(4-chlorophenyl) 1-(1,1-dimethylethyl)-1H-pyrazolo[3,4-d]pyrimidin-4-amine); KX-004 (Kinex); KX-005 (Kinex); KX-136 (Kinex); KX-174 (Kinex); KX-141 (Kinex); KX2-328 (Kinex);

KX-306 (Kinex); KX-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl)ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphneyl)-2-(6-(4-(2-hydroxyethyl)-piperazin-1-yl)-2-methylpyrimidin-4-ylamino) thiazole-5-carboxamide); GN963 (trans-4-(6,7-di methoxyquinoxalin-2ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

Pharmaceutical Compositions

Disclosed herein, in certain embodiments, are pharmaceutical compositions comprising a selective transport molecule disclosed herein. Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

In certain embodiments, a pharmaceutical composition disclosed herein further comprises a pharmaceutically acceptable diluent(s), excipient(s), or carrier(s). In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, or local) administration.

Formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

EXAMPLES

Example 1: Peptide Synthesis

A number of peptides whose cell uptake could be modulated were synthesized. The following symbols, where used, are used with the indicated meanings: Fl=fluorescein aca=ahx=X=aminohexanoyl linker (—HN—(CH2)5-CO-) aminohexanoyl, C=L-cysteine, E=L-glutamate, R=L-arginine, D=L-aspartate, K=L-lysine, A=L-alanine, r=D-arginine, c=D-cysteine, e=D-glutamate, P=L-proline, L=L-leucine, G=glycine, V=valine, I=isoleucine, M=methionine, F=phenylalanine, Y=tyrosine, W=tryptophan, H=histidine, Q=glutamine, N=asparagine, S=serine, T=threonine, o is 5-amino-3-oxapentanoyl linker, and C(me) is S-methylcysteine.

In sequences discussed below, lower case letters indicate the D isomer of the amino acid.

Peptides were synthesized on a peptide synthesizer (Pioneer Peptide Synthesis System by Applied Biosystems) using solid phase synthesis method and commercial available Fmoc amino acids, resins, and the other reagents. The peptides were cleaved with TFA/thioanisole/triisopropylsilane or TFA/thioanisole/triisopropylsilane/ethanedithiol.

Peptides were labeled with 5-(and-6)carboxyfluorescein succinimidyl ester on the amino group on the peptide or with 5-iodoacetamidofluorescein on the thiol group on the peptide.

The crude peptide was purified on HPLC and lyophilized overnight.

Each peptide composition was confirmed by mass spectrometry.

Synthesis of a Selective Transport Molecule (Hereinafter, Peptide 1)

Suc-e$_8$-(Aop)-PLGC(me)AG-r$_9$-c-NH$_2$ was synthesized via standard Fmoc solid phase peptide synthesis. The N-terminal succinyl group was added to the peptide by reaction with succinic anhydride while still on resin. The peptide was cleaved from the resin in a standard cocktail (trifluoroacetic acid with 2% each of thioanusole, triisopropylsilane and ethandithiol) overnight at room temperature. Most of the trifluoroacetic acid was remove by rotary evaporator, 50% hexanes in diethyl ether was added and the peptide was collected by centrifugation. The collected solid was washed with 50% hexanes in ether three times and vacuum dried overnight. The peptide was purified on HPLC using 15%-30% acetonitrile in water and 0.05% TFA, giving a 30% yield from the crude peptide. The correct purified product was confirmed by electrospray mass spectroscopy: calculated 3271.5 Da, found 3271.8 Da.

Synthesis of Peptide-Labeled Dendrimer 2

25 mg of peptide 1 was dissolved in 2 mL DMSO under N$_2$ and was reacted with 2.3 mg 2-nitro-4-sulfophenyl 6-maleimidohexanoate sodium salt and 20 µL N-methylmorpholine. After stirring at room temperature for three hours, LC-MS analysis of the reaction mixture indicated over 90% completion. The reaction mixture was cooled to 0°, 150 mg PAMAM dendrimer and 2 mL 1 M Hepes buffer (pH 7.8) were added and stirred at 5° for 2 days (hereinafter, reaction mixture 2).

Synthesis of Cy5- and Peptide-Labeled Dendrimer 3.

1.2 mg Cy5 mono(N-hydroxysuccinimide) was added to reaction mixture 2 and stirred at 5° overnight (hereinafter, reaction mixture 3).

Synthesis of Capped Cy5- and Peptide-Labeled Dendrimer 4.

166 mg of MeO(CH$_2$CH$_2$O)$_3$CH$_2$CH$_2$CO—(N-hydroxysuccinimide)ester was added to reaction mixture 3 at 5° and stirred at that temperature for 3 days. The crude product was diluted with 10 mL of water, and low molecular weight contaminants were removed by filtration 8 times through a membrane with a 10 kDa cutoff. HPLC using a size-exclusion column indicated 99% purity, 72% yield. An average of 3 fluorophores per dendrimer was determined by dissolving a known weight of purified final product in water and measuring Cy5 absorbance at 650 nm, assuming an extinction coefficient of 250,000M$^{-1}$ cm$^{-1}$. Static multiangle light-scattering at 785 nm indicated an apparent molecule weight of 72.9 kDa. Dynamic light scattering at 785 nm indicated a hydrodynamic radius of 4.6 nm.

Synthesis of DOTA-, Cy5- and Peptide-Labeled Dendrimer 5.

30 equivalents of DOTA mono-N-hydroxysuccinimde ester in HEPES buffer were reacted with reaction mixture 3 and stirred at 5° overnight (hereinafter, reaction mixture 5).

Synthesis of Capped DOTA-, Cy5- and Peptide-Labeled Dendrimer 6.

Reaction mixture 5 was reacted with 950 equivalents mPEG4 NHS and stirred at 5° for three days. The crude product was purified as described for capped Cy5- and peptide-labeled dendrimer 4, then lyophilized. The yield was 78%.

Gd Loading of Capped DOTA-, Cy5- and Peptide-Labeled Dendrimer 6

25 mg of capped DOTA-, Cy5- and peptide-labeled dendrimer 6 was dissolved in 1 mL 0.5M ammonium acetate and 1 mL water. The reaction mixture was mixed with 100 µL 0.5 GdCl$_3$ and stirred at room temperature for 3 days shielded from light. Small molecules were eliminated by 5 aqueous washes. Excess water was removed by centrifugation through a membrane filter with a 10 kDa cutoff. Finally, the Gd loaded product 7 was lyophilized overnight to give a blue fluffy solid. The pure product was weighed and redissolved in water to give a 200 uM solution. A measured small aliquot was mixed with 0.5 mL concentrated nitric acid for 2 hours. Gd quantitation was determined by inductively coupled plasma mass spectroscopy, which indicated an average of 15 Gd per dendrimer. The number of Cy5 labels per dendrimer was confirmed to be 3 based on 650 nm absorbance.

Example 2: In Vivo Fluorescence Imaging of Atherosclerotic Plaques with Selective Transport Molecules Peptide Synthesis Briefly, peptides were synthesized on an automatic peptide synthesizer following standard procedures for fluorenylmethoxycarbonyl solid-phase synthesis. Peptides were N-terminally capped with a succinate and C-termini were amidated. After cleavage off the resin, the C-termini were labeled through the cysteine with Cy5or rhodamine monomaleimide. Peptides were purified using HPLC. Specific peptide compositions were: DPRSFL (SEQ ID NO: 1)-based transport molecule=Suc-e9-O-DPRSFL-r9-c(Cy5 or rhodamine)-CONH2), DPRSFL (SEQ ID NO: 1)-based transport molecule=(Suc-e9-ahx-dprsfl-r9-c(Cy5)-CONH2), and mPEG-selective transport molecule=(Suc-e9-(mPEG)-r9-c(Cy5)-CONH2) where ahx=aminohexanoic acid, 0=5-amino-3-oxapentanoyl and mPEG=(PEG$_2$)$_2$. Lower case letters represent D-amino acids.

Determination of k$_{cat}$/k$_m$

Reactions containing 50 nM thrombin, and seven peptide concentrations ranging from 1 to 30 µM DPRSFL-based transport molecule peptide were incubated for 5, 15, 30 and 60 minutes in 100 µL reaction volumes before undergoing tricine gel electrophoresis. Reactions were stopped by addition of SDS containing sample buffer at the appropriate time point. Percent cleavage was assessed as before, and was multiplied by the starting concentration for each vial to obtain the total product concentration. The velocity of each reaction was obtained by determination of the slope of the linear portion of the curve on a scatterplot comparing product vs. time. The k$_{cat}$ and k$_m$ were obtained by determining the y-intercept and slope on a Lineweaver-Burke plot.

Serum Cleavage Experiments

Whole blood was collected either via cardiac puncture or from the abdominal aorta, in either heparinized tubes (plasma) or eppendorf tubes (serum). Both tubes were centrifuged at low speeds to pellet out the red blood cells, and the supernatant was removed and frozen for future use. Cleavage assays were done using a final concentration of between 2 and 5 µM peptide. Argatroban (Enzo Life Sciences Plymouth Meeting, Pa.) and lepirudin (UCSD Hillcrest Hospital pharmacy and were used at a final concentration of 4 mg/mL and 0.5 mg/mL respectively. After 20 minutes, reactions were stopped by addition of SDS containing tricine sample buffer and heating to 85° C. Cleavage was assayed by tricine gel electrophoresis at 100V (Invitrogen, Carlsbad, Calif.), and bands were quantified by integrated density using Image J. Percent cleavage and total observed cleavage were calculated as before.

Methods for Enzyme Panel

Enzymes were purchased from commercial sources: recombinant plasmin, Factor VIIa, trypsin, chymotrypsin, thrombin, Factor XIa, Factor XIIa, cathepsin G, neutrophil elastase, and activated protein C (APC) were purchased from EMD, La Jolla Calif., Factor Xa from NEB, Ipswitch, Mass., pancreatic elastase from Sigma Aldrich. 5 uM substrate was incubated with 50 nM and rate of cleavage was determined by the emergence of a lower molecular weight band on commercially prepared tricine gel electrophoresis (Invitrogen). Band intensity was quantified using Image J, with "background" defined as the average of a larger area in the middle of the gel, away from any fluorescence bands. This "background" is due to CCD noise. Percent cleavage was defined as (intensity of the lower molecular weight band minus "background")/(intensity of lower plus higher molecular weight band minus 2 times background). To account for minor impurities in the sample, the percent cleavage for uncleaved substrate has been subtracted off (FIG. S1)

Ex Vivo Clot Aging Experiments

Blood was obtained from mice (n=3) or rats (n=1) via cardiac puncture and allowed to clot in an Eppendorf tube. Small clots (~30-60 mg) were cut off for processing at each time point. Clots were stored in a humidified chamber prior to use. At the indicated time point, clots were incubated for 10 minutes in either 2.5 and 5 µM DPRSFL (SEQ ID NO: 1)-based transport molecule with or without addition of argatroban or lepirudin (4 mg/mL and 0.5 mg/mL final concentrations respectively) or mPEG-selective transport molecule. At least two clots were assayed for each time point for each animal. After staining, clots were washed three times in 2 mL PBS with shaking. Clots were then imaged using a fluorescence mouse imager (CRI, Maestro, ex 640/48, em 700 nm). Data were quantified by taking the average intensity of the entire clot in Image J. Each condition was compared to the result for DPRSFL-based transport molecule alone, and significance was assessed using an unpaired, two-tailed Students t-test.

Animals and Preparation of In Vivo Clots

Wildtype FVB mice (n=12) were obtained from Charles River (Wilmington, Mass.). Tails were amputated 2.5 mm from the tip. Following tail amputation, 10 nmol of either DPRSFL-based transport molecule or mPEG-selective transport molecule was injected intravenously. Mice were anesthesitized with ketamine/midazolam (80 mg/kg, 5 mg/kg) and tails were imaged using a Zeiss Lumar dissecting microscope (ex 620/60, em 700/75, 0.8× objective, Zeiss, Peabody, Mass.). Significance was assessed using an unpaired two-tailed Students t-test. All animal procedures were approved by UCSD's institutional animal care and use committee.

Atherosclerosis Models $LDLR^{-/-}$ or $ApoE^{-/-}$ mice were fed a high cholesterol diet (0.5-2%) for 1-2 years prior to the experiment, generating animals with moderate to severe atherosclerotic lesions[42]. Animals were used once they were about to be sacrificed for health reasons ranging from skin ulcerations to the sudden overnight death of cage-mates. For a more complete breakdown of the study population including ages, duration of diet, gender and genotype, see Table S1 and S2 Inhibitors used were recombinant hirudin at 2000 U/mouse (EMD Biosciences), and a cocktail of SB3CT (500 µg/animal) and GM6001 (2 mg/animal).

Imaging of Aortas

Animals were injected with either mPEG-selective transport molecule or DPRSFL-based transport molecule with or without pre-injection 250 µg recombinant hirudin (EMD Biosciences). Probe was allowed to circulate for six hours. To obtain aorta for imaging of whole vessel fluorescence, mice were transcardially perfused with saline followed by buffered formaldehyde. Whole aorta were dissected from the level of the aortic arch to the abdominal aorta and then bisected for pinning onto wax for fluorescent imaging of bound selective transport molecules using a Maestro Imager™ ((700 nm) using a 640/48 excitation filter) (Cri, Woburn Mass.). Percent plaque and plaque intensity were calculated using Amira software (Visage Imaging, La Jolla, Calif.), FIG. S1. To account for day-to-day variation in light levels, for each experiment plaque intensity is reported as raw plaque intensity/phantom intensity taken on the same day (Labsphere certified reflectance standard, North Sutton, N.H.).

AHA Plaque Stage Determination

For histopathology preparation, aortic arch samples with plaque discernable with white light illumination were collected and cryoprotected in 30% (w/v) buffered sucrose. Samples were frozen in Tissue-Tek embedding medium (Torrance Calif.). Each block was sectioned at 10 µm thickness and sections were thaw mounted onto glass slides; adjacent slides were stained with hematoxylin/eosin (H/E) or with the Gomori Trichrome method. Slides were imaged dry on a Zeiss Lumar dissecting microscope (ex 620/60, em 700/75, 1.5x objective). Histological interpretation and categorization of arterial sections including the vessel wall was performed by a blinded, board certified pathologist (SB). Significance between results from AHA Class 5 vs. AHA Class 6 was determined by two tailed, unpaired Students t-test.

Whole Animal Imaging

Animals were briefly anesthetized with ketamine/midazolam (80 mg/kg, 5 mg/kg) and co-injected with the indicated selective transport molecule(s). 18-24 hours later, animals were anesthetized by injection of ketamine (80 mg/kg) and midazolam (5 mg/kg) or euthanized by an overdose of the same two drugs. The carotid artery was exposed pre-mortem and was imaged using a custom surgical apparatus in our lab. Other structures including the carotid bifurcation and the aortic arch were exposed post-mortem and were imaged using a Zeiss Lumar dissecting microscope (ex 560/25, em 607/36 for rhodamine, ex 620/60, em 700/75 for Cy5, 0.8x objective, Zeiss, Peabody, Mass.). After imaging, tissue was frozen on dry ice for histology.

Fresh Frozen Tissue Histology

Frozen tissue was cut to 10 µm and imaged dry using a Zeiss Lumar dissecting microscope ex 560/25, em 607/36 for rhodamine, ex 620/60, em 700/75 for Cy5, 1.5x objective). Overlays were done using Metamorph software (Molecular Devices, Sunnyvale, Calif.).

Immunocytochemistry

Mice were euthanized with an overdose of ketamine-midazolam.

Immunochemistry was performed on fresh aorta specimen dissected from euthanized mice and immediately snap frozen with dry ice in Tissue-tek filled molds. Cryostat sections (10 µm thick) were incubated with anti-F4/80 (clone BM8) (14-4801-81 e-Bioscience, San Diego) to visualize macrophages. For identification of macrophages as well as other myeloid cells, sections were incubated with antibodies to CD68 (ab 53444-100, Abcam, Cambridge, Mass.). After a 48 hour incubation the bound primary antibody was visualized with biotinylated secondary antibody (AP183B, Millipore, Temecula Ca) followed by treatment with avidin-biotinylated peroxidase (RTU Vectastain, Vector labs Burlingame Calif.) and diaminobenizdine (Vector labs, Burlingame Calif.). Alternate sections that were not immunoreacted were imaged with epifluorescence microscopy to visualize the distribution of fluorescent selective transport molecule.

Human Specimen

Postoperative human endarterectomy specimens were obtained at UCSD from Drs. Nikhil Kansal, Erik Owens and Katherine Brown (UCSD IRB#080965). Specimens were transported from the operating room to our lab in approximately 5 minutes, where they were embedded in 0.5% agarose gel and cut into 2 mm sections. Sections were incubated in a 96-well plate for 1 hour in 10 mM of either DPRSFL (SEQ ID NO: 1)-based transport molecule, PLGLAG (SEQ ID NO: 4)-selective transport molecule or mPEG-selective transport molecule as described above and washed six times for 15 minutes in PBS prior to embedding in Cryotec and freezing at −80 C. 8 nm cryostat sections were cut and mounted onto glass slides. Imaging was done using the Zeiss Lumar microscope (ex 620/60, em 700/75, 0.8x objective, 8× magnification). Data was collected using MetaMorph software version 6.1 (Silicon Valley, Calif.). Quantification of fluorescence intensity was performed using ImageJ software (NIH, Bethesda, Md.). Average background fluorescence and fluorescence intensity were measured and background subtracted (FIG. S6). Since the specimens were collected over 6-8 months and the same atheromas were used to test experimental and control selective transport molecules, both unpaired and matched-paired t-tests were used to compare relative fluorescence intensity, with significance defined as p<0.05.

DPRSFL (SEQ ID NO: 1)-Based Transport Molecule is a Novel Selective Transport Molecule that is Cleavable by Thrombin and Serum Derived from Whole Blood.

Figure 2:
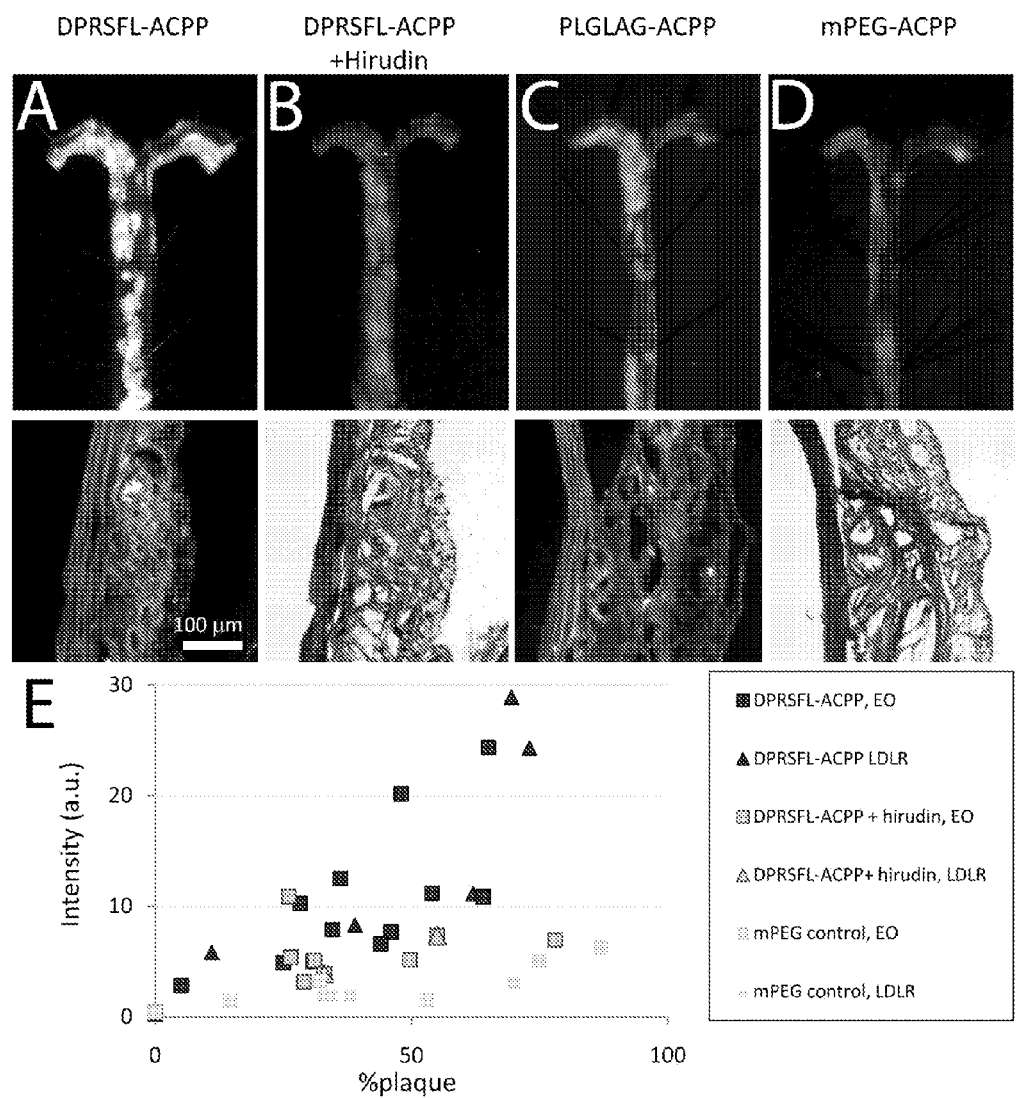
FIG. 2. DPRSFL(SEQ ID NO: 1)-based transport molecule and PLGLAG (SEQ ID NO: 4)-selective transport molecule uptake are enzyme dependent and correlate with increased plaque burden in atherosclerotic mice. A-D: Representative fluorescence images of gross aortas removed from animals six hours after injection with 10 nmol DPRSFL (SEQ ID NO: 1)-based transport molecule (A), 10 nmol DPRSFL (SEQ ID NO: 1)-based transport molecule 45 minutes after injection with 250 µg hirudin (B), 10 nmol PLGLAG (SEQ ID NO: 4)-selective transport molecule and 10 nmol mPEG control selective transport molecule (D), showing enzyme specific uptake. E-H: Fluorescence (E and G) and Gamori trichrome (F and H) micrographs of paraformaldehyde fixed plaques from animals injected with DPRSFL (SEQ ID NO: 1)-(E and F) and PLGLAG (SEQ ID NO: 4)-selective transport molecule (G and H). I: Scatter plot comparing average uptake of DPRSFL (SEQ ID NO: 1)-based transport molecule in ApoE (solid symbols) and LDLR (hollow symbols) deficient mice with the total plaque burden, or percentage of each aorta covered in plaque. Uptake of the DPRSFL (SEQ ID NO: 1)-based transport molecule was largely inhibited in animals pre-injected with hirudin, especially in aortas with increased plaque burden.

We first used purified thrombin to determine whether two candidate thrombin cleavage sites found in the literature would be selective for thrombin once bent into the typical selective transport molecule hairpin configuration (14). The first cleavage site tested, Norleucine-TPR, came from a screen for fluorogenic substrates for thrombin using a positional scanning library (32) and was barely cleavable by purified thrombin after insertion into the selective transport molecule hairpin. The second, DPRSFL (SEQ ID NO: 1), is comprised of amino acids 39-44 of the PAR-1 thrombin receptor (FIG. 1A,28). Since activation of this receptor by thrombin through cleavage of the DPRSFL (SEQ ID NO: 1) sequence is involved in a wide range of pathological processes, we hypothesized that this new selective transport molecule should be reasonably selective for thrombin activity in vivo. As expected, DPRSFL (SEQ ID NO: 1)-based transport molecule was efficiently cleaved by purified thrombin in vitro with a $k_{cat/km}$ of $2.1\times10^4$. This is slower than thrombin cleavage of the native PAR-1 receptor ($k_{cat}/k_m$ of $7.6\times10^6$(26)), likely due to bending of the substrate sequence secondary to the hairpin shaped selective transport molecule (14) and removal of the hirudin binding domain (27). Incubation in active serum also resulted in rapid cleavage of the DPRSFL (SEQ ID NO: 1)-based transport molecule. Serum cleavage was completely inhibitable by thrombin inhibitors such as lephirudin and argatroban, suggesting that thrombin is responsible for cleavage even in this complex mixture of coagulation enzymes. No cleavage was seen upon incubation of the DPRSFL (SEQ ID NO: 1)-based transport molecule in plasma, or anticoagulated blood that should not contain active thrombin (FIG. 1B, FIG. S1)

DPRSFL (SEQ ID NO: 1)-Based Transport Molecule is Cleaved by Several Commercially Available Enzymes Known to Cleave the PAR-1 Receptor.

Several other enzymes are known to cleave the PAR-1 receptor in vitro, though less efficiently than thrombin. To determine the specificity of the DPRSFL (SEQ ID NO: 1) cleavage site for thrombin, a panel of commercially available enzymes was tested for cleavage of DPRSFL (SEQ ID NO: 1)-based transport molecule. As expected, several of these enzymes known to cleave the native PAR-1 receptor at the DPRSFL (SEQ ID NO: 1) cleavage site were able to cleave the DPRSFL (SEQ ID NO: 1)-based transport molecule, including thrombin, plasmin, Factor Xa, trypsin and chymotrypsin. (FIG. 1C). In separate tests, coagulation factors VIIa, IXa, XIa and XIIa, elastase, MMP's 2, 7 and 9, cathepsin, renin, uPA and tPA did not cleave the DPRSFL (SEQ ID NO: 1)-based transport molecule efficiently. Taken together with the inhibitor data shown previously, these data support the hypothesis that thrombin is most likely responsible for cleavage of DPRSFL (SEQ ID NO: 1)-based transport molecule in active serum and confirm that direct thrombin inhibitors are a useful method for verifying that selective transport molecule cleavage and uptake is due to thrombin in new model systems.

DPRSFL (SEQ ID NO: 1)-Based Transport Molecule is Cleaved and Taken Up into Blood Clots Using Either In Vitro or In Vivo Clot Models.

To determine whether DPRSFL (SEQ ID NO: 1)-based transport molecule cleavage caused uptake of the cleaved fragment into blood clots, fresh clots were created postmortem by allowing blood to clot onto glass. Similarly sized clots were incubated in DPRSFL (SEQ ID NO: 1)-based transport molecule with and without direct thrombin inhibitors and labeling was compared to that of a control selective transport molecule containing an inert $(PEG_2)_2$ linker replacing the DPRSFL (SEQ ID NO: 1) cleavage site (mPEG-selective transport molecule, 15). Since selective transport molecule's have no quenching mechanism, it was necessary to wash clots extensively after incubation in probe to disperse uncleaved selective transport molecule. The DRPSFL (SEQ ID NO: 1)-selective transport molecule showed between a two and six-fold increase in signal when compared to uptake of the control selective transport molecule. Uptake of DPRSFL (SEQ ID NO: 1)-based transport molecule was completely inhibitable by addition of either lephirudin or argatroban prior to clot incubation with probe (FIG. S2). In a separate set of experiments, an in vivo tail amputation model [33] was used to test whether the DPRSFL (SEQ ID NO: 1)-based transport molecule highlighted clots formed in vivo. We injected 10 nmols of either DPRSFL (SEQ ID NO: 1)-based transport molecule or mPEG-selective transport molecule twenty minutes or six hours following tail amputation. Uptake of DPRSFL (SEQ ID NO: 1)-based transport molecule was 1.9 to 2.4-fold greater than mPEG-selective transport molecule (FIG. S3), with no significant difference in uptake between time points. [[.]]

DPRSFL (SEQ ID NO: 1)-Based Transport Molecule and PLGLAG (SEQ ID NO: 4)-Selective Transport Molecule Uptake was Enzyme Dependent and Correlated with Increased Plaque Burden in Atherosclerotic Mice.

Atherosclerosis was studied in aged transgenic mice deficient in either ApoE ($ApoE^{-/-}$) or LDLR ($LDLR^{-/-}$) that had been maintained on a prolonged high-fat diet. Many of the animals with higher plaque burden were clinically ill at time of use, and their disease had progressed to such a point that they would have been sacrificed for health reasons had they not been included in this study. Animals were injected with DPRSFL (SEQ ID NO: 1)-based transport molecule alone (FIG. 2A), DPRSFL (SEQ ID NO: 1)-based transport molecule with pre-injection of hirudin (FIG. 2B), MMP cleavable PLGLAG (SEQ ID NO: 4)-selective transport molecule (FIG. 2C) or with negative control peptide mPEG-selective transport molecule (FIG. 2D). Representative plaques with Gamori trichrome stains on adjacent sections are shown for DPRSFL (SEQ ID NO: 1)-based transport molecule and PLGLAG (SEQ ID NO: 4)-selective transport molecule in FIG. 2E-H. Gross fluorescence uptake was quantitated for whole dissected aortas six hours after injection with selective transport molecule. Both DPRSFL (SEQ ID NO: 1)-based transport molecule and PLGLAG (SEQ ID NO: 4)-selective transport molecule showed a quantitative increase that correlated moderately well with total plaque burden (correlation coefficient 0.8 and 0.85 respectively, FIG. 2E, FIG. S4). For the purpose of analysis, aortas were stratified into three groups based on their overall plaque burden, low (0-30%), medium (30-55%) and high (>55%). We found that while uptake of DPRSFL (SEQ ID NO: 1)-based transport molecule and PLGLAG (SEQ ID NO: 4)-selective transport molecule were similar when plaque burden was low (5.7±2.7 vs. 5.9±2.9, p=0.98), DPRSFL (SEQ ID NO: 1)-based transport molecule was taken up more in animals with high plaque burden (19.9±8.3 vs. 14.7±1.5, p=0.24) FIG. 2A, 2B, 2E, FIG. 5I). Hirudin was effective at inhibiting uptake at high plaque burden, with 85% inhibition when compared to the mPEG control selective transport molecule as baseline. By comparison, MMP inhibitors such as SB3CT and GM6001 reduced uptake of PLGLAG (SEQ ID NO: 4)-selective transport molecule by only 30% in animals with high plaque burden, consistent with previous results using the PLGLAG (SEQ ID NO: 4)-selective transport molecule's in tumors (15). There was very little uptake in the arterial wall of a single wildtype mouse (0.25.), compared to uptake in the grossly plaque free aortic wall in its LDLR and ApoE deficient counterparts (2.2±1.8 a.u.). In contrast, uptake of PLGLAG (SEQ ID NO: 4)-selective transport molecule into the arterial wall of a single wildtype mouse was similar to that of grossly plaque free aortic wall in its LDLR and ApoE deficient counterparts (2.6 vs. 3.0±1.3 a.u.).

Thrombin Specific Uptake is Elevated in High Risk Lesions, Whereas MMP Specific Uptake is not.

Figure 3:
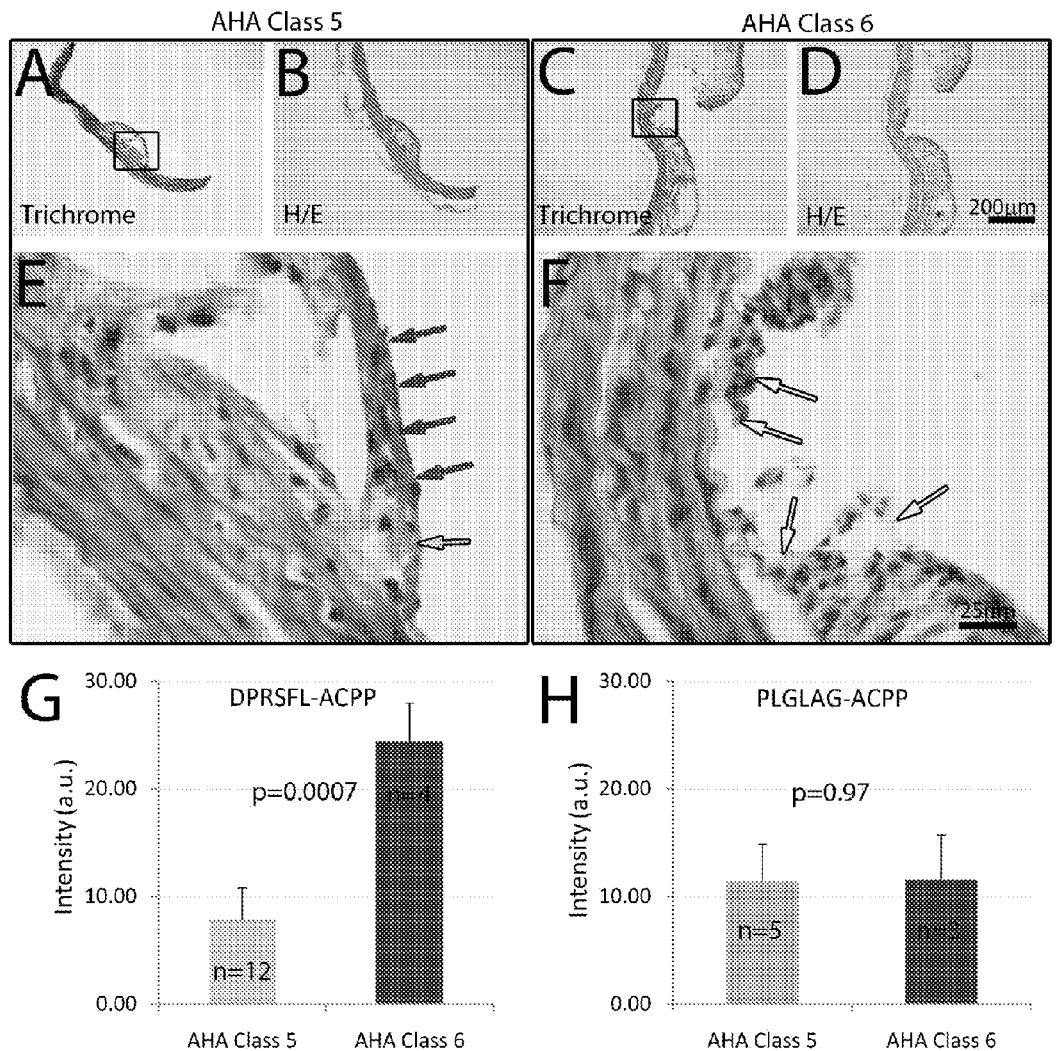
FIG. 3. DPRSFL (SEQ ID NO: 1)-based transport molecule uptake correlates with AHA class and rupture potential in ApoE and LDLR deficient mice. A-D: Light micrographs of H/E (A and C) and trichrome (B and D) stained sections showing two representative lesions. E-F: Higher magnification images of the two sections in A and C. E: Category 5 plaque showing lipid pooling, an intact shoulder (blue arrow) and a thick fibrous cap (red arrows). F: Category 6 plaque displaying increased cellularity (yellow arrows) and an irregular contour indicative of an old thrombus. G-H: bar graphs comparing gross uptake of selective transport molecule with the histopathological AHA class from a representative section. Uptake of the thrombin cleavable DPRSFL (SEQ ID NO: 1)-based transport molecule correlates well with AHA class (G), whereas there is no significant difference between uptake of the MMP cleavable PLGLAG (SEQ ID NO: 4)-selective transport molecule in AHA Class 5 vs. AHA Class 6 lesions (H).

To determine whether high risk lesions correlated with increased thrombin and MMP activity, a representative section of visible plaque from the aortic arch of each mouse was sectioned and stained with H/E and Gomori trichrome. All stained plaques were categorized in a blinded fashion by a board-certified pathologist into AHA Class 1-6 (2). The vast majority of the plaques were either AHA Class 5 (fibrous plaque, FIGS. 3A and B, FIG. 3E) or AHA Class 6 (complicated lesion/rupture, FIGS. 3C and D, FIG. 3F). These AHA category assignments were then used to stratify the gross fluorescence intensity data obtained from whole aortas into those containing higher risk plaques and those containing lower risk plaques. We found that aortas with the highest gross DPRSFL (SEQ ID NO: 1)-based transport molecule uptake were those for which the representative plaque was categorized as a high risk AHA Class 6 (24.4±3.6, n=4). Three out of four of these plaques were from animals that were also in the high plaque group when animals were stratified by plaque burden. In contrast, lower risk AHA Class 5 plaques demonstrated significantly less DPRSFL (SEQ ID NO: 1)-based transport molecule uptake (7.8±3.0, n=12, p=0.0007, FIG. 3G). In contrast, gross PLGLAG (SEQ ID NO: 4)-selective transport molecule uptake was statistically similar between cases with AHA Class 5 (11.4±3.4, n=5) or AHA Class 6 (11.5±4.2, n=3) p=0.97, FIG. 3H).

Localization of Thrombin and MMP Activity is Distinct and Varies Throughout the Course of Plaque Development.

Figure 4:
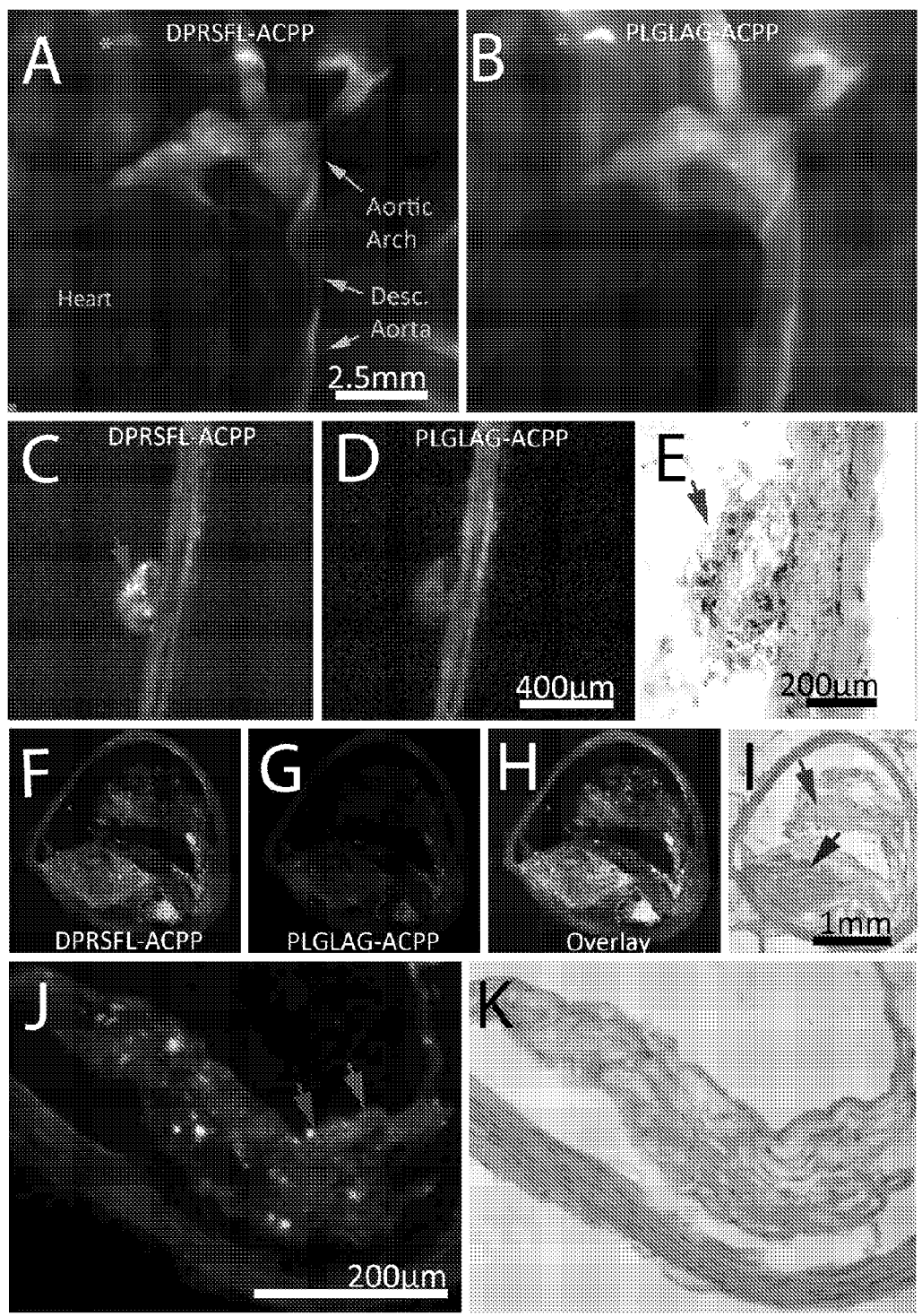
FIG. 4. Dual selective transport molecule labeling of thrombin and MMP activity in atherosclerosis. A and B: Gross fluorescence images from animals taken six hours after co-injection with rhodamine labeled DPRSFL (SEQ ID NO: 1)-based transport molecule (A) and Cy5 labeled PLGLAG (SEQ ID NO: 4)-selective transport molecule (B). Although both selective transport molecules highlight atheromas, uptake of DPRSFL (SEQ ID NO: 1)-based transport molecule highlights specific regions of plaque (red arrow). C-E: Fluorescence histology images showing a small plaque on an otherwise clean vessel wall. The small plaque is highlighted with DPRSFL (SEQ ID NO: 1)-based transport molecule (C), but not with MMP-selective transport molecule (D), suggesting that thrombin may be a better target for visualization of early plaques. H/E staining is shown in (E). F-I: Cross sectional images of aorta showing DPRSFL (SEQ ID NO: 1)-based transport molecule uptake (F), PLGLAG (SEQ ID NO: 4)-selective transport molecule uptake (G) and an overlay (H) with DPRSFL (SEQ ID NO: 1)-based transport molecule uptake shown in red and PLGLAG (SEQ ID NO: 4)-selective transport molecule uptake shown in green in a slice of an advanced plaque showing calcification (blue arrow) and fibrosis (red arrow) on an H/E (I). J-K: A magnified overlay of a difference slice of aorta showing cells taking up DPRSFL (SEQ ID NO: 1)-based transport molecule (green), PLGLAG (SEQ ID NO: 4)-selective transport molecule (red) or both (yellow). Again, the DPRSFL (SEQ ID NO: 1)-based transport molecule also highlights areas of fibrosis (red arrows), identified by H/E staining (K).

To examine differences between localization of thrombin and MMP activity throughout the course of plaque development, two LDLR$^{-/-}$ mice were co-injected with tetramethylrhodamine isothiocyanate (TRITC) labeled DPRSFL (SEQ ID NO: 1)-based transport molecule and Cy5-PLGLAG (SEQ ID NO: 18)-selective transport molecule and sacrificed without perfusion 14-18 hours after injection (FIGS. 4A and B). Following dual wavelength gross imaging, aortas were cryosectioned and examined using dual wavelength fluorescence microscopy. Both mice had extensive, near occlusive, calcified plaque in the aortic arch with histological evidence of rupture in addition to less severe atherosclerotic disease in the descending thoracic aorta. Earlier plaques from the descending thoracic aorta frequently took up DPRSFL (SEQ ID NO: 1)-based transport molecule, but not PLGLAG (SEQ ID NO: 4)-selective transport molecule (FIG. 4C-E). A common finding in more advanced, fibrosing plaques was diffuse uptake of the DPRSFL (SEQ ID NO: 1)-based transport molecule throughout blue fibrotic regions seen on trichrome staining of adjacent sections (FIG. 1E) but not in lipid laden macrophages at the surface of plaques (FIG. S5). Finally, both PLGLAG (SEQ ID NO: 4)-selective transport molecule and DPRSFL (SEQ ID NO: 1)-based transport molecule were frequently taken up into discrete puncta with occasional co-localization (FIG. 4F-K). These puncta did not colocalize with F480 expressing macrophages, although there was some colocalization with the less specific CD68 antigen (FIG. S5). PLGLAG (SEQ ID NO: 4) and DPRSFL (SEQ ID NO: 1)-based transport molecule's detect enzymatic activity in human atheromas.

Figure 5:
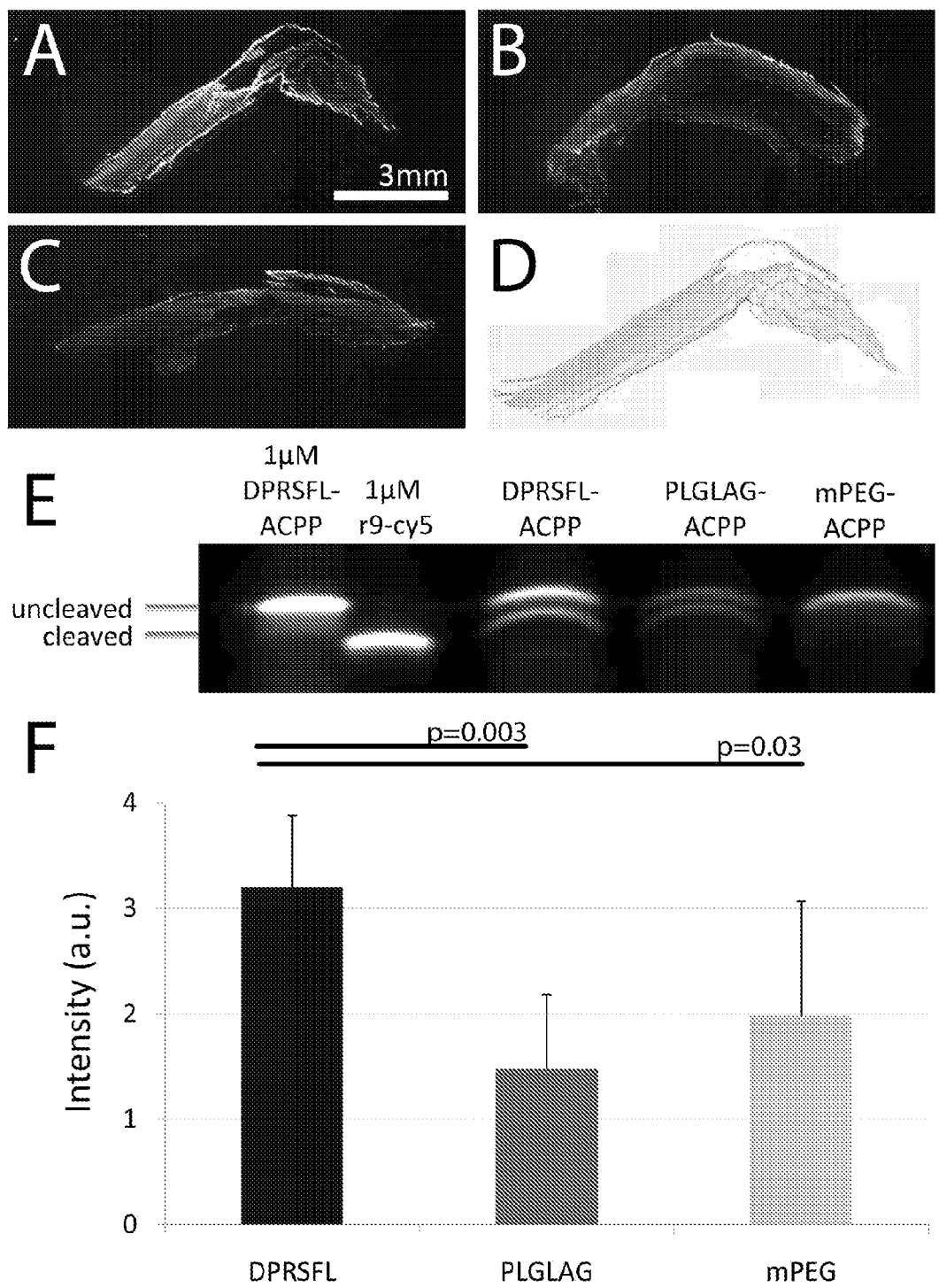
FIG. 5. DPRSFL (SEQ ID NO: 1)-based transport molecule highlights plaques in the carotid arteries of ApoE$^{-/-}$ and LDLR$^{-/-}$ mice. A and B: Brightfield (A) and Cy5 fluorescence micrographs of carotid plaques in mice taken in living mice during a carotid endarterectomy procedure done six hours after injection with I Onmol DPRSFL (SEQ ID NO: 1)-based transport molecule. Plaque barely visible in the intraoperative image (A) is highlighted in the fluorescence image (B). C-G: A fluorescence micrograph taken postmortem of a similar animal following a more extensive surgical exposure of the carotid bifurcation is shown in (C). From this specimen, vessel with (D-E) and without (F-G) highlighted plaques was taken for Cy5 fluorescence histology (D and F) and H/E staining (E and G) that confirmed the presence (E) and absence (G) of plaque. H-J: A similar fluorescence micrograph of a mouse co-injected with rhodamine labeled DPRSFL (SEQ ID NO: 1)-based transport molecule (H) and Cy5 labeled PLGLAG (SEQ ID NO: 4)-selective transport molecule (I) showing improved delineation of the plaque area with the DPRSFL (SEQ ID NO: 1)-based transport molecule. An H/E near the carotid bifurcation showed near occlusion of the carotid artery (J).

Seven atheroma specimen were obtained following carotid endarterectomy. Each specimen was cut into 1-2 mm slices that were then incubated in either PLGLAG (SEQ ID NO: 4)-selective transport molecule, DPRSFL (SEQ ID NO: 1)-based transport molecule or mPEG-selective transport molecule. The slices were then cryosectioned to look at selective transport molecule uptake in the interior of the plaque. Qualitatively, we found that specimens incubated in DPRSFL (SEQ ID NO: 1)-based transport molecule had the highest uptake (FIG. 5A-C). H/E staining confirmed that all of the plaques removed were at least AHA Class 5 (fibroatheroma, FIG. 5D). After incubation supernatants were analyzed by gel electrophoresis. DPRSFL (SEQ ID NO: 1)-based transport molecule was more efficiently cleaved by human atheroma specimens compared to PLGLAG (SEQ ID NO: 4)-selective transport molecule, with no cleavage at all of the control mPEG-selective transport molecule (FIG. 5E). Quantitatively, atheromas incubated with DPRSFL (SEQ ID NO: 1)-based transport molecule were 70% brighter than atheromas incubated in PLGLAG (SEQ ID NO: 4)-selective transport molecule, (p=0.03) or mPEG-selective transport molecule (p=0.002). There was no significant difference between uptake of PLGLAG (SEQ ID NO: 4)-selective transport molecule and mPEG-selective transport molecule (p=0.97, See FIG. S1, Table S3). These results suggest that thrombin may be a more sensitive molecular target than MMP's for targeting advanced human atherosclerotic lesions.

DPRSFL (SEQ ID NO: 1)-Based Transport Molecule can be Used Intraoperatively for Molecular Navigation in Vascular Surgery.

Figure 6:
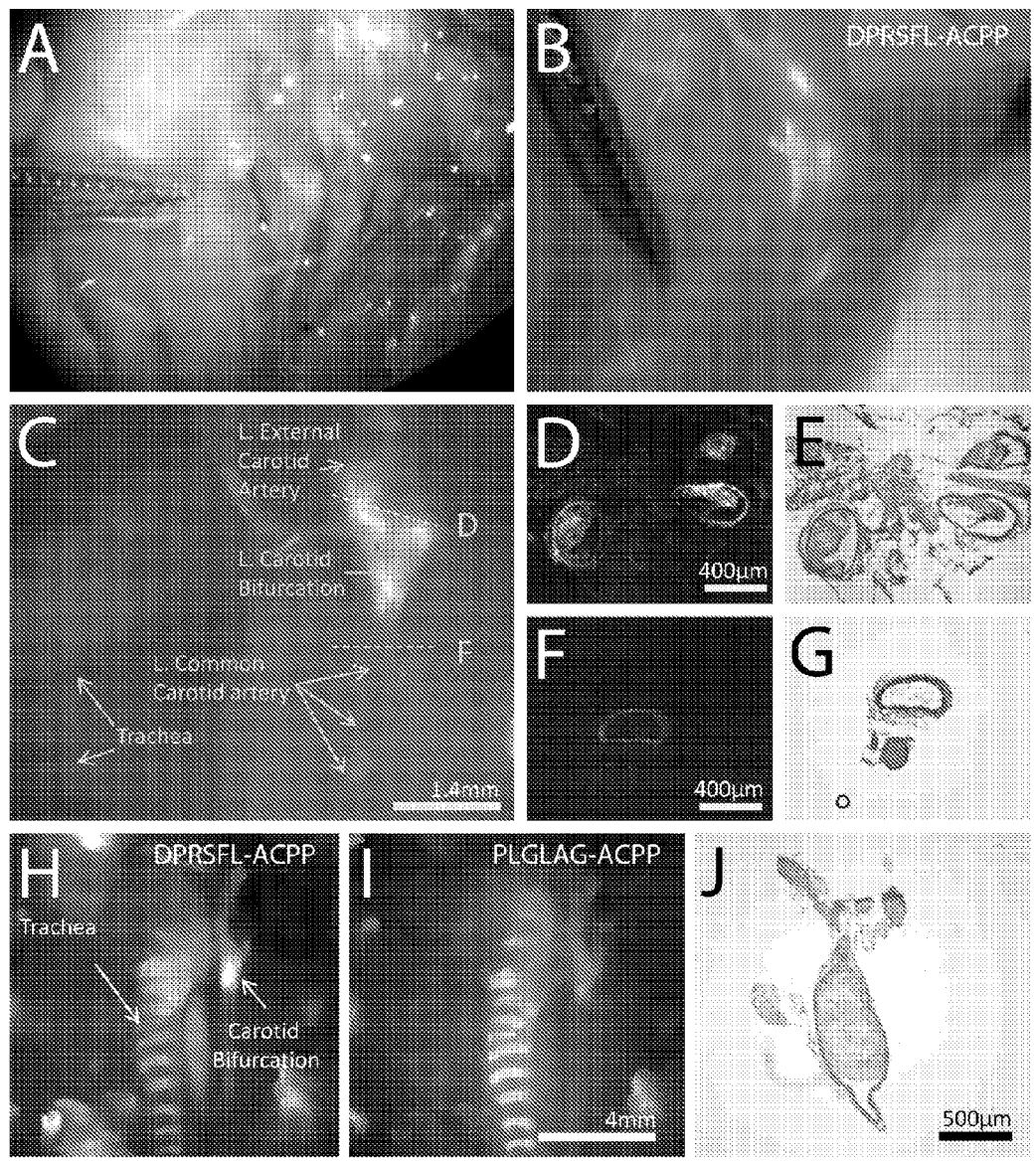
FIG. 6. DPRSFL (SEQ ID NO: 1)-based transport molecule is taken up in human carotid endarterectomy specimen. A-C: Fluorescence micrographs showing sections of atheromas incubated in DPRSFL (SEQ ID NO: 1)-based transport molecule (A), PLGLAG (SEQ ID NO: 4)-selective transport molecule (B) or mPEG-selective transport molecule (C). The DPRSFL (SEQ ID NO: 1)-based transport molecule sections show the most uptake. D: All of the atheromas tested were AHA Class 5 by H/E stain (D). E: Gel electrophoresis confirming cleavage of the DPRSFL (SEQ ID NO: 1)-based transport molecule and PLGLAG (SEQ ID NO: 4)-selective transport molecule but not the mPEG control selective transport molecule in carotid sections. F: Bar graph showing combined average intensities of seven representative sections from each of the treatment groups (A-D). Statistical significance was assessed by unpaired t-test as indicated.

The utility of DPRSFL (SEQ ID NO: 1) for visualizing potentially lethal vulnerable plaques during fluorescence guided vascular surgery was assessed by exposing plaque laden arteries in high risk areas such as the carotid and coronary circulation. Intraoperative (FIGS. 6A and B) and postmortem (FIG. 6C, 6H-I) exposure of the ascending carotid artery revealed plaques in the artery itself as well as at the carotid bifurcation. Fluorescence and H/E histology confirmed that plaque containing regions of the vessel were bright on fluorescence, whereas plaque-free regions were indistinguishable from background (FIG. 6D-G). We found that DPRSFL (SEQ ID NO: 1)-based transport molecule was more effective in labeling carotid plaques than PLGLAG (SEQ ID NO: 4)-selective transport molecule (FIG. 6H-J). In one of the oldest, sickest animals, coronary artery plaques were visible with the TRITC labeled DPRSFL (SEQ ID NO: 1)-based transport molecule. Plaques in both the right and left coronary artery were confirmed by H/E histology (FIG. S6).

Example 3: Thrombin Cleavable Selective Transport Molecules in Cancer, Stroke and Atherosclerosis Peptide Synthesis.

Peptides (Suc-e9-XDPRSFL-r9-c(cy5)-CONH2, Suc-e9-ODPRSFL-r9-c(cy5)-CONH2, Suc-e9-Xdprsfl-r9-c(cy5)-CONH2 and Suc-e9-(PEG-5)-r9-c(cy5)-CONH2 were synthesized and labeled with cy5 using a standard procedure, where X=aminohexanoic acid and O=PEG-2. Briefly, peptides were synthesized on an automatic peptide synthesizer following standard procedures for fluorenylmethoxycarbonyl solid-phase synthesis. Peptides were N-terminally capped with a succinate and C-termini were amidated. After cleavage off the resin, the C-termini were labeled through the cysteine with Cy5 monomaleimide. Peptides were purified using HPLC.

Cleavage Experiments.

Whole blood was collected either via cardiac puncture or from the abdominal aorta, either in heparinized tubes (plasma) or eppendorf tubes (serum). Both tubes were centrifuged at low speeds to pellet out the red blood cells, and the supernatant was removed and frozen for future use. Assays were done using between 2 and 5 µM peptide. Peptide gels were run and bands were quantified by integrated density using Image J.

Tumor Models

Tumor xenografts were made by inoculating the mammary fatpad with roughly one million cells approximately one week prior to the experiment. Tumors were allowed to reach no more than 2 cm in size and were typically in the range of 0.5-1 cm.

Imaging Experiments

Animals were anesthetized with a ketamine/midazolam cocktail (80 mg/kg, 40 mg/kg) and injected with the indicated probe (10 nmole/mouse). Animals may have been re-anesthetized at two hours post injection. Animals were sacrificed between four and six hours after injection. Organs were removed and lungs were inflated with 50% OCT/PBS and frozen for cryohistology. Lung and Tumor imaging.

Twenty micron slices were cut using a cryotome. Images were taken using a fluorescence dissecting microscope (Zeiss Lumar, ex 620/60, em 700/75) and processed using Adobe Photoshop.

Clot Aging Experiments.

Blood was obtained via cardiac puncture and allowed to clot in an Eppendorf tube. Small clots were cut off for processing at each time point. At the indicated time point, clots were incubated in either 3 and 6 µM Suc-e8-ODPRSFL-c(cy5)-CONH2 or Suc-e8-mPEG-c(cy5)-CONH2 for 10 minutes. At least two clots were assayed for each time point for each mouse. After staining, clots were washed three times in 2 mL PBS shaking, then were imaged at 700 nm using a fluorescence mouse imager (CRI, Maestro, ex 640/48, em 700 nm). Data were quantified by integration with Image J.

Stroke Experiments.

Male Sprague-Dawley rats (Harlan, San Diego, Calif., USA), 260 to 320 g, underwent surgery to transiently occlude the left middle cerebral artery (tMCAo) with intraluminal 4-0 nylon suture All sutures were pre-blunted in a microforge (Narishige MF83, NY, USA) and only filaments between 280 and 305 µM in diameter were used for occlusion. The surgical exposure and occlusion conditions were performed as previously described. Animals were prepared with 2 h of tMCAO; rats in the 4 hour reperfusion group also received intravenous injections of 2 Mda fluorescein dextran prior to surgery. The rats were re-anesthetized for de-occlusion with isofluorane; immediately following de-occlusion, the tail vein was injected with cy5 labeled thrombin probe, cy5 labeled mpeg control probe, or cy5 labeled PEG-5 control probe followed by rhodamine labeled thrombin cleavable probe. Reperfusion duration was varied from 4 hours, 24 hours, to 48 hours. Rats were then administered an overdose of pentobarbital and perfused transcardially with normal saline followed by buffered paraformaldehyde and the brain was removed from the skull. Imaging was done with the Maestro mouse imager (ex 640/48, em 700 or 730 nm)

Microstroke Experiments.

Briefly, rats were induced with 4% (v/v) isoflurane and maintained with 1 to 2% (v/v) isoflurane in 30% $O_2$ and 70% $N_2O$ delivered through a custom nose cone. Atropine, 0.05 mg per kg rat, delivered by intraperitoneal injection, and lidocaine, 2% (v/v), delivered by subcutaneous injection at the site of incision, were administered at the start of surgery. Body temperature was maintained at 37° C. with a feedback regulated rectal probe and heat pad (50-7053-F; Harvard). Heart rate and blood oxygen saturation were continuously monitored using a pulse oximeter (8600V; Nonin). To form the cranial window, the rat was placed in a stereotaxic frame and the skull was exposed by a mid-line incision to the scalp. The left temporal muscle was retracted from the skull and the skull surface was cleaned, dried, and the position of a 4×4 mm cranial window, centered at 4.5 mm lateral and −3 mm caudal, was marked. Two small anchoring screws (#000 self-tapping; Small Parts) were placed rostral and caudal to the window and were glued in place with a drop of Vetbond™. A metal plate for securing the rat to the imaging apparatus was fixed to the skull and screws using dental cement. The cranial window was generated by first thinning away half of the skull thickness using dental air-drill bit. The perimeter of the window was further thinned until it formed a flexure that revealed the underlying dura. The bone flap was separated along the flexure using sharp forceps and gently lifted parallel to the skull surface. The dura was flushed with ACSF and moist Surgifoam was applied to control any dural vessel bleeding. The dura was then nicked with a 26 gauge needle point and teased apart with two sharp forceps without tearing of any large dural vessels. Low melting-point agarose (#A4018; Sigma), dissolved at a concentration of 1.5% (w/v) in ACSF containing neither carbonate nor phosphate, was cooled to body temperature and applied directly to the exposed cortex. The window was then sealed with a glass cover slip and a thin frame was then screwed atop the metal plate to sandwich the cover glass in place. Probe was injected using a tail vein catheter while the animal was still under anesthesia.

Two photon images were collected using a two-photon laser scanning microscope of local design that was controlled by MPScope software. To make the vasculature fluorescent, a 0.3 mL bolus of 5% (w/v) 2 MDa fluoroscein-dextran (Sigma) in saline was administered through the femoral artery catheter. A 0.3-numerical aperture (NA), 10-times magnification water-dipping objective (Zeiss) was used to collect a large-scale map to aid navigation through the cortical vasculature. We then switched to a 0.8-NA, 40-times magnification water-dipping objective (Olympus) to obtain high-resolution line-scan and planar image data. The line-scans were collected along the centerline of each vessel over a length of 70 pixels spanning 7 to 76 µm, at a scan rate of 1.6 kHz/line, to establish the speed of RBCs. Planar image stacks, 256 by 256 pixels, were acquired to establish the diameter the vessel. Clots were generated by injecting rose bengal into the circulation and then locally photoactivating it for 1-3 minutes using 532 nm laser light. Several clots were made over the course of 30 minutes prior to injection of probe. Three hours after probe injection, animals were sacrificed, perfused transcardially with FITC-agarose and the brain removed from the skull. The cortex was flattened and imaged using standard fluorescence microscopy (Zeiss).

Atherosclerosis Experiments.

Atherosclerotic animals had a homozygous deletion for ApoE and were fed a high fat diet for six to 12 months prior to the experiment. Animals were injected through the tail vein with probe (10 nmole/mouse). Six hours later, animals were sacrificed, perfused with saline and aortas harvested. Kidney signal was used to verify that the negative control animals received adequate probe.

A Thrombin-Cleavable Peptide was Made by Replacing the XPLGLAG (SEQ ID NO: 18) Linker by (X/O)DPRSFL (SEQ ID NO: 19).

Figure 7:
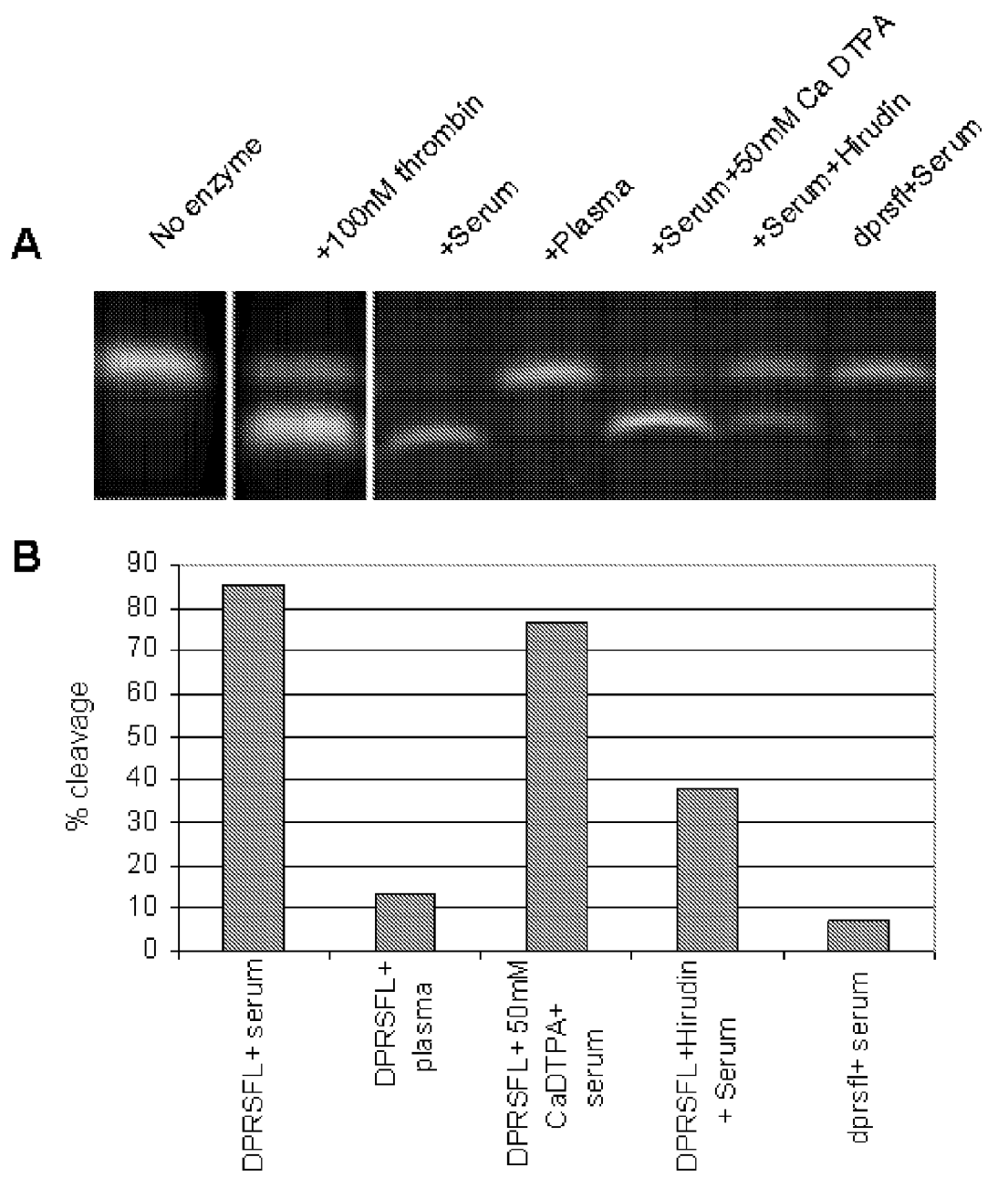
FIG. 7. DPRSFL (SEQ ID NO: 1) peptide is selectively cleaved by thrombin as well as by purified blood. (A) shows approximately 2.5 µM cleavable peptide (Suc-e8-XD-PRSFL-r9-c(cy5)) incubated for 20 minutes at room temperature under the indicated conditions. (B) shows the percent cleavage for the gel shown in (A). Similar results were seen for a Suc-e8-ODPRSFL-r9-c(cy5) analogue.

The peptide was labeled with cy5 for detection, purified by HPLC and tested for purity by gel electrophoresis. The peptide was cleaved by purified thrombin (Calbiochem), with a $k_{cat}/k_m$ on the order of $5*10^5$, and by purified plasmin (Calbiochem) with a $k_{cat}/k_m$ on the order of $1\times10^5$. It was cleaved by serum, but not by heparinized plasma (FIG. 7). Quantitatively, cleavage was detectable by gel when peptide was incubated by as little as 2.5 nM thrombin. The cleavage by clotted blood was partially inhibited when the assay was done in the presence of 200 U/mL hirudin, a natural inhibitor of thrombin derived from leech saliva. We were not surprised by the incomplete inhibition, since incomplete inhibition by direct thrombin inhibitors has been reported previously in the literature for clot-bound thrombin. Another possible explanation is activation of Factor Xa, a second enzyme involved in the clotting cascade that is capable of cleaving our probes in vitro (Jessica Crisp, unpublished observation). The one drawback with the XDPRSFL (SEQ ID NO: 20) peptide was that it was not very soluble (up to 200 µm in water). Solubility was partially addressed by changing the linker between the e9 and the r9 from amino-hexanoic acid (X) to PEG-2 (O). This resulted in little change to the cleavage characteristics of the molecule; cleavage by serum was still inhibited by the presence of heparin and by the addition of 200 U/mL hirudin, but did cause a qualitative improvement in solubility that was necessary for injection into animals.

Fluorescent Thrombin Cleavable Probes Accumulate in Tumors in Xenografted Animals.

Figure 8:
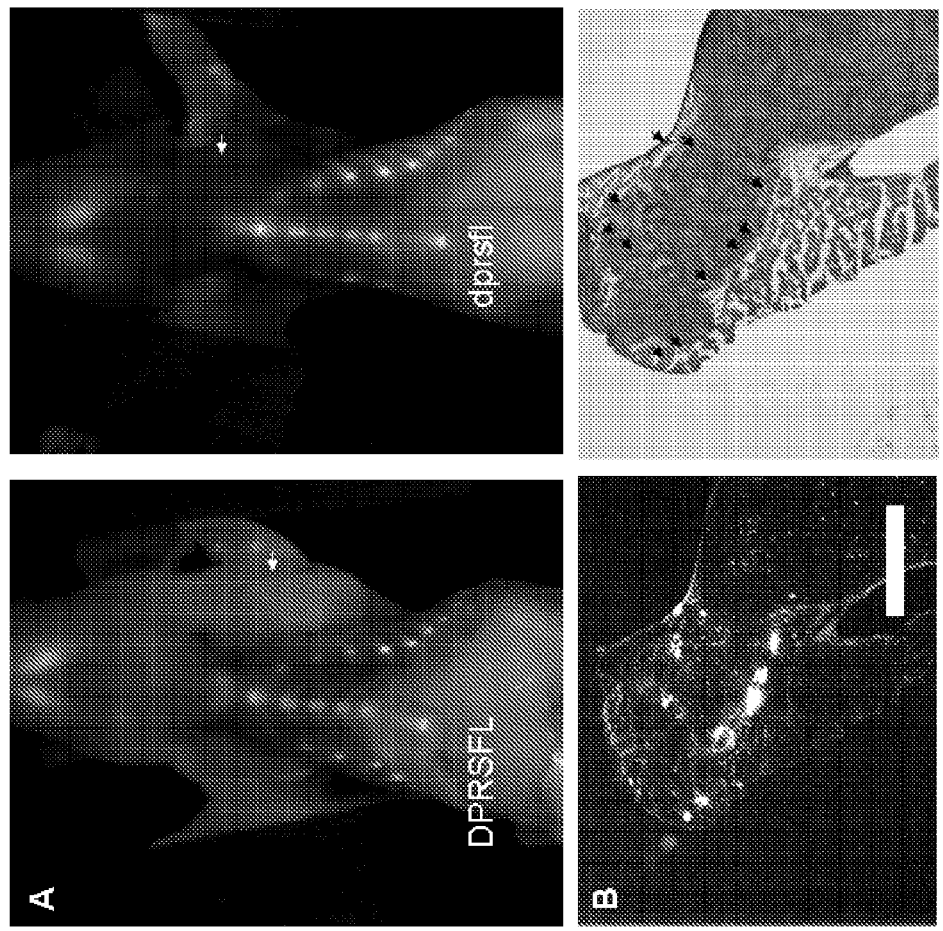
FIG. 8. Thrombin cleavable peptides are selectively taken up by specific cells in HT-1080 xenografts. (A) shows exposed tumors six hours post injection with 10 nmol Suc-e8-XDPRSFL-r9-c(cy5). The all-d-amino acid analogue is not cleavable by thrombin and therefore is not expected to be taken up by tumors. (B) shows a cryosection of an HT-1080 tumor six hours after injection with a Suc-e8-ODPRSFL-r9-c(cy5) peptide. The identity of the bright spots is unclear. Scale bar=1 mm.
Figure 9:
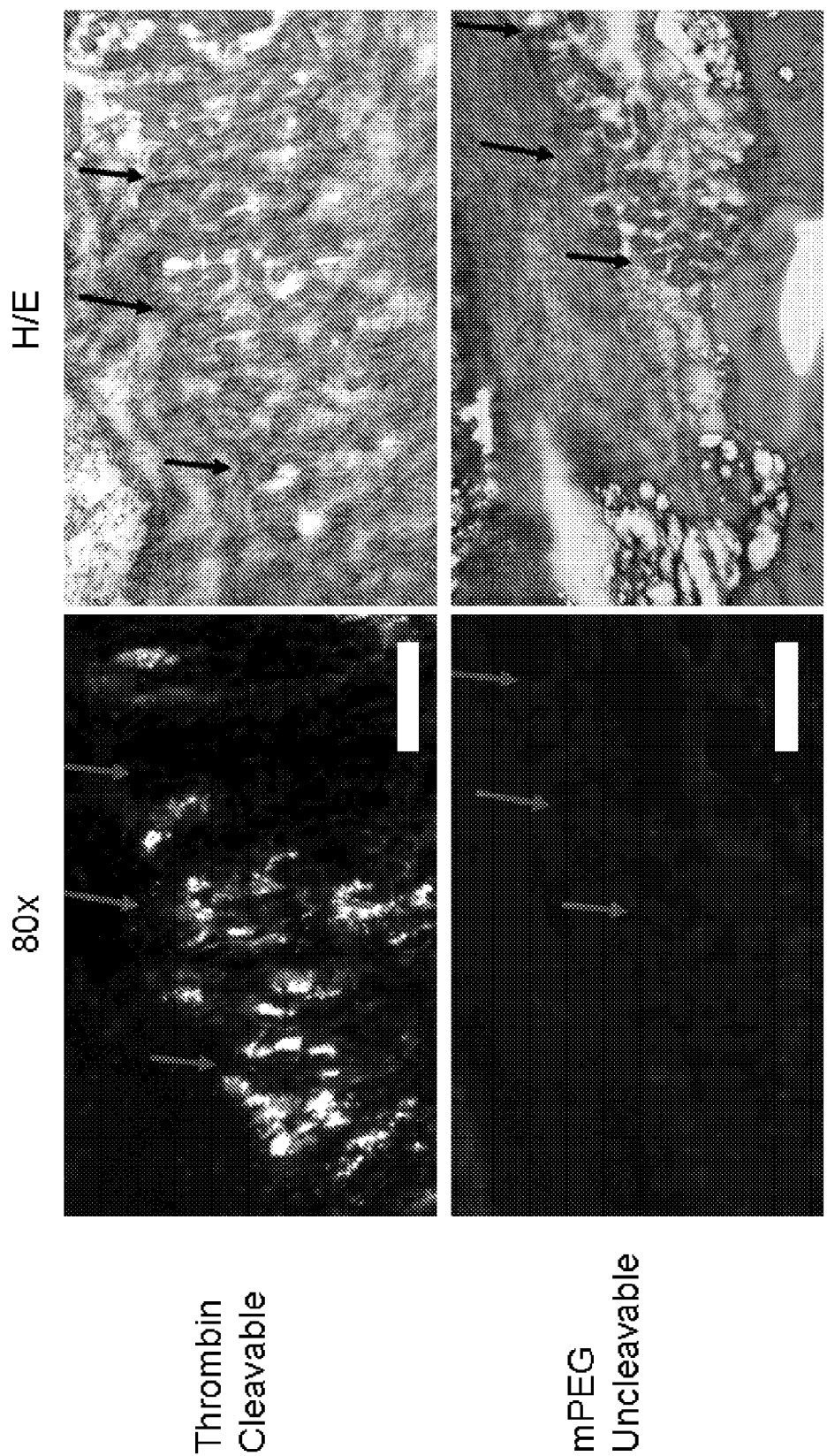
FIG. 9. Thrombin cleavable peptides are selectively taken up by specific cells in B16-F10 melanoma syngeneic xenografts. (A) shows a representative section of tumor invading muscle from an animal injected with thrombin cleavable peptide. (B) shows standard hematoxylin/eosin staining of the same slice. (C) and (D) show a similar region from an animal injected with an uncleavable control peptide. Scale bars are 200 µm.

Thrombin and its PAR-1 receptor have been reported to be critical for the metastatic process in both melanoma and prostate tumor models. To test whether the thrombin probe could be used to monitor thrombin activity in vivo, we turned to two of the tumor models used before, HT-1080 xenografts in nude mice (FIG. 8) and B16-F10 grafts into syngenic immunocompetent B16 albino hosts (FIG. 9). When injected through the tail vein with either cleavable or uncleavable thrombin, tumors were readily visible in both models. Skin background was significantly less than for the MMP-based probe, and though synovial uptake remained, there was little uptake in cartilage in either model. The plasma halflife of the peptide was roughly 15 minutes, and excretion was very clearly via the hepatobiliary system with intestines and liver becoming very bright by two hours. In both models, uptake measured as per SUV was increased over the PEG-5 control, though overall uptake varied greatly and in neither case was the average difference between test and control significant (Table 6.1). This was explained nicely by frozen section histology, in which single cells stained extremely brightly, up to 100-fold over neighboring tissue, both tumor and normal. Though their role is unclear, these cells were uniformly located in areas where tumor was invading muscle. No such staining was seen when animals were injected with probes containing the MMP-cleavable linker or the uncleavable PEG-5 control linker, suggesting that uptake is thrombin dependent, although the cause for high uptake in selected cells remains unclear.

Thrombin Cleavable Probes Accumulate in Tumors, Metastases and Clots in Lungs Resulting from Spontaneous Tumors Arising in Transgenic Animals Expressing the PyMT Oncogene Driven by the MMTV Promoter When the thrombin cleavable selective transport molecules were injected into tumor bearing PyMT mice, gross tumor fluorescence was not significantly different for the cleavable probes relative to the PEG-5 control probe. On histology, a dim stromal distribution was punctuated by bright intratumoral clots and cysts. Additionally, select muscle cells appeared to stain if they were infiltrated by or came in direct contact with tumor. This was not the case if the muscle was separated from tumor by a fibrous capsule, indicating that thrombin is likely important in the invasion process but not in the process of tumor establishment or encapsulation. As expected from previous results, necrotic areas were highlighted with all selective transport molecule-based probes.

Figure 10:
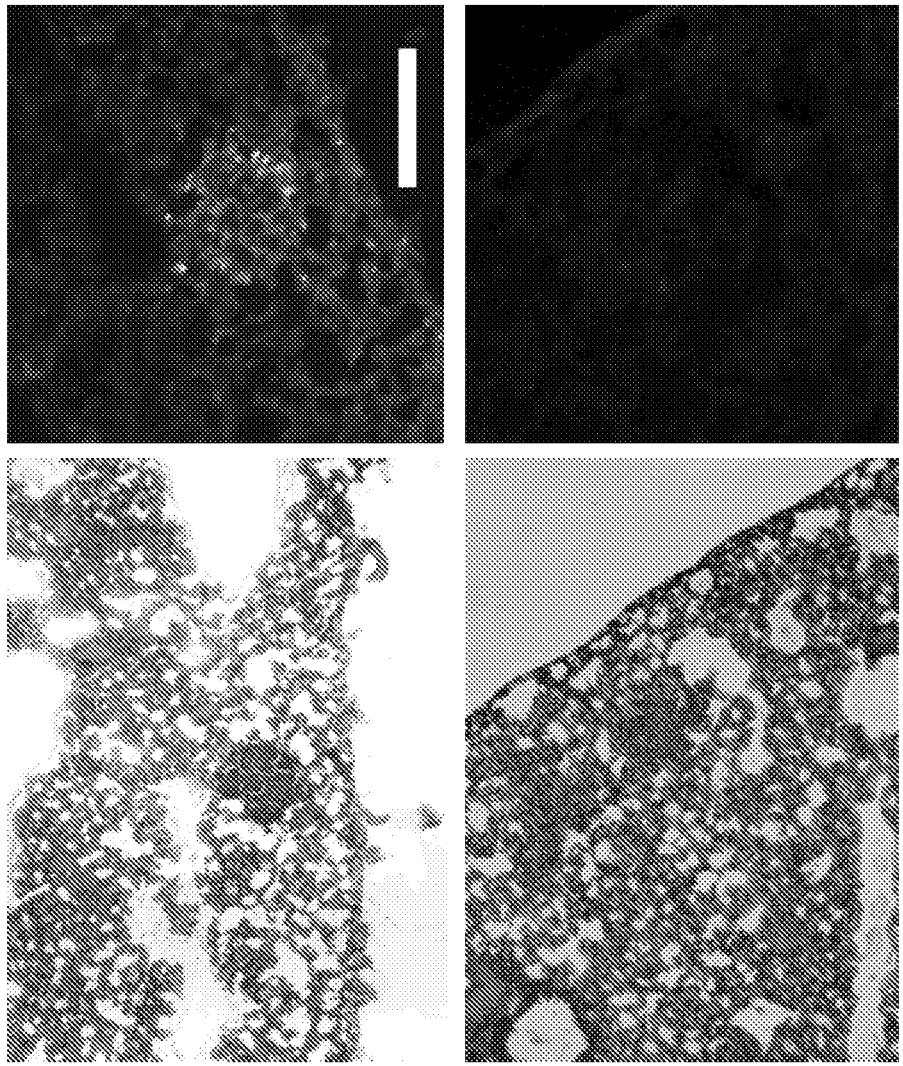
FIG. 10. Uptake of thrombin cleavable peptide into lung metastases from PyMT animals. Animals were injected with either the cleavable (A) or uncleavable (B) peptides and sacrificed six hours later. Hematoxylin/eosin stained adjacent slices (left) were used to find metastases on frozen sections. Scale bar=200 µm.
Figure 11:
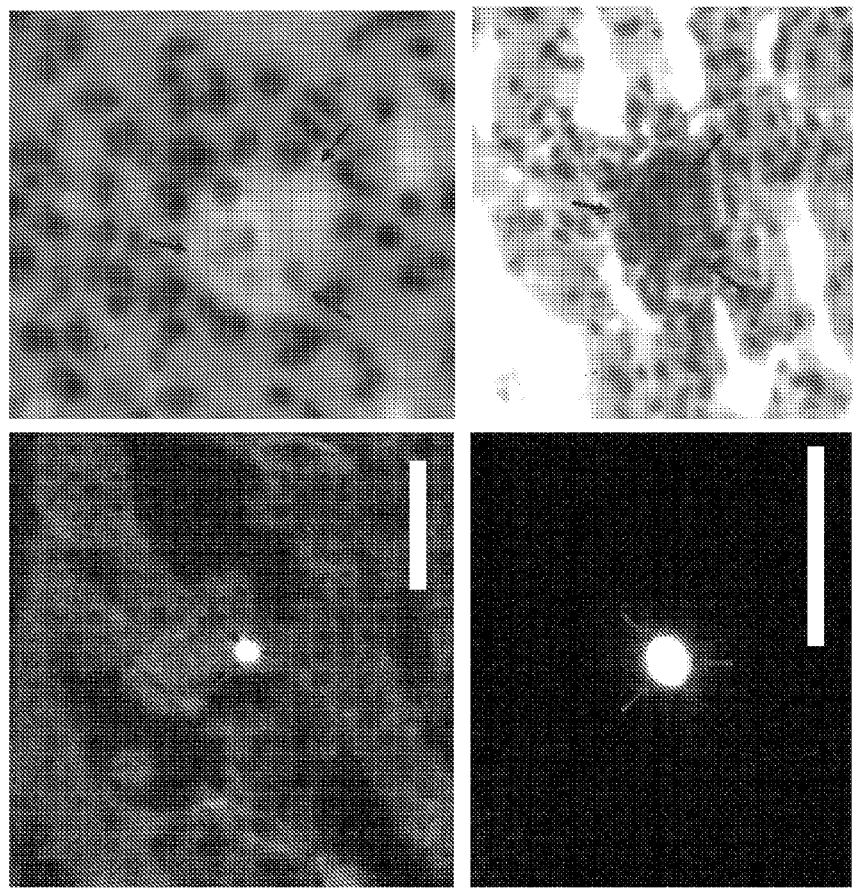
FIG. 11. Very bright spots in lungs correspond to lymphocytes and macrophages possibly surrounding tumor cells. Scale bars=100 µm.
Figure 12:
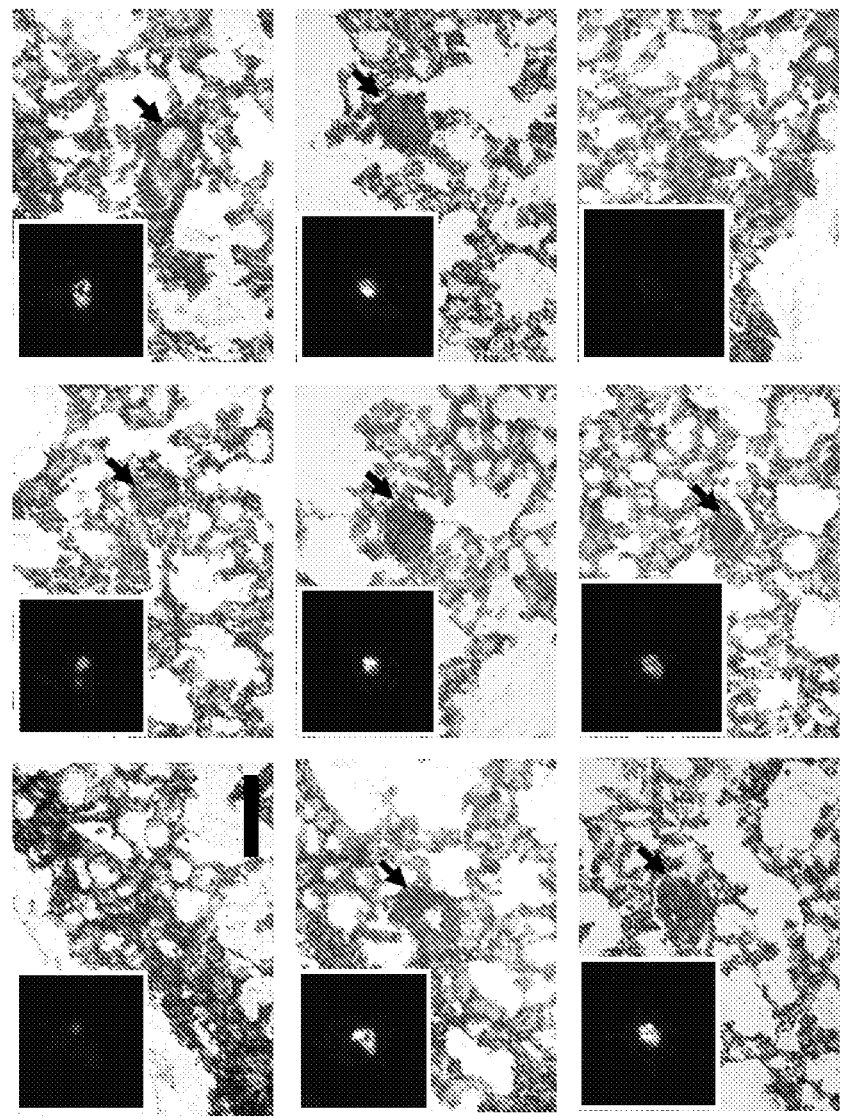
FIG. 12. Uptake of Thrombin Cleavable Peptide into blood clots in vivo. This 180 mm long clot of unknown etiology was found in a lung from a PyMT mouse. In addition to lungs, brightly staining clots were found inside vessels in tumors. Scale bar=200 µm.

Spontaneous metastases in lung were highlighted by the cleavable probe (n=1), but were nearly invisible for the uncleavable probe (n=1), indicating that the coagulation cascade may be activated by the process of metastasis (FIG. 10). In addition to overt metastases, lungs from animals having received the cleavable, but not the uncleavable, peptide contained very bright clusters of immune cells. The cause for the clusters was not clear, but it is possible that they are due to platelets and activated immune cells surrounding tumors (FIG. 11). The third and most obvious observation made in polyoma lungs was the presence of very bright clots (FIG. 12). These presented with up to 10:1 contrast on gross dissection, and up to 80:1 on histology. The clots were of unknown etiology, but are probably due to a hypercoaguable state resulting from high tumor burden and possible metastasis.

Ex-Vivo Clot Aging Studies.

Figure 13:
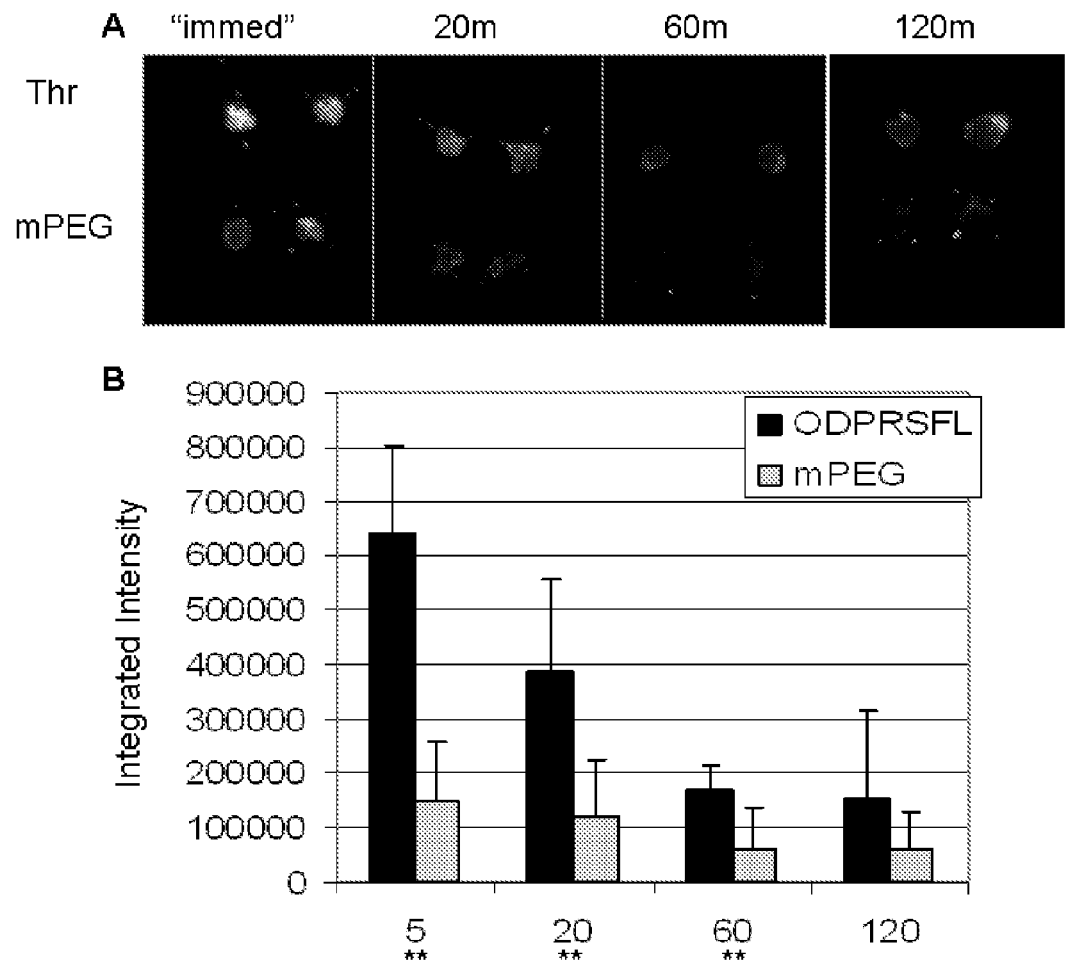
FIG. 13. Thrombin peptide stains fresh clots, but not aged clots, in an in vitro clotting assay. (A) shows gross images of fresh clots incubated for ten minutes with either 3 or six µM of either Suc-e8-ODPRSFL-r9-c(cy5) or an all d-amino acid control probe with a mPEG linker, then washed three times for ten minutes. (B) quantitates the results shown in (A) for three mice, two clots each.

According to the thrombin burst hypothesis, thrombin activity could theoretically be used to determine the age of a clot. To test whether this could work ex vivo, blood was collected from wildtype mice by cardiac puncture. Clots were allowed to form, and once they had grown large enough to be maneuverable were stained for 15 minutes in 5 µM thrombin cleavable XDPRSFL (SEQ ID NO: 20) peptide, washed five times and imaged. The uncleavable PEG-5 control was used as a standard. As expected, the ratio of fluorescence from clots incubated in cleavable peptide to those incubated in uncleavable peptide started off high, then decreased steadily over two hours (FIG. 13). The experiment was repeated more carefully with blood from three mice with the new ODPRSFL (SEQ ID NO: 21) peptide, yielding similar, but this time statistically significant differences between clots incubated in ODPRSFL (SEQ ID NO: 21) peptide and clots incubated in PEG-5 peptide at the 5 m, 20 m and 1 h time points. By the two hour time point, there was no significant difference in uptake between the two peptides. Two clots were done per time point and the results averaged. The incubation solutions were run on gels after the completion of the experiment, showing incomplete cleavage of the ODPRSFL (SEQ ID NO: 21) peptide and no cleavage of the PEG-5 control peptide.

Imaging Stroke with Thrombin Cleavable Selective Transport Molecules

Figure 14:
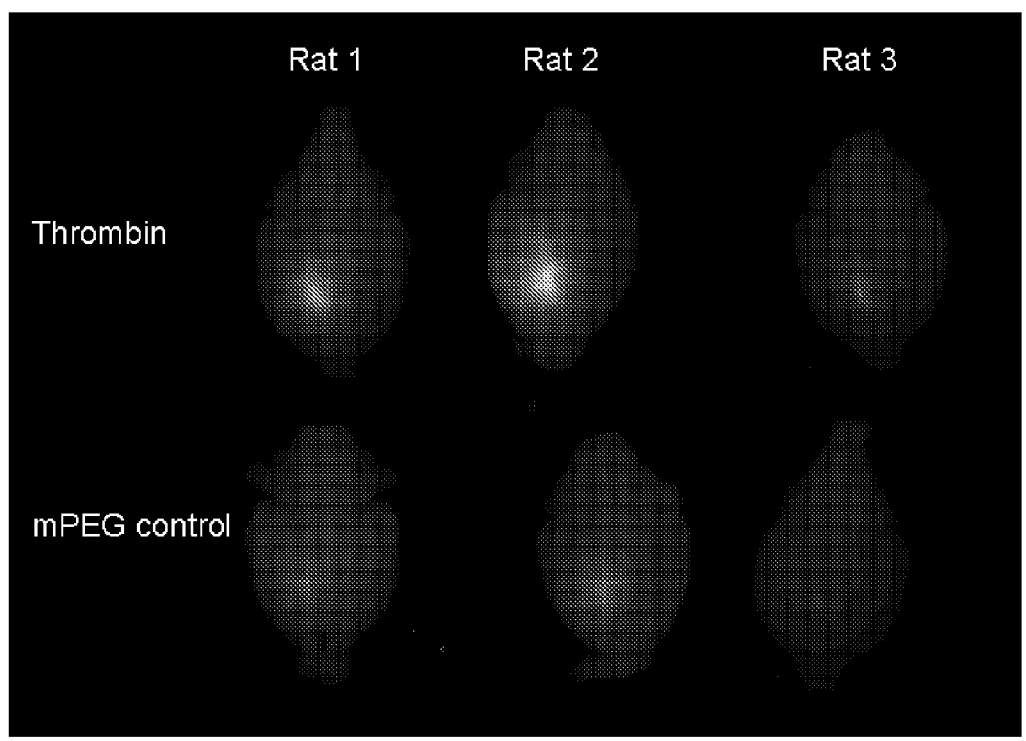
FIG. 14. Uptake of thrombin probe is selective, but varies depending on the size of the stroke.
Figure 15:
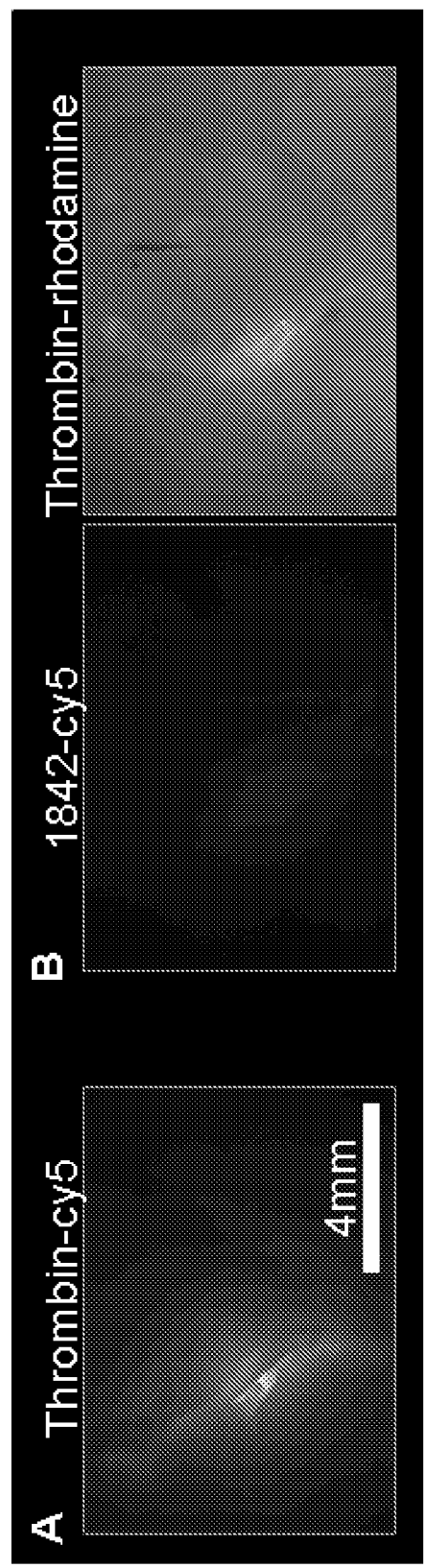
FIG. 15. Dual color imaging verified the presence of a stroke in animals injected with the PEG-5 control peptide. (A) shows an animal that received thrombin cleavable peptide labeled with cy5. (B) shows a different animal that was co-injected with cy5-labeled PEG-5 control peptide and rhodamine labeled thrombin cleavable peptide.
Figure 16:
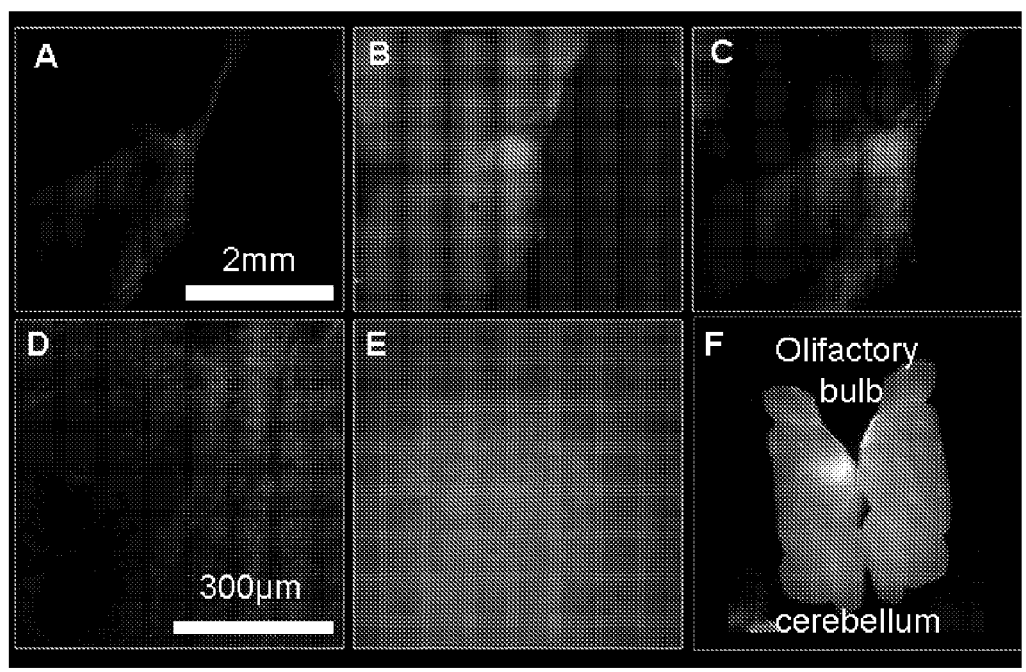
FIG. 16. Thrombin (Suc-e8-OPLGLAG-r9-c(cy5)) and plasmin (Suc-e8-XRLQLKL-r9-k(FITC)) cleavable selective transport molecules are taken up selectively in an animal model for cerebral ischemia. An animal was co-injected with thrombin (A) and (D) and plasmin (B) and (E) cleavable peptide immediately following reperfusion of the carotid artery. The two probes varied in distribution and did not colocalize (C). (F) shows a gross cy5 image of the same brain, cut sagittally and reflected outward.

To determine whether thrombin activity could label fresh strokes in vivo, we tested our probes in an occlusion/reperfusion model in which ischemic stroke is simulated by temporarily restricting blood flow to the middle cerebral artery by inserting a microfilament into the internal carotid artery. Although the blood brain barrier would ordinarily prevent peptide agents from entering brain parenchyma, ischemia is known to cause blood brain barrier breakdown in the viscinity of the lesion. Upon reperfusion, three animals were given 50nmol thrombin-cleavable peptide and three were given the PEG-5 control peptide. Animals were sacrificed and perfused 24 hours post occlusion (FIG. 14). Two of the animals given the PEG-5 negative control peptide were also given a rhodamine labeled thrombin cleavable peptide later in a different color to verify the presence of a clot (FIG. 15). Co-injection of a cy5 labeled thrombin cleavable peptide and a FITC labeled plasmin cleavable peptide gave differential uptake, particularly in brain parenchyma spatially removed from the damaged vessel (FIG. 16).

Figure 17:
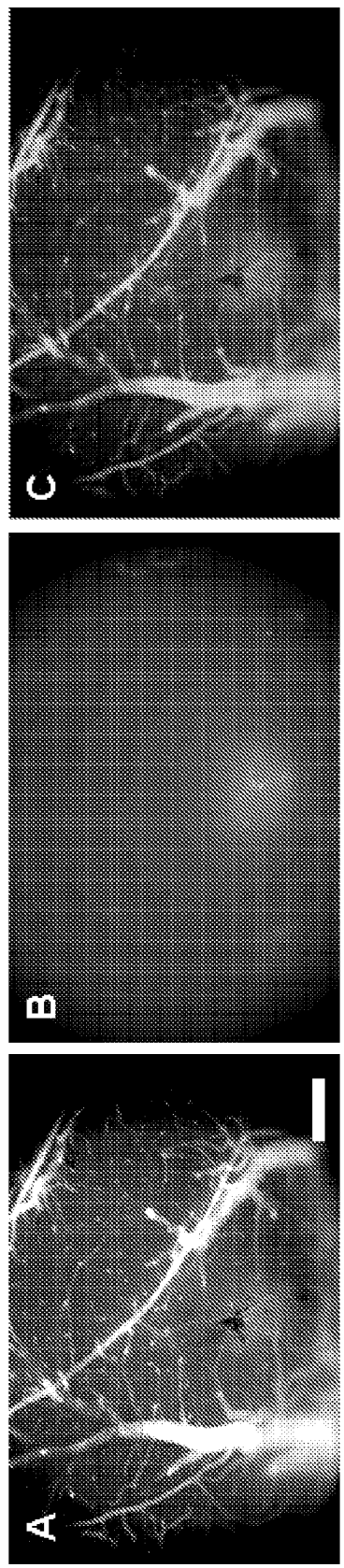
FIG. 17. Thrombin cleavable selective transport molecules label small, 500 µm clots caused by photooxidative damage. (A) shows vasculature labeled by FITC dextran. The clot caused by photoactivation of Rose Bengal is shown by an arrow. (B) shows a cy5 image of the same field. (C) shows an overlay of (A) and (B). Scale bar=500 µm.

In a second preliminary experiment, penetrating arterioles were individually clotted by targeted photodynamic damage induced through the excitation of injected Rose Bengal by a green laser. Excitation of Rose Bengal releases singlet oxygen that damages the vessel wall, forming a clot. These clots can either be transient if they are small, or more permanent if they are larger. Using this strategy, we were able to visualize clotting of a single arteriole using the thrombin probe with approximately 2.5 to one contrast in flattened cortex. This strategy for induction of clots is less traumatic to the animal, and causes less leakage of the vessels as detected by the FITC-dextran (FIG. 17). In principle, these experiments can also be done in vivo using the two-photon microscope. Although preliminary, these results suggest that the thrombin peptide may be useful for looking at acute thrombin activity following ischemic stroke in various models.

Thrombin Activity in Atherosclerosis

A third area where thrombin activity has been correlated to chronic disease is in the formation of atherosclerotic plaques. Although most current imaging research on proteases in atherosclerosis focuses on the involvement of MMP's and cathepsins PAR's are known to be overexpressed by several cell types in atherosclerosis. Since it was unclear whether thrombin or MMP would be superior at visualizing plaques, we decided to try both. We collaborated with the Tsimikas lab at UCSD to obtain ApoE$^{-/-}$ animals that had been fed a high fat diet and had significant (30-90%) atherosclerotic burden. Since limited animals were available, both male and female end-stage animals were used for this preliminary set of experiments in which two animals each were injected with MMP, thrombin and the uncleavable mPEG control probe. Animals were quite ill, frequently showing evidence of co-morbidities such as arthritis, blindness and rectal prolapse. Animals were injected with 10 nmol probe and were sacrificed and perfused with saline six hours later. Following perfusion, aortas were dissected out and pinned down for gross fluorescence analysis.

Figure 18:
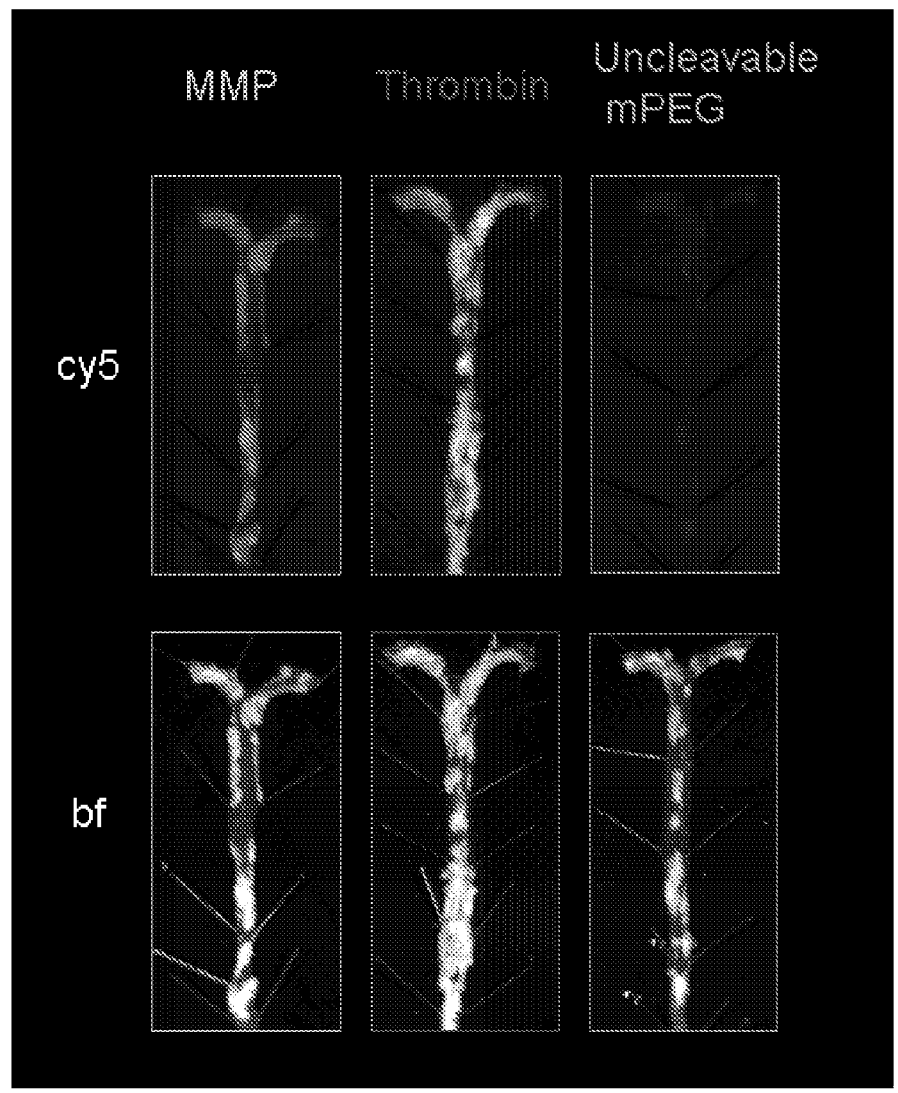
FIG. 18. Uptake of thrombin-cleavable, MMP-cleavable and PEG-5 uncleavable selective transport molecules in atherosclerotic plaques in one year old female ApoE−/− mice.
Figure 19:
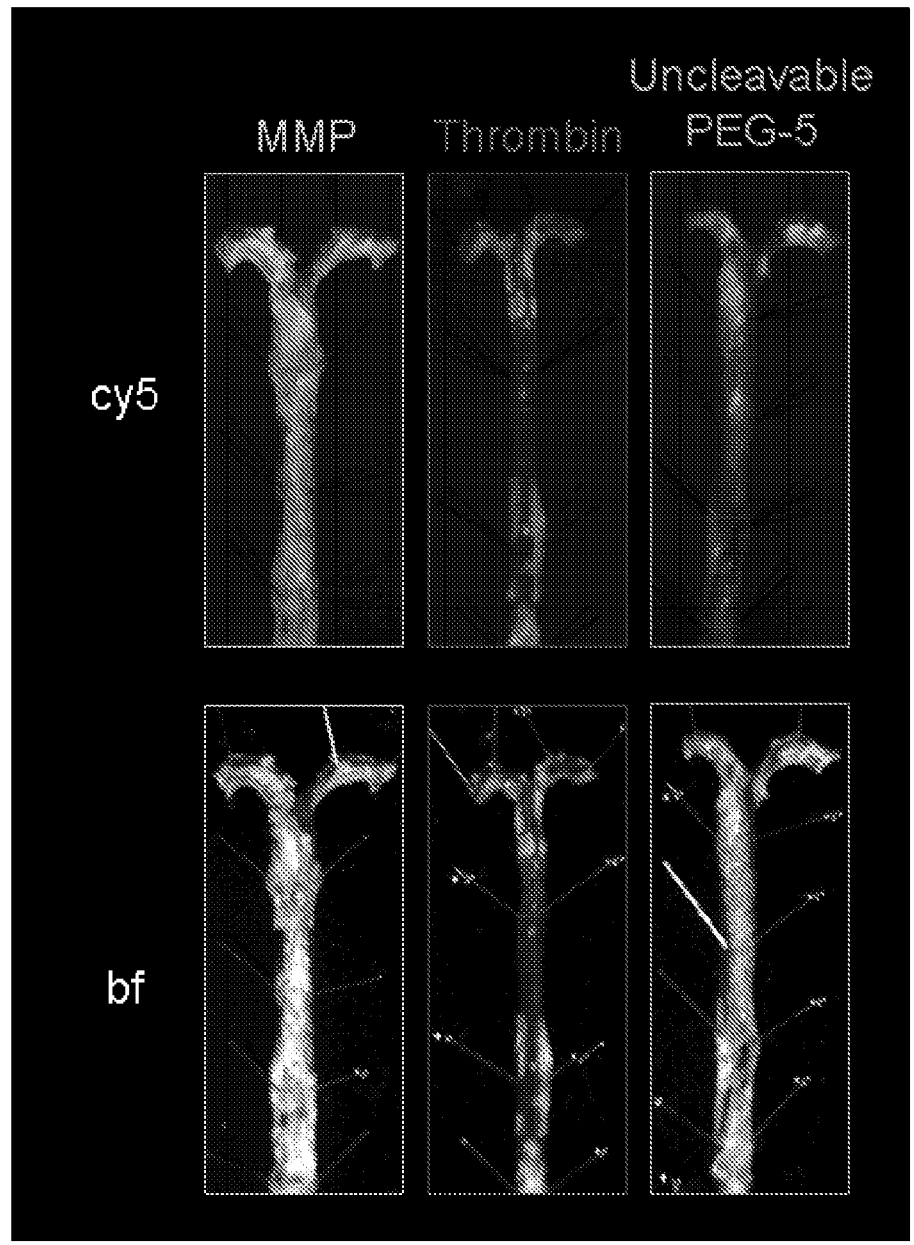
FIG. 19. Uptake of thrombin-cleavable, MMP-cleavable and PEG-5 uncleavable selective transport molecules in atherosclerotic plaques in two year old male mice ApoE−/− mice. There is highlighted necrosis present in the arch of the animal injected with the uncleavable control probe.

On gross analysis, there was a statistically significant 2.7-fold difference between plaque uptake in the animals injected with the thrombin cleavable selective transport molecule and control animals injected with the uncleavable control probe (1093±437, n=4 vs. 393±179, n=4, p<0.05). Intensities were derived by masking regions of plaque in Amira software and are given in arbitrary units. In non plaque regions, uptake was comparable, 321±108, n=4 vs. 208±124, n=4. When the groups were separated into male mice and female mice, it became clear that plaques from the one year old female mice injected with thrombin probe took up twice as much probe as similar plaques from the two two-year-old male mice (1440±275, n=2 vs. 746±139, n=2, FIG. 18, FIG. 19). The opposite trend held true for the four animals injected with the PEG-5 negative control peptide (249±179, n=2 vs. 537±275, n=2), likely due to the presence of necrosis in vulnerable plaques in the aortic arch region. Animals injected with the MMP cleavable selective transport molecule showed no obvious difference in uptake between the two sets of animals, though the aggregate difference between test and control was significant (1072±188, n=4 vs. 393±179, n=4, p<0.05).

Figure 20:
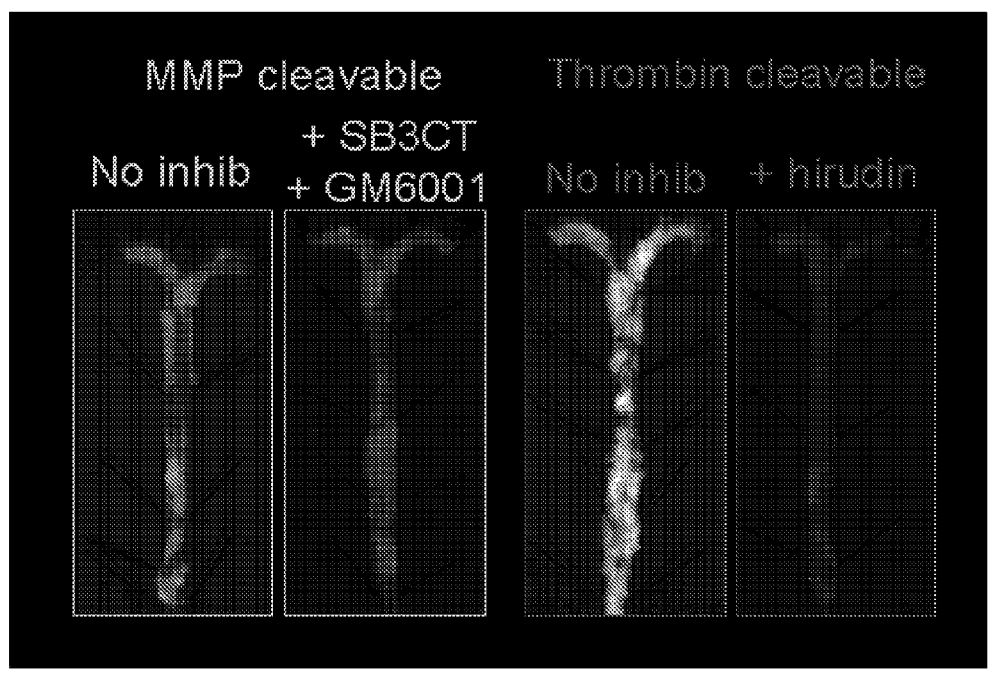
FIG. 20. Inhibition of thrombin-cleavable selective transport molecule uptake in atherosclerotic plaques by hirudin and MMP-cleavable selective transport molecule uptake by an MMP inhibitor cocktail.

To verify that the differences in intensities were due to thrombin and MMP cleavage respectively, we used hirudin and an MMP inhibitor cocktail (GM6001 and SB3CT) to inhibit thrombin and MMP activity respectively. Pre-injection with hirudin[159] 30 minutes prior to injection with thrombin cleavable peptide decreased uptake by 75% (1440±275, n=2 vs. 354±179, n=2, p=0.06), whereas a cocktail of MMP inhibitors was only able to decrease uptake by 50%, FIG. 20. SB3CT delivered alone showed no effect on uptake (data no shown). Together, this data shows that uptake is mostly due to protease specific cleavage of the appropriate linker by atherosclerotic plaques.

Visualizing Thrombin Activity in Plaques with TI MRI.

Figure 21:
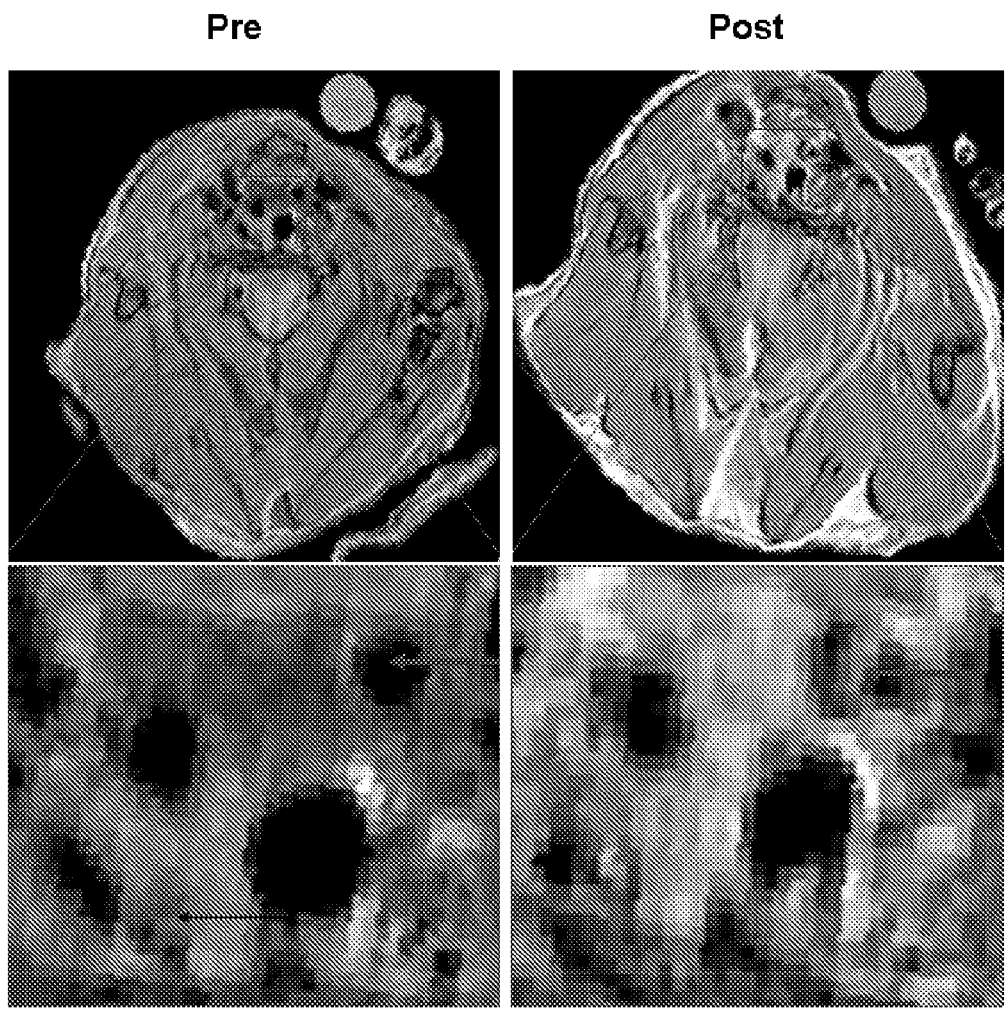
FIG. 21. Thrombin cleavable peptides can highlight regions of atherosclerosis on MRI. This Figure shows a TI weighted MSME image of the internal carotid artery pre and post contrast. The arrow marks a region of atherosclerotic plaques.
Figure 22:
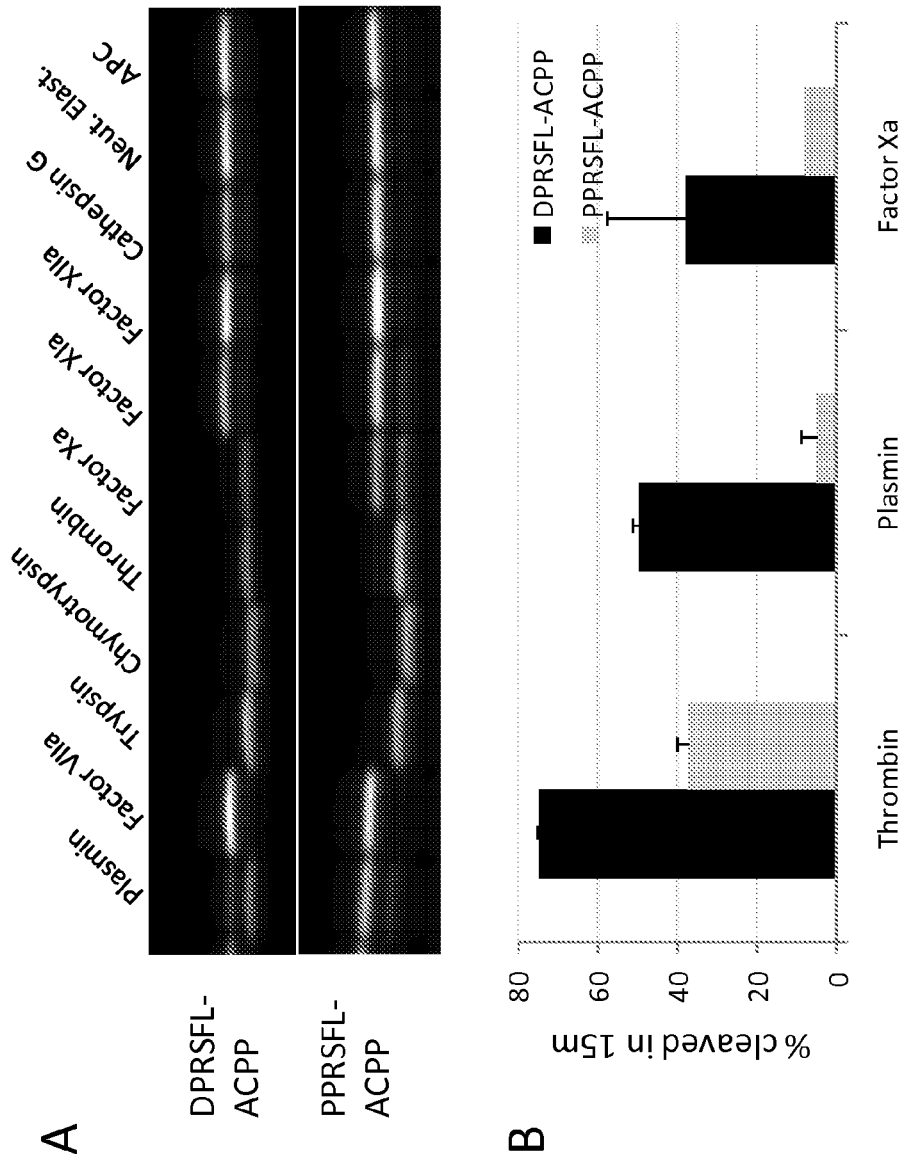
FIG. 22. A: DPRSFL (SEQ ID NO: 1)-selective transport molecules and PPRSFL(SEQ ID NO: 2)-selective transport molecule cleavage after one hour incubation in a panel of commercially available enzymes showing near complete cleavage by trypsin, chymotrypsin, thrombin, plasmin and Factor Xa. B: Quantitative comparison of thrombin, plasmin and factor Xa cleavage of DPRSFL (SEQ ID NO: 1)- and PPRSFL (SEQ ID NO: 2)-selective transport molecules after 15 minutes of incubation.
Figure 23:
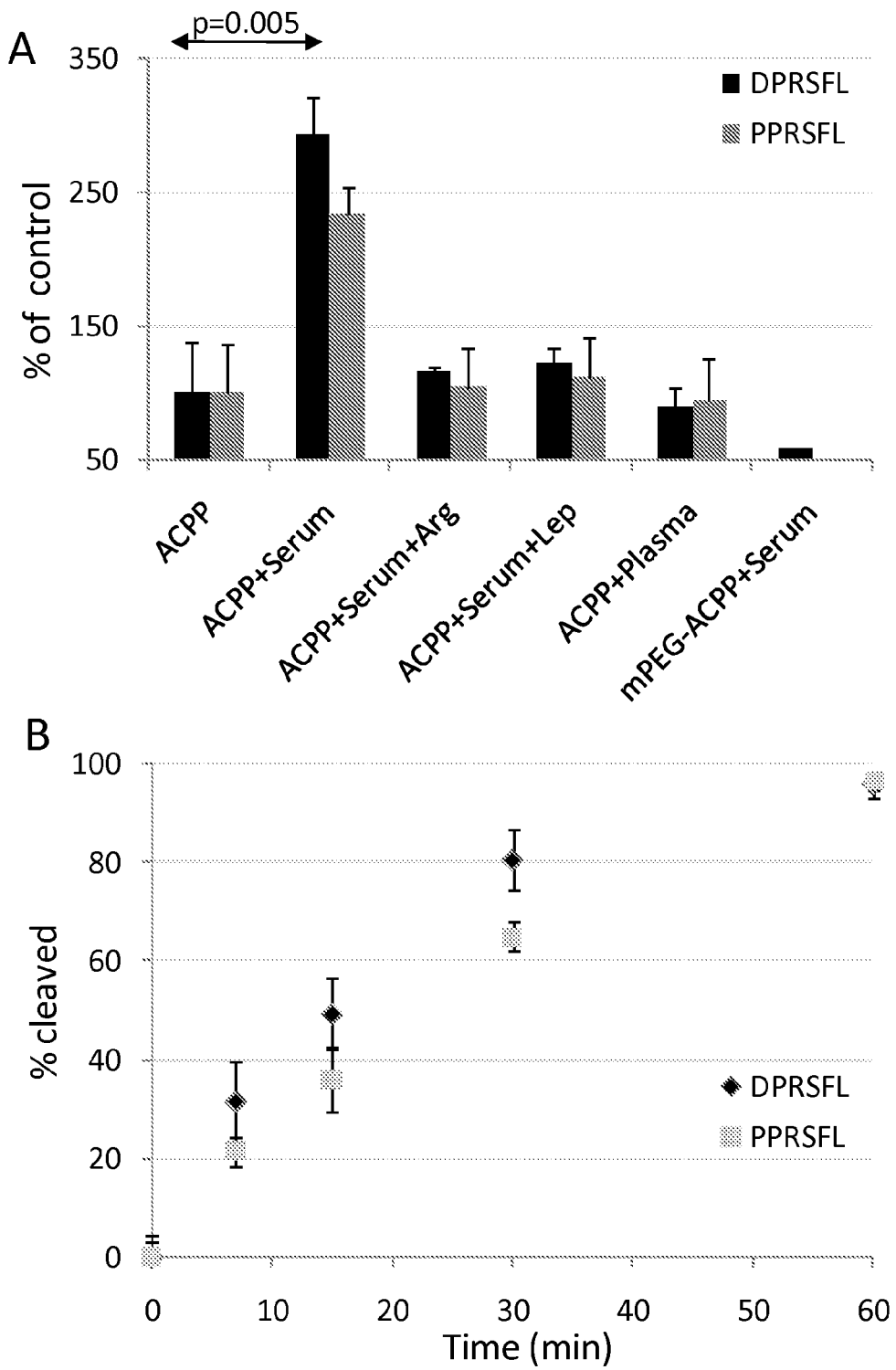
FIG. 23. DPRSFL (SEQ ID NO: 1)- and PPRSFL (SEQ ID NO: 2)-selective transport molecules are subject to proteolytic cleavage by endogenous proteases in serum. A: DPRSFL (SEQ ID NO: 1)-selective transport molecules and PPRSFL (SEQ ID NO: 2)-selective transport molecules after a 20 minute incubation in serum, serum plus direct thrombin inhibitor or plasma as indicated. Data are expressed as % increase over control, or selective transport molecules alone. B: shows a time course showing slower cleavage of PPRSFL (SEQ ID NO: 2)-selective transport molecules than DPRSFL (SEQ ID NO: 1)-selective transport molecules in serum. Each curve was fit to an exponential, which revealed a 51% drop in rate constant for PPRSFL (SEQ ID NO: 2)-selective transport molecules relative to DPRSFL (SEQ ID NO: 1)-selective transport molecules.
Figure 24:
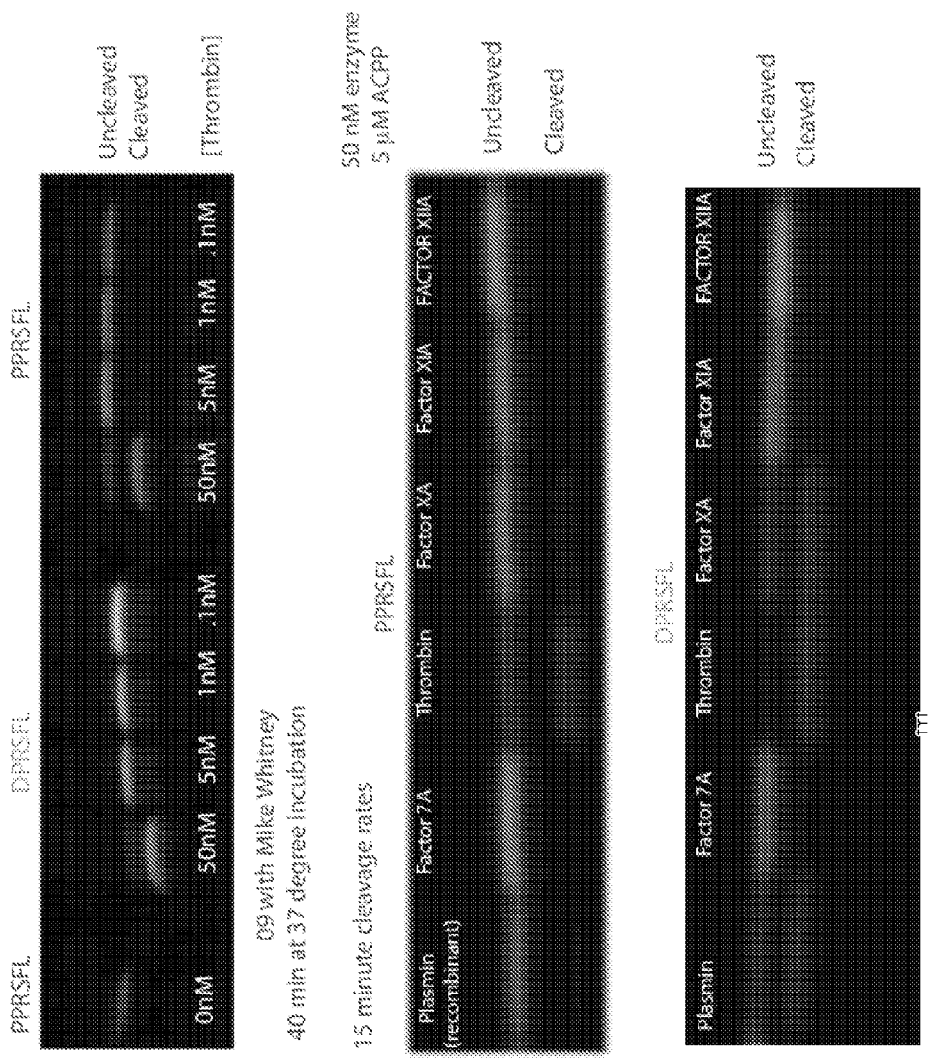
FIG. 24. Both DPRSFL (SEQ ID NO: 1) and PPRSFL (SEQ ID NO: 2) are cleaved by coagulation pathway proteases. Top panel: (1) Sensitivity of equimolar concentrations of DPRSFL (SEQ ID NO: 1) and PPRSFL (SEQ ID NO: 2) to enzymatic cleavage across a range of thrombin concentrations. Both DPRSFL (SEQ ID NO: 1) and PPRSFL (SEQ ID NO: 2) are cleaved by thrombin in vitro as shown by the lower molecular weight band ("cleaved") observed after incubation with 50 nM thrombin. Lower concentrations of thrombin (from 0.1 nM to 5 nM) results in inefficient cleavage after 40 minutes of incubation. Middle Panel (2): Comparison of the relative specificity of DPRSFL (SEQ ID NO: 1) and PPRSFL (SEQ ID NO: 2) cleavage with a panel of coagulation pathway enzymes. Cleavage was assessed after 15 minutes of enzyme-ACPP incubation. Cleavage of PPRSFL (SEQ ID NO: 2) is relatively selective for thrombin while DPRSFL (SEQ ID NO: 1) also shows cleavage products when incubated with plasmin and factor XA.
Figure 25:
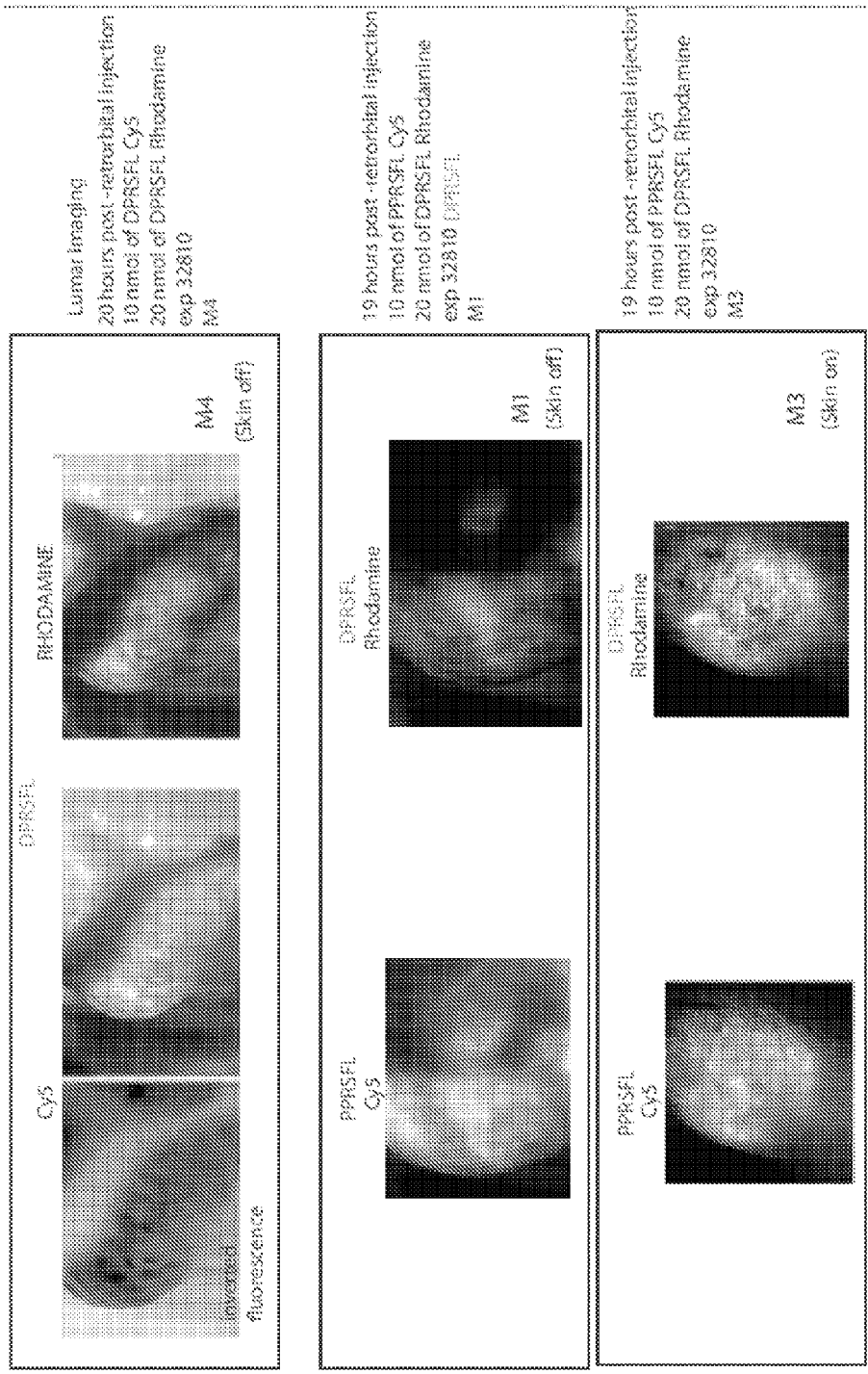
FIG. 25. Coinjection of DPRSFL (SEQ ID NO: 1) (Cy5 labeled) and of PPRSFL (SEQ ID NO: 2) (Rhodamine labeled) into mice bearing BI6F10 melanoma tumors demonstrates similar patterns of fluorescence. Top panel: Control experiment to test the colocalization of fluorescence from injections of DPRSFL labeled with Cy5 and of DPRSFL (SEQ ID NO: 1) labeled with Rhodamine. The left hand and middle panels shows fluorescence in whole tumor imaged with a Zeiss Lumar microscope after the skin was removed. The first image is of inverted fluorescence to better illustrate the heterogeneous uptake pattern. Similar heterogeneity is observed in the same animal with uptake of DPRSFL (SEQ ID NO: 1) labeled with rhodamine (extreme right hand panel). Middle Panel: Skin-off images of tumor fluorescence of PPRSFL-(Cy5) (SEQ ID NO: 5) and of DPRSFL-(Rhodamine) (SEQ ID NO: 6). The uptake pattern is grossly similar. Bottom Panel: Skin-on images also show similar tumor fluorescence with DPRSFL (SEQ ID NO: 1) and PPRSFL (SEQ ID NO: 2) after coinjection of PPRSFL-Cy5 (SEQ ID NO: 5) and of DPRSFL-Rhodamine (SEQ ID NO: 6).
Figure 26:
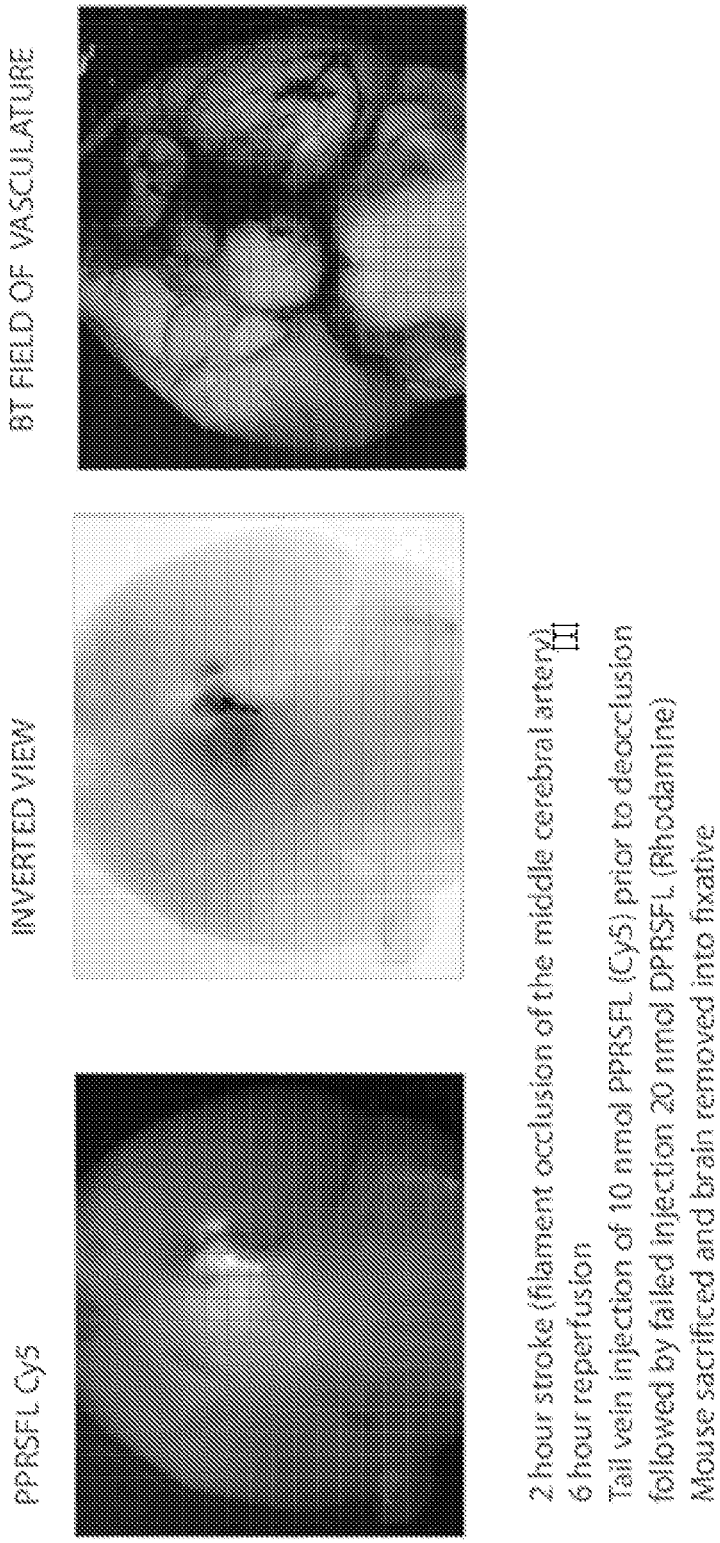
FIG. 26.

To determine whether MRI was possible using free peptides in principle, and also to look at whether thrombin could be used as a target protease for labeling atherosclerotic mice in vivo, we next injected 300 nmol of thrombin cleavable peptide into a two year old LDLR deficient mouse that had been fed a high cholesterol diet for 6-12 months. This animal was imaged pre-injection, immediately post injection and 12 hours thereafter to determine whether sufficient probe could be injected for visualization using T1-weighted imaging. On MRI, a new structure did appear (FIG. 21), but the animal clearly had difficulty breathing following injection of the probe. Though the breathing difficulty cleared up by the next day, the toxicity was so alarming that the free peptide approach to T1 MRI was abandoned in favor of PAMAM dendrimers.

Background Fluorescence: Implications for Selective Transport Molecule Development As expected, there were profound differences in biodistribution for the thrombin probe compared to the MMP probes. Liver and kidney uptake decreased significantly, with no uptake in cartilage and significantly lower uptake in skin. Though peptide taken from the liver was cleaved, this could easily have occured postmortem, since it was readily apparent during imaging that the thrombin cleavable peptides are excreted via the hepatobiliary pathway. Synovium was still problematic and was the largest source of background.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A molecule having the formula: $(A-X-B-C)_n-M$ wherein:
   C is a fluorescent moiety;
   A is a peptide with a sequence comprising a series of 5 glutamate residues;
   B is a peptide with a sequence comprising a series of 8 arginine residues;
   X is a cleavable linker comprising PRSFL (SEQ ID NO: 22);
   M is a macromolecular carrier; and
   n is an integer between 1 and 20;
   wherein M is bound to A or B.

2. The molecule of claim 1, wherein X is further attached to 6-aminohexanoyl, 5-amino-3-oxapentanoyl, or a combination thereof.

3. The molecule of claim 1, wherein X comprises a sequence selected from: DPRSFL (SEQ ID NO: 1), or PPRSFL (SEQ ID NO: 2).

4. The molecule of claim 1, wherein M is a macromolecular carrier selected from: a dendrimer, dextran, a PEG polymer, or albumin.

5. The molecule of claim 1, wherein M is a PEG polymer.

6. The molecule of claim 1, wherein the fluorescent moiety is an indocarbocyanine dye.

7. The molecule of claim 1, wherein the fluorescent moiety is selected from Cy5, Cy5.5, Cy7, Alexa 647, IRDYE 800CW, or a combination thereof.

8. The molecule of claim 1, wherein the fluorescent moiety is an MRI contrast agent.

9. A method of imaging thrombin activity in a subject, comprising imaging thrombin activity after the subject has been administered a molecule of the structure $(A-X-B-C)_n-M$, wherein
   C is a fluorescent moiety;
   A is a peptide with a sequence comprising a series of 5 glutamate residues;
   B is a peptide with a sequence comprising a series of 8 arginine residues;
   X is a cleavable linker comprising PRSFL (SEQ ID NO: 22);
   M is a macromolecular carrier; and
   n is an integer between 1 and 20;
   wherein M is bound to A or B.

10. The method of claim 9, wherein the fluorescent moiety is an indocarbocyanine dye.

11. The method of claim 9, wherein the fluorescent moiety is selected from Cy5, Cy5.5, Cy7, Alexa 647, IRDYE 800CW, or a combination thereof.

* * * * *